(12) United States Patent
Basnakian et al.

(10) Patent No.: US 9,650,674 B2
(45) Date of Patent: May 16, 2017

(54) NUCLEIC ACID PROBES AND METHODS OF USING THE SAME

(71) Applicant: Board of Trustees University of Arkansas, Little Rock, AR (US)

(72) Inventors: Alexei G. Basnakian, Little Rock, AR (US); Yevgeniy Apostolov, Little Rock, AR (US)

(73) Assignee: BIOVENTURES, LLC, Little Rock, AR (US)

( * ) Notice: Subject to any disclaimer, the term of this patent is extended or adjusted under 35 U.S.C. 154(b) by 162 days.

(21) Appl. No.: 14/056,497

(22) Filed: Oct. 17, 2013

(65) Prior Publication Data

US 2014/0112871 A1    Apr. 24, 2014

Related U.S. Application Data

(60) Provisional application No. 61/716,097, filed on Oct. 19, 2012.

(51) Int. Cl.
| | | |
|---|---|---|
| C12Q 1/68 | (2006.01) | |
| A61K 49/00 | (2006.01) | |
| C07H 21/04 | (2006.01) | |

(52) U.S. Cl.
CPC ........ *C12Q 1/6876* (2013.01); *A61K 49/0032* (2013.01); *A61K 49/0052* (2013.01); *C12Q 1/68* (2013.01); *C12Q 1/6816* (2013.01); *Y10T 436/143333* (2015.01)

(58) Field of Classification Search
None
See application file for complete search history.

(56) References Cited

U.S. PATENT DOCUMENTS

| | | | |
|---|---|---|---|
| 6,083,486 A | 7/2000 | Weissleder et al. | |
| 6,592,847 B1 | 7/2003 | Weissleder et al. | |
| 7,527,942 B2 | 5/2009 | Carey et al. | |
| 8,190,241 B2 | 5/2012 | Ntziachristos et al. | |
| 2006/0275775 A1 | 12/2006 | Weissleder et al. | |
| 2010/0203554 A1* | 8/2010 | Enderle et al. .......... | C12Q 1/42 435/7.4 |

OTHER PUBLICATIONS

Li et al., Nucleic Acids Research, 2000, 28: i-v.*
Li et al., Angew Chem. Int. Ed., 2000, 39: 1049-1052.*
Tyagi et al., Nat. Biotechnol., 2000, 18: 1191-1196.*
Venkatesan et al., Chem. Soc. Rev., 2008, 37: 648-663.*
Wunder et al., Arthritis & Rheumatism, 2004, 50: 2459-2465.*
Abel et al., "Analyses of apoptotic regulators CASP9 and DFFA at IP362, reveal rare allele variants in human neuroblastoma tumours," British Journal of Cancer, 2002, pp. 596-604, vol. 86.
Apostolov et al., "Role of EndoG in development and cell injury," Cell Death and Differentiation, 2007, pp. 1971-1974, vol. 14.
Apostolov et al., "Deoxyribonuclease I is Essential for DNA Fragmentation Induced by Gamma Radiation in Mice," BioOne Research Evolved, 2009, pp. 481-492, vol. 172, No. 4.
Baranovskii et al., "Human Deoxyribonucleases," Biochemistry, 2004, pp. 725-742, vol. 69, No. 6.
Basnakian et al., "Quantification of 3' OH DNA Breaks by Random Oligonucleotide-Primed Synthesis (ROPS) Assay," DNA and Cell Biology, 1996, vol. 15, No. 3.
Basnakian et al., "DNase I-Like Endonuclease in Rat Kidney Cortex That is Activated during Ischemia/Reperfusion Injury," J Am Soc Nephrol, 2002, pp. 1000-1007, vol. 13.
Basnakian et al., "Identification and expression of deoxyribonuclease (DNase) I alternative transcripts in the rat," Gene an International Journal on Genes and Genomes, 2002, pp. 87-96, vol. 289.
Basnakian et al., "Cisplatin Nephrotoxicity Is Mediated by Deoxyribonuclease I," Journal American Society of Nephrology, 2005, pp. 697-702, vol. 16.
Basnakian et al., "Endonuclease G promotes cell death of non-invasive human breast cancer cells," Experimental Cell Research, 2006, pp. 4139-4149, vol. 312.
Evans et al., "DNase II: genes, enzymes and function," Gene an International Journal on Genes and Genomes, 2003, pp. 1-15, vol. 322.
Hara et al., "Over Expression of Inhibitor of Caspase 2 Activated Deoxyribonuclease in Human Renal Cell Carcinoma Cells Enhances Their Resistance to Cytotoxic Chemotherapy in Vivo," The Journal of Urology, 2001, pp. 2491-2494, vol. 166.
Hengartner et al., "DNA destroyers," Nature, 2001, pp. 27-29, vol. 412.
Kishi et al., "DNase I: structure, function, and use in medicine and forensic science," Legal Medicine, 2001, pp. 69-83, vol. 3.
Kitahara et al., "Interferon-induced Trail-independent cell death in DNase II embryos," Eur. J. Immunol, 2010, pp. 2590-2598, vol. 40.
Komuro et al., "Cell Death during Corneal Storage at 4 C," Investigative Ophthalmology & Visual Science, 1999, pp. 2827-2832, vol. 40, No. 12.
Lacks, "Deoxyribonuclease I in Mammalian Tissues," The Journal of Biological Chemistry, 1981, pp. 2644-2648, vol. 256, No. 6.
Lichtenbelt et al., "Frequency of the deletion polymorphism of DNASE1L1 in 137 patients with acid maltase deficiency (Pope disease)," Experimental and Molecular Pathology, 2006, pp. 308-309, vol. 80.
Martinez-Valle et al., "DNase 1 activity in patients with systemic lupus erythematosus: relationship with epidemiological, clinical, immunological and therapeutical features," Lupus, 2009, pp. 418-423, vol. 18.
McDermott-Roe et al., "Endonuclease G is a novel determinant of cardiac hypertrophy and mitochondrial function," Nature, 2011, pp. 114-118, vol. 7367, No. 478.
Napirei et al., "Deoxyribonuclease 1 Aggravates Acetaminophen-Induced Liver Necrosis in Male CD-1 Mice," Hepatology, 2006, pp. 297-305, vol. 2, No. 43.

(Continued)

*Primary Examiner* — Ileana Popa
(74) *Attorney, Agent, or Firm* — Polsinelli PC

(57) ABSTRACT

The present invention provides a composition comprising a fluorescent nucleic acid probe that can be cleaved by enzymatic and non-enzymatic means, and methods of using the same. Advantageously, the nucleic acid probe may be used to detect and quantify nucleic acid cleavage in vitro, in situ, ex vivo, and in vivo.

9 Claims, 39 Drawing Sheets
(30 of 39 Drawing Sheet(s) Filed in Color)

(56) References Cited

OTHER PUBLICATIONS

Napirei et al., "Features of systemic lupus erythematosus in Dnase1-deficient mice," Nature Genetics, 2000, pp. 177-181, vol. 25.

Nishimura et al., "Presence of DNase y-like endonuclease in nuclei of neuronal differentiated PC12 cells," Apoptosis, 1998, pp. 97-103, vol. 3, No. 2.

Rajandram et al., "Expression of apoptotic tumour necrosis factor receptor-associated factor, caspase recruitment domain and cell death-inducing DFF-45 effector genes in therapy-treated renal cell carcinoma," Nephrology, 2009, pp. 205-212, vol. 14.

Shiokawa et al., "Purification, Characterization, and Amino Acid Sequencing of DNase y from Rat Spleen," Archives of Biochemistry and Biophysics, 1997, pp. 15-20, vol. 346, No. 1.

Shiokawa et al., "Characterization of Human DNase I Family Endonucleases and Activation of DNase y during Apoptosis," Biochemistry, 2001, pp. 143-152, vol. 40.

Wang et al., "Porcine Spleen Deoxyribonuclease II: Covalent Structure, cDNA Sequence, Molecular Cloning, and Gene Expression," The Journal of Biological Chemistry, 1998, pp. 17192-17198, vol. 273.

Wang et al., "Sensitivity of human prostate cancer cells to chemotherapeutic drugs depends on EndoG expression regulated by promoter methylation," Cancer Letters, 2008, pp. 132-143, vol. 270.

Weissleder et al., "In vivo imaging of tumors with protease-activated near-infrared fluorescent probes," Nature Biotechnology, 1999, pp. 375-378, vol. 4, No. 17.

Widlak et al., "Roles of the Major Apoptotic Nuclease—DNA Fragmentation Factor—in Biology and Disease," Cellular and Molecular Life Sciences, 2009, pp. 263-274, vol. 66.

Yan et al., "A unique role of the DNA fragmentation factor in maintaining genomic stability," PNAS, 2006, pp. 1504-1509, vol. 103, No. 5.

Yan et al., "Increased skin carcinogenesis in caspase-activated DNase knockout mice," Carcinogenesis, 2009, pp. 1776-1780, vol. 30, No. 10.

Yang et al., "Nucleases:diversity of structure, function and mechanism," Quarterly Reviews of Biophysics, 2011, pp. 1-93, vol. 44.

* cited by examiner

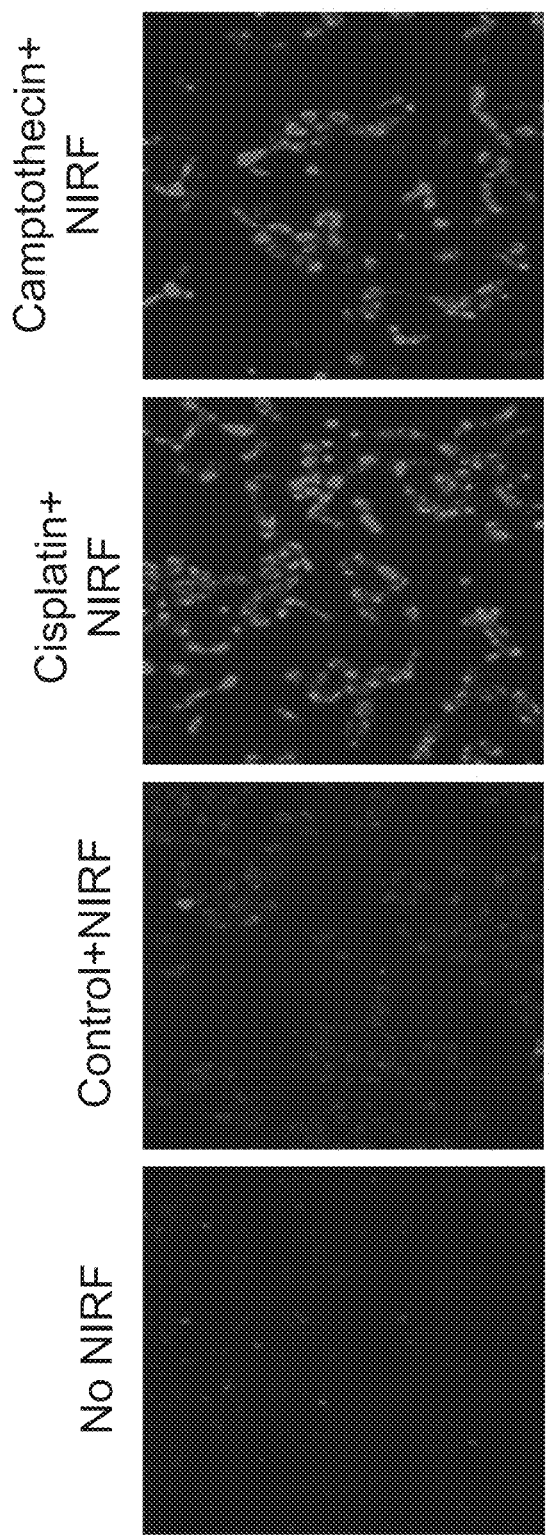

A

B

NUCLEIC ACID PROBES AND METHODS OF USING THE SAME

CROSS REFERENCE TO RELATED APPLICATIONS

This application claims the priority of U.S. provisional application No. 61/716,097, filed Oct. 19, 2012, which is hereby incorporated by reference in its entirety.

GOVERNMENTAL RIGHTS

This invention was made with government support under DK078908-01 awarded by the National Institute of Diabetes and Digestive and Kidney Disease. The government has certain rights in the invention.

FIELD OF THE INVENTION

The invention encompasses compositions comprising a fluorescent nucleic acid probe that can be cleaved by enzymatic and non-enzymatic means, and methods of using the same. Advantageously, the nucleic acid probe may be used to detect and quantify nucleic acid cleavage in vitro, in situ, ex vivo, and in vivo.

BACKGROUND OF THE INVENTION

Most knowledge about nucleic acid cleavage has resulted from the study of enzymatic or non-enzymatic cleavage of nucleic acids in vitro. It may be expected that such findings will not always be consistent with how similar systems behave in vivo. Moreover, the contribution nucleases make to health, and their role in cell death associated with almost any disease, have garnered more attention in recent years. For example, human recombinant DNase I is used to treat patients with cystic fibrosis whose airways become blocked by thick mucus containing high concentrations of bacterial DNA, and is being evaluated for the treatment for humans with systemic lupus erythematosus. Hence, there is a need in the art for nucleic acid probes that can be used to detect and quantify nucleic acid cleavage in vitro, in situ, ex vivo, and in vivo.

SUMMARY OF THE INVENTION

One aspect of the present invention encompasses a method for detecting nucleic acid cleavage in a sample. The method comprises: (i) providing a nucleic acid probe comprising two components, A1-A2-A3 and A5-A6-A7, and optionally a third component, A4; wherein (a) A1 and A7 are fluorophores, (b) A2 and A6 are each a single-stranded nucleic acid about 1 to about 50 nucleotides in length that are not complementary to the other, nor to A3, A4, or A5, and at least one of A2 or A6 comprises a nuclease recognition sequence, (c) A3 and A5 are each a single-stranded nucleic acid about 2 to about 80 nucleotides in length and comprise a region complementary to the other, such that A3 and A5 associate when A1-A2-A3 and A5-A6-A7 are not cleaved and disassociate when at least one of A1-A2-A3 or A5-A6-A7 is cleaved, (d) A4 is a single-stranded nucleic acid comprising about 4 nucleotides to about 50 nucleotides in length that, when present, connects and forms a loop structure between A3 and A5, whereby the fluorescence of A1 and A7 is quenched when A3 and A5 associate and is detectable when A3 and A5 disassociate; (ii) contacting the sample with the nucleic acid probe and detecting fluorescence in the sample, whereby fluorescence in a sample indicates nucleic acid cleavage of at least one component of the nucleic acid probe and dissociation of A3 and A5; and (iii) optionally, quantifying the fluorescence in the sample.

Another aspect of the present invention encompasses a method for detecting nucleic acid cleavage in a subject. The method comprises: (i) administering to a subject a nucleic acid probe comprising two components, A1-A2-A3 and A5-A6-A7, and optionally a third component, A4; wherein (a) A1 and A7 are near-infrared fluorophores, (b) A2 and A6 are each a single-stranded nucleic acid about 1 to about 50 nucleotides in length that are not complementary to the other nor to A3, A4, or A5, and at least one of A2 or A6 comprises a nuclease recognition sequence, (c) A3 and A5 are each a single-stranded nucleic acid about 2 to about 80 nucleotides in length and comprise a region complementary to the other, such that A3 and A5 associate when A1-A2-A3 and A5-A6-A7 are not cleaved and disassociate when at least one of A1-A2-A3 or A5-A6-A7 is cleaved, (d) A4 is a single-stranded nucleic acid comprising about 4 nucleotides to about 50 nucleotides in length that, when present, connects and forms a loop structure between A3 and A5, whereby the fluorescence of A1 and A7 is detectable when A3 and A5 disassociate and is quenched when A3 and A5 associate; and (ii) performing a signal acquisition scan on the subject to detect the fluorescence signal, whereby fluorescence indicates nucleic acid cleavage of at least one component of the nucleic acid probe and dissociation of A3 and A5. In certain embodiments, the method may further comprise processing data from the signal acquisition to form an image of the subject, wherein the data is a read-out of the fluorescence emitted by the fluorophores of the cleaved nucleic acid probes in the subject.

A composition comprising a nucleic acid probe, the nucleic acid probe comprising two components: A1-A2-A3 and A5-A6-A7, wherein (a) A1 and A7 are fluorophores, (b) A2 and A6 are each a single-stranded nucleic acid about 1 to about 50 nucleotides in length that are not complementary to the other nor to A3 or A5, and at least one of A2 or A6 comprises a nuclease recognition sequence, (c) A3 and A5 are each a single-stranded nucleic acid about 2 to about 80 nucleotides in length and comprise a region complementary to the other, such that A3 and A5 associate when A1-A2-A3 and A5-A6-A7 are not cleaved and disassociate when at least one of A1-A2-A3 or A5-A6-A7 is cleaved, whereby the fluorescence of A1 and A7 is quenched when A3 and A5 associate and is detectable when A3 and A5 disassociate. In certain embodiments, the composition may comprise a third component, A4, wherein A4 is a single-stranded nucleic acid comprising about 4 nucleotides to about 50 nucleotides that connects and forms a loop structure between A3 and A5.

Other aspects and iterations of the invention are described more thoroughly below.

REFERENCE TO COLOR FIGURES

The application file contains at least one photograph executed in color. Copies of this patent application publication with color photographs will be provided by the Office upon request and payment of the necessary fee.

DETAILED DESCRIPTION OF THE INVENTION

Figure 1A:
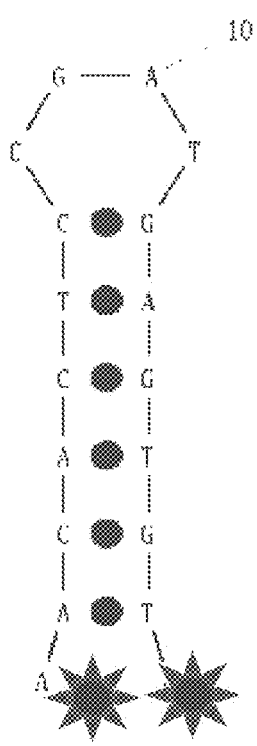
FIG. 1 A illustrates the hairpin structures of the DNA probes AB259.1 (SEQ ID NO: 1), AB259.3 (SEQ ID NO: 2), and AB259.5 (SEQ ID NO: 3), and B-D depicts graphs showing fluorescence is quenched when the fluorophores (Cy5.5) are in close proximity and activated when separated due to DNA denaturing or degradation. (A) DNA probes form a hairpin structure, bringing the fluorophores in close proximity. (B) Baseline fluorescence of DNA probes. (C) Denaturing by heat increases the hairpin probes' fluorescence, while re-annealing by cooling decreases it. (D) Denaturing by alkaline pH also increases the probes' fluorescence. *P<0.05 compared to negative control.
Figure 1A:
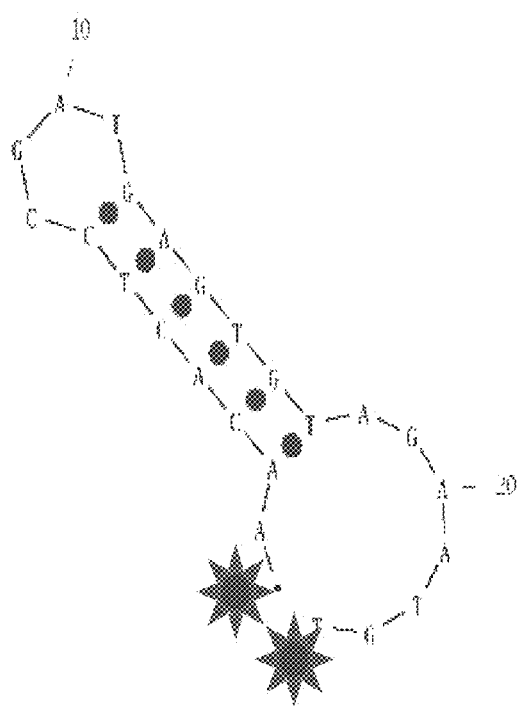
Figure 1A:
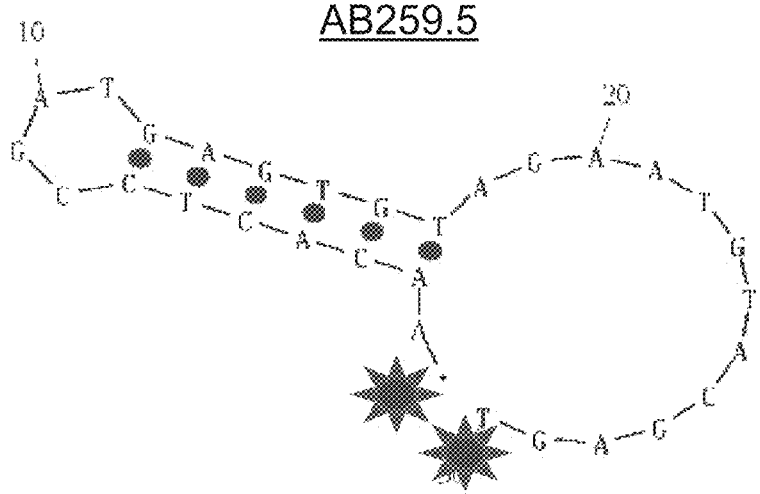
Figure 1:
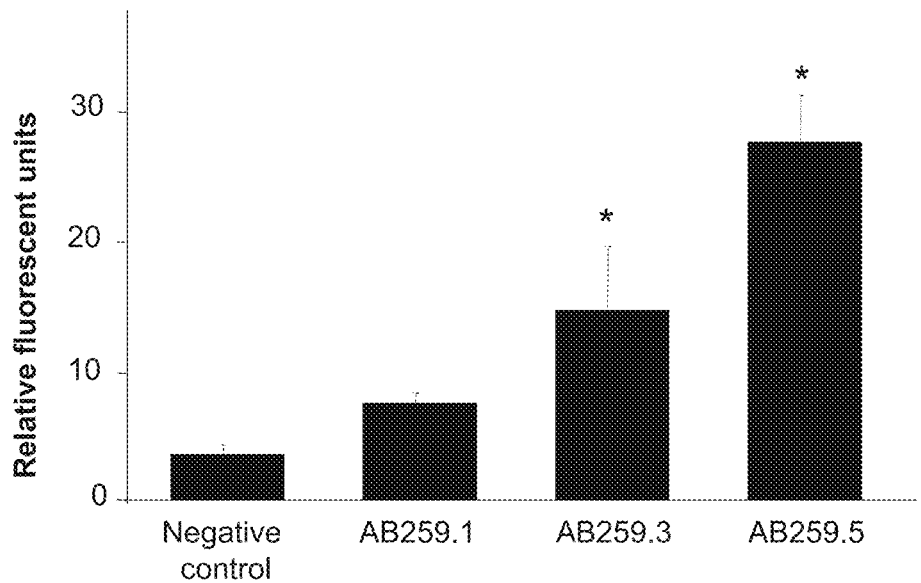
Figure 1:
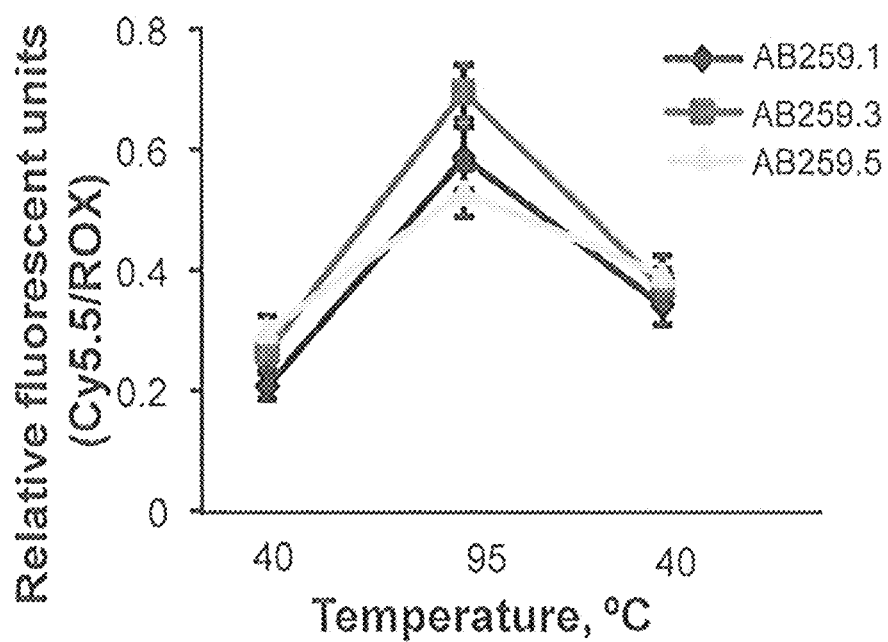
Figure 1D:
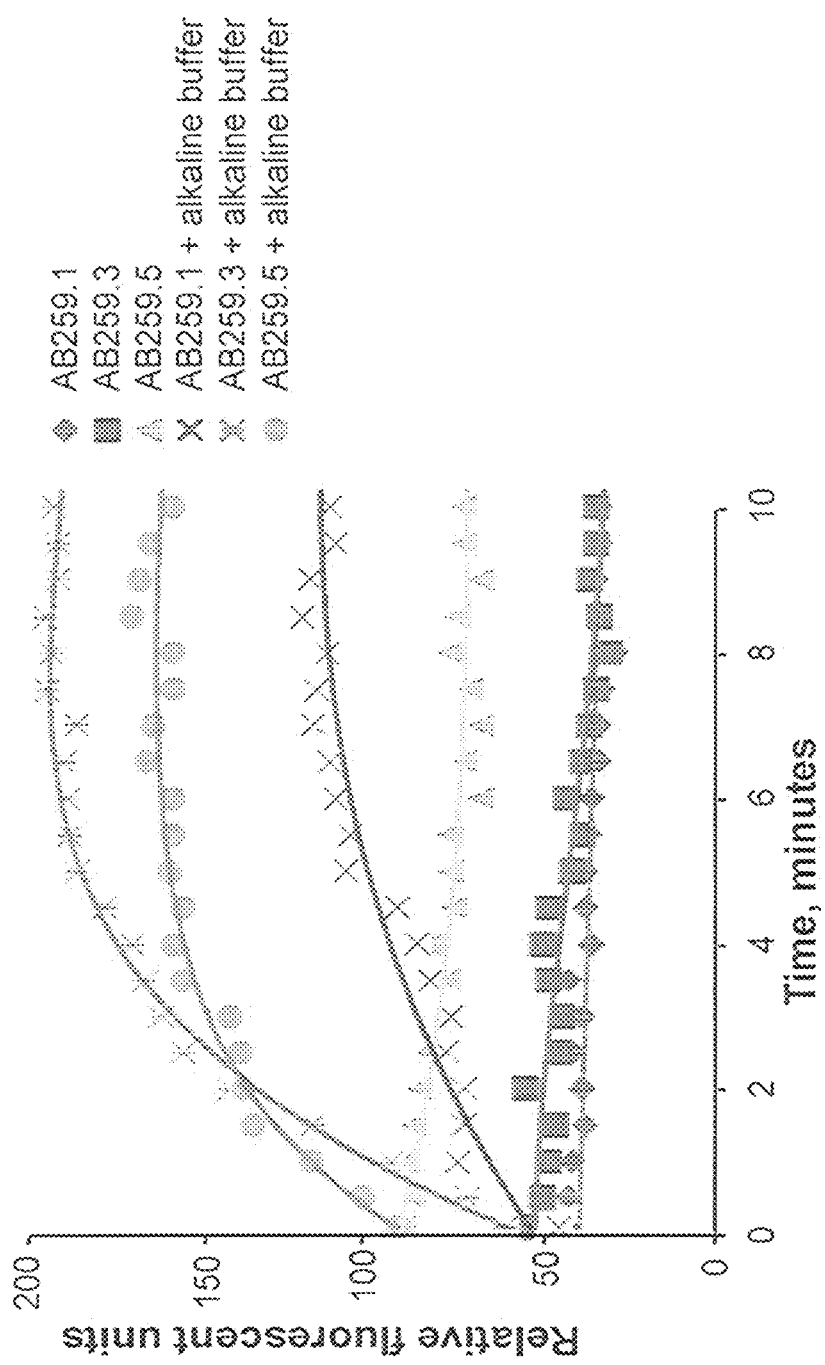

The present invention provides a composition comprising a fluorescent nucleic acid probe that can be cleaved by enzymatic and non-enzymatic means. Using a nucleic acid probe of the invention, it is now possible to assay cleavage of RNA and DNA quickly and with a high degree of sensitivity. It is also now possible to assay nuclease activity quickly and with a degree of sensitivity and specificity not possible at the time of the invention. Advantageously, a nucleic acid probe of the invention may be used to detect and quantify nucleic acid cleavage in vitro, in situ, ex vivo, and in vivo. A nucleic acid probe of the invention and methods of using such a nucleic acid probe are described below.

I. Composition Comprising a Nucleic Acid Probe

One aspect of the present invention encompasses a nucleic acid probe, wherein the probe comprises a nucleotide polymer and at least one fluorophore that can be quenched depending on the conformation of the nucleic acid. As used herein, the term "quenching" refers to loss of fluorescence signal due to short-range interactions between a fluorophore and the local molecular environment (including other fluorophores). Loss of fluorescence is reversible to the extent that the causative molecular interactions can be controlled. According to the invention, a nucleotide polymer comprises at least two complementary sequences, which associate under non-denaturing conditions. Importantly, the fluorophore is brought into close proximity to another species by the association of the complementary sequences and the fluorophore and other species are positioned relative to each other such that the fluorophore's fluorescence is quenched. As explained in further detail below, the other species may be another fluorophore or a species that does not emit fluorescence but is capable of quenching a fluorophore (e.g. paramagnetic species or heavy atoms). Conversely, in denaturing conditions and/or in conditions that favor nucleic acid cleavage, the fluorophore and other species are forced apart and fluorescence is emitted. As used herein, "associate under non-denaturing conditions" refers to the interaction of two polynucleotide sequences as a result of base-pairing between complementary nucleotides under conditions that do not disrupt the hydrogen bonds between the paired nucleotides, while "denaturing conditions" refers to conditions that disrupt the hydrogen bonds between the base pairs (for example, high temperatures and low pH). The term "nucleic acid cleavage" refers to the breaking of the phosphodiester bonds that make up the backbone of the nucleotide polymer.

A nucleotide polymer, a fluorophore and methods of generating a nucleic acid probe of the invention are described below.

(a) Design of a Nucleic Acid Probe

According to the invention, a nucleic acid probe encompasses a fluorophore and at least two complementary sequences, which associate under non-denaturing conditions. Importantly, the fluorophore is brought into close proximity to another species by the association of the complementary sequences and the fluorophore and other species are positioned relative to each other such that the fluorophore's fluorescence is quenched. Conversely, in denaturing conditions and/or in conditions that favor nucleic acid cleavage, the fluorophore and other species are forced apart and fluorescence is emitted. The structure of a nucleic acid probe of the invention is advantageously designed to facilitate these interactions.

Figure 12:
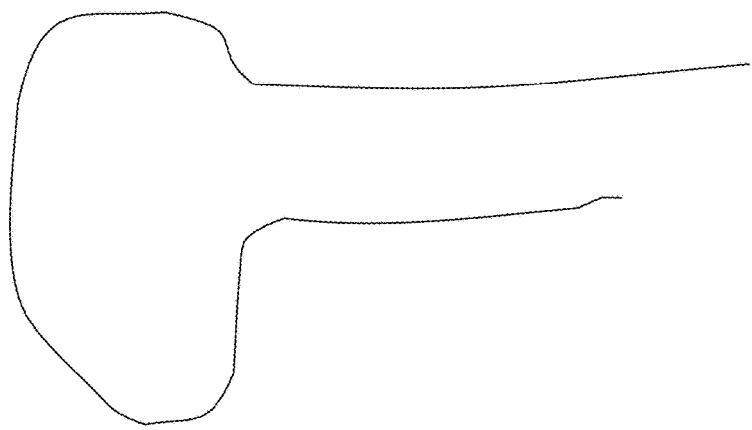
FIG. 12 depicts illustrations of how the nucleic acid probe of the invention may be configured. In (A), a nucleic acid probe of the invention has a simple stem-loop structure. In (B), a nucleic acid probe of the invention has a more complex stem-loop structure.
Figure 12:
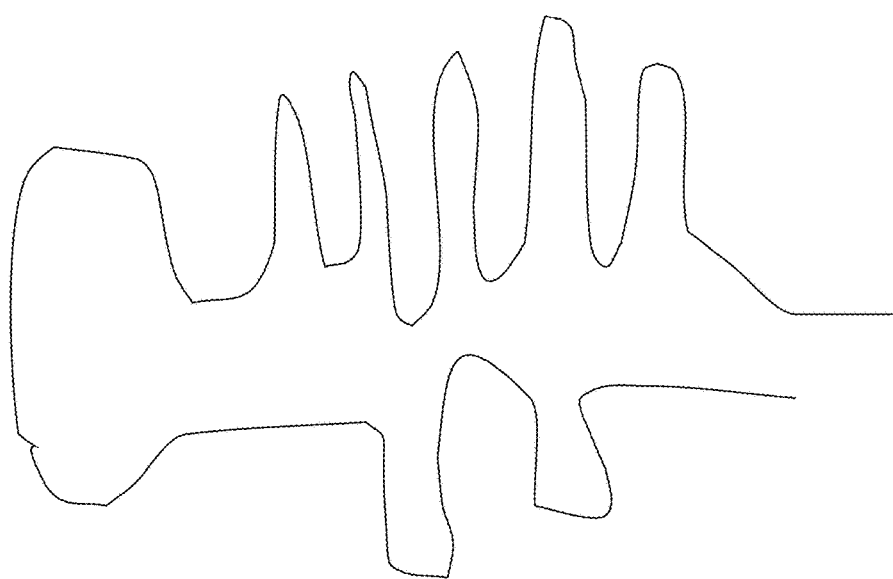

In one aspect of the invention, a nucleic acid probe is designed such that complementary sequences may be on the same or a different single-stranded nucleic acid. In certain embodiments, complementary sequences are on the same single-stranded nucleic acid (i.e. the sequences are self-complementary). For example, complementary sequences may be on the same single-stranded nucleic acid separated by a nucleic acid sequence that is not self-complementary with any other sequence on the nucleic acid, with the fluorophores attached to the 5'- and 3'-ends of the nucleic acid. Thus, when the self-complementary sequences associate, a stem-loop structure is formed bringing the fluorophores into close proximity. Both simple stem-loop structures (e.g. with only one loop region) and more complex stem-loop structures (e.g. with more than one loop region) are contemplated and within the bounds of the invention (see FIG. 12). In alternative embodiments, complementary sequences are on different single-stranded nucleic acids. For example, a first single-stranded nucleic acid may comprise a nucleotide sequence that is complementary to a sequence on a second single-stranded nucleic acid, with each nucleic acid further comprising a fluorophore on either the 5'- or 3'-end of the nucleic acid, such that when the complementary sequences associate, the fluorophores are brought into close proximity but the nucleic acid probe does not have a loop structure between the complementary strands. Further description may be found in Example 4 and FIG. 4E. Suitable fluorophores and nucleic acids are described below in Section Ib and Ic.

In another aspect of the invention, a nucleic acid probe of the invention is designed such that a recognition site is engineered at a location in a nucleotide polymer, whereby cleavage of the nucleotide polymer at the recognition site results in separation of the fluorophores. Suitable recognition sites are described in Section Ib. Typically, recognition sites are located within the nucleotide sequence between the self-complementary sequences and the fluorophores. In some embodiments, a recognition site is within 10 nucleotides from the 5'-end of the nucleic acid. In other embodiments, a recognition site is within 30 nucleotides from the 5'-end of the nucleic acid. For example, a recognition site may be within 1, 2, 3, 4, 5, 6, 7, 8, 9, 19, 11, 12, 14, 15, 16, 17, 18, 19, 20, 21, 22, 23, 24, 25, 26, 27, 28, 29, or 30 nucleotides from the 5'-end of the nucleic acid. In alternative embodiments, the recognition site is within 10 nucleotides of the 3'-end of the nucleic acid. In different embodiments, the recognition site is within 30 nucleotides from the 3'-end. For example, a recognition site may be within 1, 2, 3, 4, 5, 6, 7, 8, 9, 19, 11, 12, 14, 15, 16, 17, 18, 19, 20, 21, 22, 23, 24, 25, 26, 27, 28, 29, or 30 nucleotides from the 3'-end of the nucleic acid.

In certain embodiments, a nucleic acid probe of the invention comprises two components, A1-A2-A3 and A5-A6-A7. Each component is a separate entity (i.e. A1-A2-A3 is a distinct entity from A5-A6-A7). A1 and A7 are fluorophores. The fluorescence of A1 and A7 is quenched when A3 and A5 associate and is detectable when A3 and A5 disassociate. A2 and A6 are each a single-stranded nucleic acid about 1 to about 50 nucleotides in length and at least one of A2 or A6 comprises a nuclease recognition sequence. A2 is not complementary to A3, A5, or A6. A6 is not complementary to A2, A3, or A6. In some embodiments, A2 and/or A6 may be about 1 to about 50 nucleotides in length. For example, A2 and/or A6 may be 1, 2, 3, 4, 5, 6, 7, 8, 9, 19, 11, 12, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length. In other embodiments, A2 and/or A6 may be about 1 to about 10 nucleotides in length. In still other embodiments, A2 and/or A6 may be about 10 to about 20 nucleotides in length. In yet other embodiments, A2 and/or A6 may be about 4 to about 10 nucleotides in length. A2 and A6 may or may not be the exact same length. In some embodiments, A2 and A6 are the same length. In other embodiments, A2 and A6 are not the same length.

A3 and A5 are each a single-stranded nucleic acid about 2 to about 80 nucleotides in length and comprise a region complementary to the other, such that A3 and A5 associate when A1-A2-A3 and A5-A6-A7 are not cleaved and disassociate when at least one of A1-A2-A3 or A5-A6-A7 is cleaved. In some embodiments, A3 and/or A5 may is about 2 to about 80 nucleotides in length. For example, A2 and/or A6 may be 1, 2, 3, 4, 5, 6, 7, 8, 9, 10, 11, 12, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides in length. In other embodiments, A3 and/or A5 is about 5 to about 50 nucleotides in length. In other embodiments, A3 and/or A5 is about 5 to about 25 nucleotides in length. A2 and A6 need not be the exact same length provided the complementary region is the same length. Typically, the complementary region is at least 5 nucleotide in length. The nucleic acid probe's structure (i) positions A1 and A7 relative to each other such that they quench each other's fluorescence when A3 associates with A5, and A1-A2-A3 or A5-A6-A7 are not cleaved; and (ii) can be cleaved by enzymatic or non-enzymatic means if present in a sample, causing the fluorophores on the nucleic acid probe to dissociate and emit fluorescence. Stated another way, fluorescence in a sample indicates nucleic acid cleavage of at least one component of the nucleic acid probe (e.g. cleavage of A1-A2-A3, A5-A6-A7, or A1-A2-A3 and A5-A6-A7) and dissociation of A3 and A5.

Figure 13:
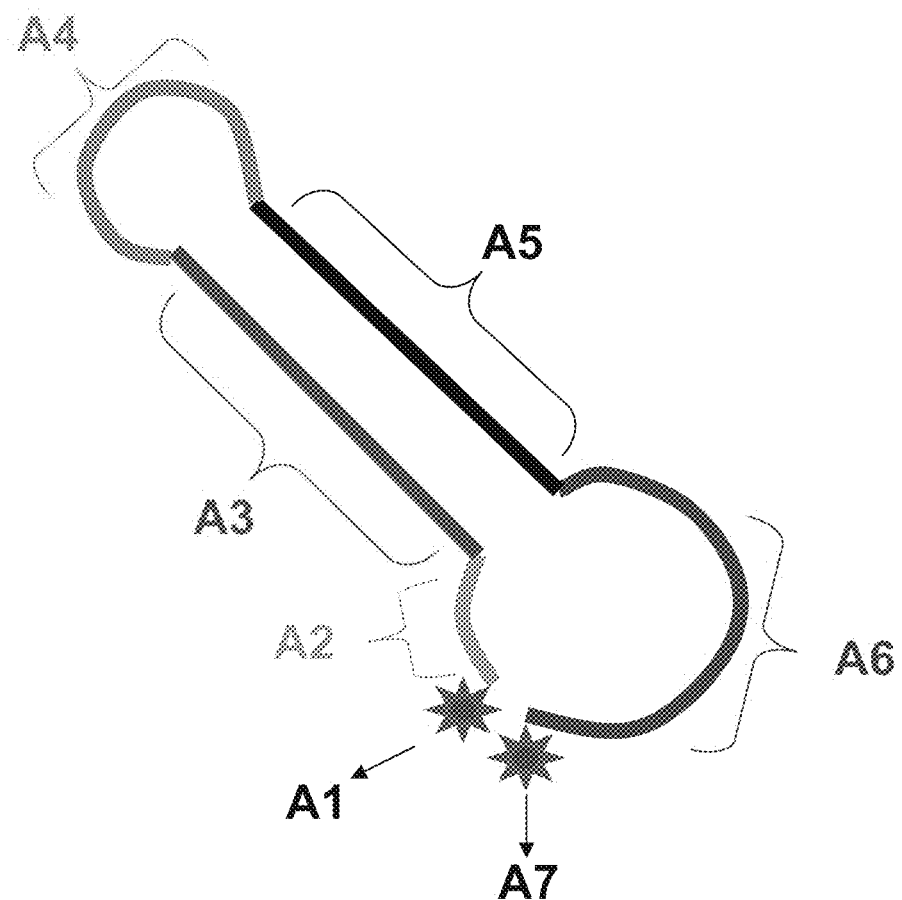
FIG. 13 depicts an illustration of the nucleic acid probe design.

In other embodiments, a nucleic acid probe of the invention comprises two components, A1-A2-A3 and A5-A6-A7, linked by a third component, A4. All three components form a single entity (i.e. A1-A2-A3-A4-A5-A6-A7). A1, A2, A3, A5, A6, and A7 are described above. A4 is a single-stranded nucleic acid that connects and forms a loop structure between A3 and A5, and is not complementary to A2, A3, A5, or A6. In some embodiments, A4 is about 4 nucleotides to about 50 nucleotides long. For example, A4 may be 1, 2, 3, 4, 5, 6, 7, 8, 9, 19, 11, 12, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length. In other embodiments, A4 is about 4 to about 30 nucleotides in length. In still other embodiments, A4 is about 4 to about 10 nucleotides in length. The nucleic acid probe's structure (i) positions A1 and A7 relative to each other such that they quench each other's fluorescence when A3 associates with A5, and A1-A2-A3 or A5-A6-A7 are not cleaved; and (ii) can be cleaved by enzymatic or non-enzymatic means if present in a sample, causing the fluorophores on the nucleic acid probe to dissociate and emit fluorescence. An illustration of a nucleic acid probe of the invention can be seen in FIG. 13.

(b) Nucleotide Polymer

A nucleotide polymer of the invention may be any polymer made from repeating units of nucleotides. As used herein, the term "nucleotide polymer", "polynucleotide" and "nucleic acid" may be used interchangeably. A nucleotide polymer may comprise natural, modified or artificial nucleotides, or a combination thereof. In some embodiments, a nucleotide polymer may comprise natural nucleotides (i.e. A, T, G, C, or U). In other embodiments, a nucleotide polymer may comprise modified nucleotides. "Modified nucleotides", as used herein, refers to natural nucleotides with additions or changes made to various positions. Numerous modifications have been described in the art. Modifications may occur at, but are not restricted to, the sugar 2' position, the C-5 position of pyrimidines, and the 8-position of purines. Examples of suitable modified DNA or RNA bases may include 2'-fluoro nucleotides, 2'-amino nucleotides, 5'aminoallyl-2'fluoro nucleotides and phosphorothioate nucleotides (monothiophosphate and dithiophosphate). In different embodiments, a nucleotide polymer may comprise artificial nucleotides. The term "artificial nucleotides" refers to artificial structural mimics of nucleic acids that have an altered phosphate backbone, sugar, base, or combination thereof. Non-limiting examples of artificial nucleotides include peptide nucleic acid (PNA), locked nucleic acids (LNA), glycol nucleic acid (GNA), threose nucleic acid (TNA), and phosphorodiamidate morpholine oliomers (PMO).

In an exemplary embodiment, a nucleic acid probe of the invention comprises a nucleotide polymer, the nucleotide polymer comprising natural nucleotides. In a preferred embodiment, a nucleic acid probe of the invention comprises deoxyribonucleic acid (DNA). In another preferred embodiment, a nucleic acid probe of the invention comprises ribonucleic acid (RNA). In another exemplary embodiment, a nucleic acid probe of the invention comprises a nucleotide polymer, the nucleotide polymer comprising a combination of natural and modified nucleotides. In another exemplary embodiment, a nucleic acid probe of the invention comprises a nucleotide polymer, the nucleotide polymer comprising a combination of natural and artificial nucleotides. In yet another exemplary embodiment, a nucleic acid probe of the invention comprises a nucleotide polymer, the nucleotide polymer comprising a combination of natural, modified and artificial nucleotides.

One skilled in the art will appreciate that the length of a nucleotide polymer may vary depending on a number of factors, including the desired structure of the nucleic acid probe. For example, a nucleic acid probe comprising more than one nucleotide polymer may be shorter in length than a nucleic acid probe comprising a single nucleotide polymer. Typically, a nucleotide polymer is about 5 to about 150 nucleotides in length. In some embodiments, the nucleotide polymer is at least 50 nucleotides in length. For example, the nucleotide polymer is at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides. In other embodiments, the nucleotide polymer is at least 100 nucleotides length. For example, the nucleotide polymer is at least 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or at least 150 nucleotides in length. In some embodiments, a nucleotide polymer may be about 6 to about 10 nucleotides in length. For example, a nucleotide polymer may be about 6, about 7, about 8, about 9 or about 10 nucleotides in length. In some embodiments, a nucleotide polymer may be about 11 to about 15 nucleotides in length. For example, a nucleotide polymer may be about 11, about 12, about 13, about 14 or about 15 nucleotides in length. In some embodiments, a nucleotide polymer may be about 16 to about 20 nucleotides in length. For example, a nucleotide polymer may be about 16, about 17, about 18, about 19 or about 20 nucleotides in length. In other embodiments, a nucleotide polymer may be about 21 to about 25 nucleotides in length. For example, a nucleotide polymer may be about 21, about 22, about 23, about 24 or about 25 nucleotides in length. In other embodiments, a nucleotide polymer may be about 26 to about 30 nucleotides in length. For example, a nucleotide polymer may be about 26, about 27, about 28, about 29 or about 30 nucleotides in length. In other embodiments, a nucleotide polymer may be about 31 to about 40 nucleotides in length. For example, a nucleotide polymer may be about 31, about 32, about 33, about 34, about 35, about 36, about 37, about 38, about 39, or about 40 nucleotides in length. In still other embodiments, a nucleotide polymer is about 41 to about 50 nucleotides in length. For example, a nucleotide polymer may be about 41, about 42, about 43, about 44, about 45, about 46, about 47, about 48, about 49, or about 50 nucleotides in length. In an exemplary embodiment, a nucleotide polymer is about 5 to about 50 nucleotides in length.

Preferably, a nucleotide polymer is single-stranded. Methods of synthesizing single-stranded and double-stranded nucleic acids of about 5 to about 150 nucleotides in length using natural, modified, and/or artificial nucleotides are well known in the art.

In another aspect of the invention, a nucleotide polymer may be cleaved. Cleavage may be enzymatic or non-enzymatic. One of skilled in the art will appreciate that cleavage of a nucleic acid can occur anywhere provided the nucleic acid is in contact with the enzymatic or non-enzymatic means of cleavage. For example, cleavage can occur in vitro, in situ, in vivo, or ex vivo. In some embodiments, cleavage occurs in vitro. In other embodiments, cleavage occurs in situ. In different embodiments, cleavage occurs in vivo. In still other embodiments, cleavage occurs ex vivo. If cleavage is to occur inside a cell, a nucleic acid probe may be designed to have increased cell permeability. For example, various formulations, as described below, may increase cell permeability. Alternatively, a cell may passively or actively transport the nucleic acid probe via endocytosis or other passive and active transport mechanisms well known in the art.

In some embodiments, cleavage is non-enzymatic. For example, breaks in a single-stranded nucleic acid polymer may occur due to oxidative damage mediated by reactive oxygen species, ultraviolet radiation, other radiation frequencies, hydrolysis or thermal disruption, viruses, plant toxins, bacterial toxins, synthetic and natural mutagenic chemicals, anti-metabolic antibiotics and anti-cancer drugs, deficiency of DNA repair or synthesis, endogenous substance such as antibodies (immunoglobulins), mechanical trauma or pH change. Causes of oxidative injury may include, but are not limited to, normal metabolism or the metabolism of toxic compounds. Non-limiting examples of reactive oxygen species include superoxide, hydroxyl radicals and hydrogen peroxide. Exposure to UV radiation (200-400 nm) most commonly occurs from the sun, but may also occur due to occupational exposure and exposure during medical therapy (e.g. phototherapy). Other radiation frequencies may include, but are not limited to, x-rays, alpha particles, beta particles, positrons, and gamma rays, and sources of exposure may include space/cosmic exposure, environmental exposure, occupational exposure, and exposure during medical therapy (e.g. radiation therapy or radiotherapy). Non-limiting examples of plant toxins include alkaloids from plants, such as those from Vinca species. Non-limiting examples of toxic compounds include alkylating agents and intercalating agents. Sources of exposure to mutagenic compounds may include, but are not limited to, space/cosmic exposure, environmental exposure, occupational exposure, and exposure during medical therapy. Non-limiting examples of mechanic trauma include DNA damage in cells due to osmotic shock or rapid change of atmospheric pressure. Non-limiting examples of anti-metabolic antibacterial and anti-cancer drugs include sulfanilamides and methotrexate. Non-limiting examples of hydrolysis or thermal disruption include those generated by burns and DNA denaturing, etc. Non-limiting examples of change of pH include acidosis and alkalosis. Non-limiting examples of antibodies include immunoglobulin A, G, M, D, E that occur for example autoimmune diseases such as lupus. Non-limiting examples of deficiency of DNA repair or synthesis include, but are not limited to, congenital (such as Xeroderma pigmentosum), spontaneous (such as normal or accelerated aging), or induced (such as topoisomerase inhibitors). In some exemplary embodiments, cleavage is non-enzymatic and caused by oxidative injury. In other exemplary embodiments, cleavage is non-enzymatic and caused by radiation.

In other embodiments cleavage is enzymatic. Nucleases are enzymes capable of cleaving the phosphodiester bonds between the nucleotide subunits of nucleic acid. Nucleases may cleave nucleic acid in a non-specific manner (i.e. sequence-independent), or may cleave nucleic acid at specific sites defined by either a particular nucleotide or nucleotide sequence (i.e. sequence-dependent) or a specific structure. Nucleases may also be characterized by the type of nucleic acid cleaved. For example, deoxyribonucleases cleave DNA and ribonucleases cleave RNA. Typically, nucleases are further divided into endonucleases and exonucleases, although some enzymes may fall in both categories. Endonucleases cleave the phosphodiester bond within a polynucleotide chain, in contrast to exonucleases, which cleave phosphodiester bonds at the end of a polynucleotide chain. Types of nucleases are well-known in the art. For example, endonucleases may include, but are not limited to, DNase I, DNase X, Dnase 1 like 2, DNase gamma, DNase 2alpha, DNase 2beta, L-DNase 2, endonuclease G (EndoG), caspase-activated DNase (CAD), bacterial and fungal nucleases, restriction enzymes, UvrABC, flap endonuclease-1 (FEN1), RNase III, RNase H, RNase P, RNase A, RNase T1, and RNA-induced silencing complex (RISC). Non-limiting examples of exonucleases include TREX1, RecBCD and oligonucleotidase. In some embodiments, cleavage is enzymatic and the enzyme is a ribonuclease. In other embodiments, cleavage is enzymatic and the enzyme is a deoxyribonuclease. In different embodiments, cleavage is enzymatic and the enzyme is an exonuclease. In alternative embodiments, cleavage is enzymatic and the enzyme is an endonuclease. In exemplary embodiments, cleavage is enzymatic and the enzyme is DNase I.

While cleavage is enzymatic or nonenzymatic in preferred embodiments, the Applicants have also contemplated other embodiments where the fluorophores are separated or forced apart via the activity of a helicase, a topoisomerase, or other methods that cause the dissociation of the complementary regions of the nucleotide probe.

One skilled in the art will appreciate that a nucleic acid must contain a nucleotide sequence the nuclease recognizes (i.e. recognition site) for sequence-dependent cleavage to occur. Recognition sites for site-specific nucleases are well known in the art. For example, DNAse I cleaves DNA preferentially at phosphodiester linkages adjacent to a pyrimidine nucleotide. Through the incorporation of one or more copies of a particular recognition site in a nucleotide polymer of the invention, a nucleic acid probe can be designed that is sensitive to and specific for a particular nuclease. Alternatively, a nucleic acid probe can be designed that is sensitive to and specific for at least two nucleases by incorporating one or more copies of at least two different recognition sites in a nucleotide polymer of the invention. In some embodiments, a nucleotide polymer of the invention comprises at least one copy of a single recognition site. In a preferred embodiment, a nucleotide polymer of the invention comprises at least one copy of a recognition site for DNase I. In other embodiments, a nucleotide polymer of the invention comprises at two copies of a single recognition site. In still other embodiments, a nucleotide polymer of the invention comprises at least one copy of at least two recognition sites.

Similarly a nucleic acid must contain a nucleotide sequence that forms a primary structure recognized by a specific nuclease for structure-dependent cleavage to occur. Primary structures recognized by structure-dependent nucleases are well known in the art. For example, flap endonucleases recognize a DNA duplex that has a single-stranded 5' overhang on one of the strands, and catalyze the hydrolytic cleavage of the phosphodiester bond at the junction of the single- and double-stranded DNA. Thus, through the incorporation of a specific nucleotide sequence, DNA probes of different primary structures may be designed.

(c) Fluorophore

According to the invention, a nucleic acid probe encompasses one or more fluorophores. As stated above, quenching refers to loss of fluorescence signal due to short-range interactions between a fluorophore and the local molecular environment. Many environmental factors will exert influences on the fluorescent properties of a fluorophore. For example, interactions between two adjacent fluorophores or between a fluorophore and other species in the surrounding environment can produce environment-sensitive fluorescence.

In certain embodiments, a nucleic acid probe comprises two or more fluorophores. In these embodiments, quenching refers to loss of fluorescence signal due to short-range interactions between fluorophores. A skilled artisan will appreciate that quenching may occur between any two fluorophores in close proximity as long as the emission spectrum of the first fluorophore (donor fluorophore) is similar to or overlaps with the excitation spectrum of the second fluorophore (acceptor fluorophore). In some embodiments, the donor and acceptor fluorophore are the same. In other embodiments, the donor and acceptor fluorophore are different. Suitable fluorophores are well-known in the art, and the choice of the fluorophore may be based on the intended application. For example, near infrared fluorophores (NIRF) are ideally suited for in vivo applications, while both NIRF and non-NIRF may be suitable for in vitro applications. In some embodiments, a fluorophore is a fluorescent probe with excitation and emission wavelengths outside the near infrared spectrum. Non limiting examples include FITC, TRITC, PE, Cy3, and TR. In other embodiments, a fluorophore is a fluorescent probe with excitation and emission wavelengths in the near infrared spectrum (i.e., 650-1300 nm). Use of this portion of the electromagnetic spectrum is advantageous, as tissue penetration is maximal and absorption by physiologically abundant absorbers, such as hemoglobin (<650 nm) and water (>1200 nm), is minimal. Suitable near infrared fluorophores are known in the art, and many are commercially available. Non-limiting examples include Cy5.5, Cy5, Cy-7, IRD's including IRD41, IRD700 and analogs thereof, near infrared AlexaFluor dyes, including but not limited to AlexaFluor 647, AlexaFluor 660, and AlexaFluor 700, NIR-1, LaJolla Blue, indocyanine green (ICG) and analogs thereof, indotricarbocyanine (ITC), and chelated lanthanide compounds that display near infrared fluorescence. In exemplary embodiments, the fluorophore is Cy5.5.

In other embodiments, a nucleic acid probe comprises one or more fluorophores and at least one species that is not a fluorophore and is capable of quenching the one or more fluorophores. Suitable species are well known in the art, and include, but are not limited to, chemical quenchers, paramagnetic species, and heavy atoms. Methods for attaching these species to a nucleic acid are also well known in the art.

In one aspect of the invention, a nucleic acid probe encompasses one or more fluorophores. At a minimum, one fluorophore is required. For example, a probe may comprise 1, 2, 3, 4, or 5 fluorophores. In some exemplary embodiments, a nucleic acid probe comprises one fluorophore. In other exemplary embodiments, a nucleic acid probe comprises two fluorophores. In different exemplary embodiments, a nucleic acid probe comprises at least one fluorophore. In still other exemplary embodiments, a nucleic acid probe comprises at least two fluorophores.

The number of fluorophores per nucleic acid will depend in part on the design of the nucleic acid probe. For example, the totality of fluorophores will be attached to a single nucleotide polymer if a nucleic acid probe of the invention comprises a single nucleotide polymer. Conversely, the totality of fluorophores will be divided among the total number of nucleotide polymers if the nucleic acid probe of the invention comprises two or more nucleotide polymers. In some embodiments, at least one fluorophore is attached to a nucleic acid. In other embodiments, at least two fluorophores are attached to a nucleic acid.

Typically, a fluorophore is attached directly to a nucleotide polymer using any suitable reactive group on the fluorophore and a compatible functional group on the nucleotide polymer. Alternatively, a fluorophore can be indirectly attached to a nucleotide polymer via a linker. Methods of attaching a fluorophore to a nucleotide polymer of the invention are known in the art. Non-limiting examples of linkers include a polysaccharide, a peptide, and a synthetic moiety.

In some embodiments, a fluorophore is attached to the 5'-end of a nucleic acid. In other embodiments, a fluorophore is attached to the 3'-end of a nucleic acid. In still other embodiments, a fluorophore is attached to the 5'-end and the 3'-end of a nucleic acid. In alternative embodiments, a fluorophore is attached to an internal nucleotide in a nucleic acid. Methods of attaching a fluorophore to a nucleotide polymer are well-known in the art.

(d) Optional Modifications

In another aspect of the invention, a nucleic acid probe may be further modified for a particular use. For examples, a nucleic acid probe of the invention may be modified to increase the usefulness for in vivo applications (e.g. increase in vivo half-life or target a nucleic acid probe to a particular location). Alternatively, a nucleic acid probe of the invention may be modified to increase the usefulness for in vitro applications. One of skill in the art will appreciated that a nucleic acid probe can be modified by any number of things, provided the modification does not significantly reduce the ability of the probe to detect nucleic acid cleavage.

In some embodiments, a nucleic acid probe of the invention may be immobilized on a solid support. Non-limiting examples of suitable solid supports include microtitre plates, test tubes, beads, resins and other polymers, as well as other surfaces either known in the art. The solid support may be a material that may be modified to contain discrete individual sites appropriate for attachment or association of the nucleic acid probe and is amendable to at least one detection method. Non-limiting examples of solid support materials may include glass, modified or functional glass, plastics (including acrylics, polysterene, polybutylene, polyurethanes, TeflonJ, etc), nylon or nitrocellulose, polysaccharides, resins, silica or silica-based materials including silicon and modified silicon, carbon, metals, inorganic glasses. A solid support may be planar, a solid support may be a well (i.e. a 384 well plate), or, alternatively, a solid support may be a bead or a slide. Methods of immobilizing a nucleic acid probe of the invention to a solid support are known in the art. For example, a nucleic acid probe may be conjugated to a protein or a label, wherein either the protein or the label stably interacts with the solid support, such that the nucleic acid probe is immobilized. In some embodiments, a nucleic acid may be conjugated to a protein. In an exemplary embodiment, the protein is an antibody. In other embodiments, a nucleic acid probe may be conjugated to a label. Non-limiting examples of labels include biotin In other embodiments, a nucleic acid probe of the invention may be packaged in or on a vesicle. Non-limiting types of vesicles may include liposomes, micelles, reverse micelles, and nanoparticles/nanomaterials. As detailed in the Examples, packing the nucleic acid probe AB259.3 in cationic liposomes altered the bioavailability of the probe. In an exemplary embodiment, a nucleic acid probe is packaged in a liposome. In another exemplary embodiment, a nucleic acid probe is packaged in a nanoparticle.

(e) Formulations

In another aspect of the invention, a composition comprising a nucleic acid probe may be formulated for a particular use.

In one embodiment, a nucleic acid probe of the invention may be formulated for administration to a subject. For instance, a nucleic acid probe may be manufactured in dosage unit formulations containing conventional nontoxic pharmaceutically acceptable adjuvants, carriers, excipients, and vehicles as desired. Formulation of pharmaceutical compositions is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980). Such formulations can be administered orally, parenterally, by inhalation spray, rectally, intradermally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques.

(f) Preferred Embodiments

In a preferred embodiment, a nucleic acid probe of the invention comprises two components: A1-A2-A3 and A5-A6-A7, linked by a third component, A4, whereby A1 is Cy5.5, A2 is adenine (A), A3 is the nucleic acid sequence ACACTC, A4 is the nucleic acid sequence CGAT, A5 is the nucleic acid sequence GAGTGT, A6 is adenine (A), and A7 is Cy5.5, whereby A1 and A7 are positioned relative to each other such that they quench each other's fluorescence when A3 associates with A5, and A6 is not cleaved by DNase I.

In another preferred embodiment, a nucleic acid probe of the invention comprises two components: A1-A2-A3 and A5-A6-A7, linked by a third component, A4, whereby A1 is Cy5.5, A2 is adenine (A), A3 is the nucleic acid sequence ACACTC, A4 is the nucleic acid sequence CGAT, A5 is the nucleic acid sequence GAGTGT, A6 is the nucleic acid sequence AGAATGT, and A7 is Cy5.5, whereby A1 and A7 are positioned relative to each other such that they quench each other's fluorescence when A3 associates with A5, and A6 is not cleaved by DNase I.

In a different preferred embodiment, a nucleic acid probe of the invention comprises two components: A1-A2-A3 and A5-A6-A7, linked by a third component, A4, whereby A1 is Cy5.5, A2 is adenine (A), A3 is the nucleic acid sequence ACACTC, A4 is the nucleic acid sequence CGAT, A5 is the nucleic acid sequence GAGTG, A6 is the nucleic acid sequence AGAATGTACGAGT (SEQ ID NO: 6), and A7 is Cy5.5, whereby A1 and A7 are positioned relative to each other such that they quench each other's fluorescence when A3 associates with A5, and A6 is not cleaved by DNase I.

In yet another preferred embodiment, a nucleic acid probe of the invention comprises two components: A1-A2-A3 and A5-A6-A7, whereby A1 is Cy5.5, A2 is adenine (A), A3 is the nucleic acid sequence ACACTC, A5 is the nucleic acid sequence GAGTGT, A6 is the nucleic acid sequence AGAATGT, and A7 is Cy5.5, whereby A1 and A7 are positioned relative to each other such that they quench each other's fluorescence when A3 associates with A5, and A6 is not cleaved by DNase I.

II. Methods of Use

Another aspect of the present invention is a method for detecting enzymatic or non-enzymatic nucleic acid cleavage. Advantageously, nucleic acid cleavage may be detected in a sample or in a subject. Said another way, a method of the invention allows for the detection of nucleic acid cleavage in vitro, ex vivo, in vivo, and in situ. As a result, a method of the invention has applications for high throughput screening, diagnostic imaging and assays, and disease modeling.

Generally speaking, a method of the invention comprises contacting a sample with, or administering to a subject, a nucleic acid probe that fluoresces when cleaved and detecting the fluorescence in the sample or the subject. A nucleic acid probe that fluoresces when cleaved may be as described in Section I. In preferred embodiments, a nucleic acid probe comprises two components, A1-A2-A3 and A5-A6-A7, and optionally a third component, A4. A1 is a first fluorophore. A2 is a single-stranded nucleic acid that is not complementary to A3, A5, or A6, and optionally comprises a nuclease recognition sequence. In certain preferred embodiments, A2 is about 1 to about 50 nucleotides long. In other preferred embodiments, A2 is about 1 to about 10 nucleotides long. In still other preferred embodiments, A2 is about 4 to about 10 nucleotides long. A3 is a single-stranded nucleic acid that is complementary to A5. In some preferred embodiments, A3 is about 2 to about 80 nucleotides long. In other preferred embodiments, A3 is about 5 to about 25 nucleotides long. A4 is a single-stranded nucleic acid that, when present, connects and forms a loop structure between A3 and A5. In certain preferred embodiments, A4 is about 4 nucleotides to about 50 nucleotides long. In other preferred embodiments, A4 if about 4 to about 30 nucleotides long. In different preferred embodiments, A4 is about 4 to about 10 nucleotides long. A5 is a single-stranded nucleic acid that is complementary to A3. In some preferred embodiments, A5 is about 2 to about 80 nucleotides long. In other preferred embodiments, A5 is about 5 to about 25 nucleotides long. A6 is a single-stranded nucleic acid that is not complementary to A2, A3 or A5, and optionally comprises a nuclease recognition sequence. In some preferred embodiments, A6 is about 1 to about 50 nucleotides long. In other embodiments, A6 is about 1 to about 10 nucleotides long. In still preferred other embodiments, A6 is about 4 to about 10 nucleotides long. A7 is a second fluorophore. The nucleic acid probe's structure (i) positions A1 and A7 relative to each other such that they quench each other's fluorescence when A3 associates with A5, and A1-A2-A3 or A5-A6-A7 are not cleaved; and (ii) can be cleaved by enzymatic or non-enzymatic means if present in a sample, causing the fluorophores on the nucleic acid probe to dissociate and emit fluorescence.

In an exemplary embodiment, the nucleic acid probe is the AB259.3 DNA probe described in the Examples, wherein the DNA probe comprises two components: A1-A2-A3 and A5-A6-A7, linked by a third component, A4, whereby A1 is Cy5.5, A2 is A, A3 is ACACTC, A4 is CGAT, A5 is GAGTGT, A6 is AGAATGT, and A7 is Cy5.5, and whereby A1 and A7 are positioned relative to each other such that they quench each other's fluorescence when A3 associates with A5, and A6 is not cleaved by DNase I.

(a) Enzymatic and Non-Enzymatic Cleavage

In one aspect, a method of the invention encompasses detecting enzymatic or non-enzymatic cleavage. Types of enzymatic and non-enzymatic cleavage that may be detected by the method of the invention are described above in Section Ib. In exemplary embodiments, a method of invention detects enzymatic cleavage and the enzyme is a deoxyribonuclease. In other exemplary embodiments, a method of invention detects enzymatic cleavage and the enzyme is a ribonuclease. In a preferred embodiment, a method of invention detects enzymatic cleavage and the enzyme is DNase I. In another preferred embodiment, a method of invention detects non-enzymatic cleavage caused by reactive oxygen species. In another preferred embodiment, a method of invention detects non-enzymatic cleavage caused by exposure to radiation.

According to the invention, fluorescence is detectable when the complementary regions of the nucleic acid probe disassociate as a result of nucleic acid cleavage. Stated another way, fluorescence indicates nucleic acid cleavage of at least one component of the nucleic acid probe. A change or a fold-increase in fluorescence may calculated by comparing fluorescence measured in a sample compared to a control. Suitable controls are known in the art and may include, but are not limited to, samples without a nuclease, buffer only, sham treated, samples without a probe. In some embodiments, fluorescence will increase at least 2-fold upon nucleic acid cleavage. For example, fluorescence may increase at least 2-fold, at least 3-fold, at least 4-fold, at least 5-fold, at least 6-fold, at least 7-fold, at least 8-fold, at least 9-fold, or at least 10-fold upon nucleic acid cleavage. In other embodiments, fluorescence will increase at least 5% upon nucleic acid cleavage. For example, fluorescence may increase at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% upon nucleic acid cleavage. In other embodiments, fluorescence will increase at least 100% upon nucleic acid cleavage. For example, fluorescence may increase at least 110%, at least 120%, at least 130%, at least 140%, at least 150%, at least 160%, at least 170%, at least 180%, at least 190%, at least 200%, at least 210%, at least 220%, at least 230%, at least 240%, at least 250%, at least 260%, at least 270%, at least 280%, at least 290%, at least 300%, at least 310%, at least 320%, at least 330%, at least 340%, at least 350%, at least 360%, at least 370%, at least 380%, at least 390%, at least 400%, at least 410%, at least 420%, at least 430%, at least 440%, at least 450%, at least 460%, at least 470%, at least 480%, at least 490%, or at least 500% upon nucleic acid cleavage.

Fluorescence may also be reported is radiant efficiency. In some embodiments, radiant efficiency will increase at least 2-fold upon nucleic acid cleavage. For example, radiant efficiency may increase at least 2-fold, at least 3-fold, at least 4-fold, at least 5-fold, at least 6-fold, at least 7-fold, at least 8-fold, at least 9-fold, or at least 10-fold upon nucleic acid cleavage. In other embodiments, radiant efficiency will increase at least 5% upon nucleic acid cleavage. For example, radiant efficiency may increase at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% upon nucleic acid cleavage. In other embodiments, radiant efficiency will increase at least 100% upon nucleic acid cleavage. For example, radiant efficiency may increase at least 110%, at least 120%, at least 130%, at least 140%, at least 150%, at least 160%, at least 170%, at least 180%, at least 190%, at least 200%, at least 210%, at least 220%, at least 230%, at least 240%, at least 250%, at least 260%, at least 270%, at least 280%, at least 290%, at least 300%, at least 310%, at least 320%, at least 330%, at least 340%, at least 350%, at least 360%, at least 370%, at least 380%, at least 390%, at least 400%, at least 410%, at least 420%, at least 430%, at least 440%, at least 450%, at least 460%, at least 470%, at least 480%, at least 490%, or at least 500% upon nucleic acid cleavage. A skilled artisan will appreciate that radiant efficiency is one type of unit that may be used to report fluorescence, and that other suitable units may also be used.

(b) Samples

In another aspect, a method of the invention encompasses contacting a nucleic acid probe with a sample. Suitable samples include, but are not limited to, a cell, cell lysate, a protein sample, tissue, homogenized tissue, organ, homogenized organ, and bodily fluid. As will be appreciated by a skilled artisan, the method of collecting and preparing a sample from a subject can and will vary depending upon the nature of the sample. Any of a variety of methods generally known in the art may be utilized to collect a sample. Generally speaking, the method preferably maintains the integrity of the nucleic acid cleavage activity such that it can accurately be detected and/or quantified in the sample.

In some embodiments, a sample is a cell. A cell, for example, may be an immortalized cell or a primary cell isolate. Immortalized cell lines are commercially available, and methods for collecting primary cell isolates are known in the art. The cell may be cultured in vitro using standard cell culture techniques. One skilled in the art will appreciate that any known cell type that can be cultured in vitro, even for a limited time, may be used in the method of the invention. Methods for introducing a nucleic acid probe are also known in the art and detailed in the Examples. In some embodiments, the cell is a primary cell. In other embodiments the cell is an immortalized cell. In exemplary embodiments, the cell is an immortalized kidney cell. Non-limiting examples of kidney cells include NRK-52E, NRK-49F, TKPTS, primary renal tubular epithelial cells, primary renal mesangial cells, HEK-293, HK-2, VERO cells, and COS-7. In other exemplary embodiments, the cell is vascular smooth muscle cell. In still other exemplary embodiments, the cell is a vascular endothelial cell. In different exemplary embodiments, the cell is a prostate cancer. In alternative exemplary embodiments, the cell is a breast cancer cell.

In other embodiments, a sample is cell lysate. It may be advantageous to detect and optionally quantify fluorescence in a cell lysate rather than a whole cell. Cell lysate may be prepared by homogenizing a culture of cells according to any of the methods known in the art. A nucleic acid probe may then be added to the cell lysate, the suspension mixed, and fluorescence detected. Conversely, cells may be homogenized after a nucleic acid probe has been introduced, as described above.

In different embodiments, a sample is a protein sample. A protein sample may be a liquid, dry or frozen sample comprising a nuclease. The nuclease may be the only protein component in the sample, the predominant protein component in the sample, or one of many protein components in the sample. There may also be other components in the sample. For example, buffers, protein stabilizers, and natural or synthetic compounds. In a preferred embodiment, the protein sample comprises DNase I. If the sample is a dry (e.g. powder or flakes), it must first be reconstituted in the appropriate buffer. If the sample is frozen, it must first be thawed. A nucleic acid probe may then be added to the protein sample, the sample mixed, and fluorescence detected. In a preferred embodiment, the protein sample comprises a recombinant nuclease. In another preferred embodiment, the protein sample comprises a purified nuclease.

In still other embodiments, a sample is tissue or organ. Non-limiting examples of suitable tissues includes connective tissue, muscle tissue, nervous tissue, and epithelial tissue. Non-limiting examples of suitable organs include organs of the cardiovascular system, digestive system, the endocrine system, the excretory system, the immune system, the nervous system, the reproductive system, the respiratory system. In an exemplary embodiment, the organ is selected from the group consisting of kidney, liver, pancreas, heart, and brain. Tissue and organ samples may be cultured in vitro or ex vivo. They may also be biopsy samples or otherwise removed from a subject. Methods for introducing a nucleic acid probe into a tissue or organ are known in the art and detailed in the Examples. In a preferred embodiment, the sample is a biopsy taken from a subject. Suitable subjects are described in more detail below in Section IIc.

In different embodiments, a sample is homogenized tissue or homogenized organ. It may be advantageous to detect and optionally quantify fluorescence in a homogenate rather than a whole tissue or whole organ. Homogenized tissue or homogenized organ physically breaking apart a tissue or organ sample in a liquid into small particles according to any of the methods known in the art. The particulate matter may then be separated from the liquid, and the liquid may then be mixed with nucleic acid probe and fluorescence detected. Conversely, tissue or organ may be homogenized after a nucleic acid probe has been introduced, as described above.

In alternative embodiments, a sample is bodily fluid. Non-limiting examples of bodily fluids include blood, plasma, serum, sweat, tears, saliva, sputum, urine, feces, amniotic fluid, breast milk, pancreatic secretion, bile, vaginal secretion, lymph, cerebrospinal fluid and sperm. Methods for collecting bodily fluids are well-known in the art. In a preferred embodiment, the bodily fluid is blood. In another preferred embodiment, the bodily fluid is urine. In another preferred embodiment, the bodily fluid is serum. In another preferred embodiment, the bodily fluid is pancreatic secretions.

i. Suitable Amount

A suitable amount of the nucleic acid probe should be used. Though the amount can and will vary depending on several factors (for example, number of fluorophores on the probe, type of sample, type of detection method, etc.), a suitable may be determined by routine experimentation.

ii. Detecting Fluorescence in a Sample

Methods of detecting, and optionally quantifying, fluorescence in a sample are well known in the art. Generally, filtered light or a laser with a defined bandwidth is used as a source of excitation light. The excitation light travels through the sample. When it encounters a fluorophore, the excitation light is absorbed. The fluorescent molecule then emits light (fluorescence) spectrally distinguishable (slightly longer wavelength) from the excitation light. The fluorescence may then be detected, and optionally quantified, by a fluorescence detection system. Non-limiting examples of suitable fluorescence detection systems include spectrofluorometers and microplate readers, fluorescence microscopes, fluorescence scanners, and flow cytometers. The choice of the detection system may depend in part on the type of sample.

(c) Subjects

In another aspect, a method of the invention provides that a nucleic acid probe is administered to a subject. Suitable subjects include, but are not limited to, rodents, livestock animals, zoological animals, companion animals and humans. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a different embodiment, the subject may be a human. In a preferred embodiment, the subject is a laboratory animal. Non-limiting examples of a laboratory animal may include rodents, canines, felines, and non-human primates. In another preferred embodiment, the subject is a human.

The subject may or may not have been diagnosed with a disease or a condition associated with changes in nuclease activity. The contribution nucleases make to health, and their role in disease, have been reported. See, for example, Bailey et al. 2012 *DNA Repair*, Widlak et al. 2009 Cell Mol Life Sci, and Zheng et al. 2010 Nucleic Acid Res. "Changes", as used herein, refers to both increases and decreases in nuclease activity compared to either an average nuclease activity in a reference or control population (e.g. healthy subjects) or a measurement of nuclease activity in the same subject at an earlier time. In some embodiments, the subject has no clinical signs or symptoms of disease. In other embodiments, the subject has clinical signs of disease. In yet other embodiments, the subject may be at risk for disease. In still other embodiments, the subject has been diagnosed with disease. Methods to diagnose disease are known in the art.

In some embodiments, the subject has increased levels of nuclease activity. For example, the subject may have a disease or genetic mutation resulting in increased nuclease activity. Non-limiting examples of diseases or conditions associated with increased nuclease activity include kidney disease, pancreatic disease, heart disease, brain disease, high testosterone, acute tissue trauma, acute organ trauma, organ failure, kidney, liver, brain or heart toxicity or ischemic injury, metabolic and infectious disease, including, bacteriemia, sepsis and inflammation. In an exemplary embodiment, the subject has kidney disease. Non-limiting examples of kidney diseases include toxic or ischemic kidney failure (i.e. end stage renal disease), acute or chronic kidney allograft rejection, chronic kidney disease, polycystic kidney disease, and nephritis. In other embodiments, the subject was exposed to full or partial body irradiation resulting in increased nuclease activity.

In some embodiments, the subject has decreased levels of nuclease activity. For example, the subject may have a disease or genetic mutation resulting in decreased nuclease activity. Non-limiting examples of diseases or conditions associated with decreased DNase I include autoimmune diseases, cancers (including chemical- or radiation-induced carcinogenesis), metabolic syndromes, cystic fibrosis and cardiac hypertrophy. Non-limiting examples of genetic mutations resulting in decreased nuclease activity include mutation of Rad50:Mre11:Xrs2 complex and R114H mutation in TREX1. Other examples may include hereditary DNA repair disorders and aging disorders. Non-limiting examples of DNA repair disorders include xeroderma pigmentosum and ataxia-teleangiectasia. Non-limiting examples of aging disorders include progeria and Werner's syndrome. In certain exemplary embodiments, a subject has tumor. In other exemplary embodiments, a subject has an autoimmune disease. In a preferred embodiment, the subject has systemic lupus erythematosus.

i. Administering to a Subject

A composition of the invention may be formulated and administered to a subject by several different means. Methods for formulating a composition of the invention are described in Section Ie. A composition may generally be administered parenteraly, intraperitoneally, intravascularly, or intrapulmonarily in dosage unit formulations containing conventional nontoxic pharmaceutically acceptable adjuvants, carriers, excipients, and vehicles as desired. The term parenteral as used herein includes subcutaneous, intravenous, intramuscular, intrathecal, or intrasternal injection, or infusion techniques.

A suitable amount of the nucleic acid probe should be administered to a subject. Though the amount can and will vary depending on several factors (for example, number of fluorophores on the probe, type of subject, type of detection method, etc.), a suitable may be determined by experimentation.

ii. Detecting Fluorescence in a Subject

Methods of detecting, and optionally quantifying, fluorescence, and specifically fluorescent probes, in a subject are well known in the art. For example, see U.S. Pat. No. 6,083,486, U.S. Pat. No. 6,592,847 and US 20060275775, incorporated by reference herein. Suitable methods are also detailed in the Examples. Typically, fluorescence is detected by performing a signal acquisition scan on the subject and processing the data from the signal acquisition to generate data and form an image of the subject, wherein the data is a read-out of the fluorescence emitted by fluorophores. As an optional step, the fluorescence may be quantified and the amount of quantified fluorescence may be compared to control group of healthy subjects, wherein an increased or decreased level of fluorescence indicates a disease state.

(d) Preferred Embodiments

In a preferred embodiment, a method of the invention comprises detecting nucleic acid cleavage by DNase I in a sample, the method comprising (i) contacting the sample with a deoxyribonucleic acid probe comprising two components, A1-A2-A3 and A5-A6-A7, and optionally a third component, A4; wherein, A1 is a first near-infra red fluorophore, A2 is a single-stranded deoxyribonucleic acid that is about 1 to about 10 nucleotides long and optionally comprises a nuclease recognition sequence, A3 is a single-stranded deoxyribonucleic acid that is complementary to A5 and is about 2 to about 25 nucleotides, A4 is a single-stranded deoxyribonucleic acid comprising about 4 nucleotides to about 10 nucleotides that, when present, connects and forms a loop structure between A3 and A5, A5 is a single-stranded deoxyribonucleic acid that is complementary to A3 and is about 2 to about 25 nucleotides, A6 is a single-stranded deoxyribonucleic acid comprising about 1 to about 10 nucleotides that optionally comprises a nuclease recognition sequence, and A7 is a second near-infra red fluorophore; whereby, A1 and A7 are positioned relative to each other such that they quench each other's fluorescence when A3 associates with A5, and A1-A2-A3 or A5-A6-A7 are not cleaved; such that contacting the sample with the deoxyribonucleic acid probe allows for the probe to be cleaved by DNase I if present in the sample, causing the fluorophores on the deoxyribonucleic acid probe to dissociate; and (if) quantifying the fluorescence in the sample, wherein fluorescence in a sample indicates deoxyribonucleic acid cleavage by DNase I. In exemplary embodiments, the sample is selected from the group consisting of a cell, cell lysate, a protein sample, tissue, homogenized tissue, an organ, homogenized organ, and bodily fluid.

In a preferred embodiment, a method of the invention comprises detecting nucleic acid cleavage by reactive oxygen species in a sample, the method comprising (i) contacting the sample with a deoxyribonucleic acid probe comprising two components, A1-A2-A3 and A5-A6-A7, and optionally a third component, A4; wherein, A1 is a first near-infra red fluorophore, A2 is a single-stranded deoxyribonucleic acid that is about 1 to about 10 nucleotides long that optionally comprises a nuclease recognition site, A3 is a single-stranded deoxyribonucleic acid that is complementary to A5 and is about 2 to about 25 nucleotides, A4 is a single-stranded deoxyribonucleic acid comprising about 4 nucleotides to about 10 nucleotides that, when present, connects and forms a loop structure between A3 and A5, A5 is a single-stranded deoxyribonucleic acid that is complementary to A3 and is about 2 to about 25 nucleotides, A6 is a single-stranded deoxyribonucleic acid comprising about 1 to about 10 nucleotides that optionally comprises a nuclease recognition sequence, and A7 is a second near-infra red fluorophore; whereby, A1 and A7 are positioned relative to each other such that they quench each other's fluorescence when A3 associates with A5, and A1-A2-A3 and A5-A6-A7 are not cleaved; such that contacting the sample with the deoxyribonucleic acid probe allows for the probe to be cleaved by reactive oxygen species if present in the sample, causing the fluorophores on the deoxyribonucleic acid probe to dissociate; and (ii) quantifying the fluorescence in the sample, wherein fluorescence in a sample indicates deoxyribonucleic acid cleavage by reactive oxygen species. In exemplary embodiments, the sample is selected from the group consisting of a cell, cell lysate, a protein sample, tissue, homogenized tissue, an organ, homogenized organ, and bodily fluid.

In another preferred embodiment, a method of the invention comprises imaging nucleic acid cleavage by DNase I in a subject, the method comprising (i) contacting the sample with a deoxyribonucleic acid probe comprising two components, A1-A2-A3 and A5-A6-A7, and optionally a third component, A4; wherein, A1 is a first near-infra red fluorophore, A2 is a single-stranded deoxyribonucleic acid that is about 1 to about 10 nucleotides long that optionally comprises a nuclease recognition sequence, A3 is a single-stranded deoxyribonucleic acid that is complementary to A5 and is about 2 to about 25 nucleotides, A4 is a single-stranded deoxyribonucleic acid comprising about 4 nucleotides to about 10 nucleotides that, when present, connects and forms a loop structure between A3 and A5, A5 is a single-stranded deoxyribonucleic acid that is complementary to A3 and is about 2 to about 25 nucleotides, A6 is a single-stranded deoxyribonucleic acid comprising about 1 to about 10 nucleotides that optionally comprises a nuclease recognition sequence, and A7 is a second near-infra red fluorophore; whereby, A1 and A7 are positioned relative to each other such that they quench each other's fluorescence when A3 associates with A5, and A1-A2-A3 and A5-A6-A7 are not cleaved; such that contacting the sample with the deoxyribonucleic acid probe allows for the probe to be cleaved by DNase I if present in the sample, causing the fluorophores on the deoxyribonucleic acid probe to dissociate; and (ii) performing a signal acquisition scan on the subject; and (iii) processing the data from the signal acquisition to generate data and form an image of the subject, wherein the data is a read-out of the fluorescence emitted by the fluorochromes of the cleaved nucleic acid probes in a subject. In exemplary embodiments, the subject is selected from the group consisting of a human, a rodent and a non-human primate.

In another preferred embodiment, a method of the invention comprises detecting nucleic acid cleavage by reactive oxygen species in a subject, the method comprising (i) contacting the sample with a deoxyribonucleic acid probe comprising two components, A1-A2-A3 and A5-A6-A7, and optionally a third component, A4; wherein, A1 is a first near-infra red fluorophore, A2 is a single-stranded deoxyribonucleic acid that is about 1 to about 10 nucleotides long that optionally comprises a nuclease recognition sequence, A3 is a single-stranded deoxyribonucleic acid that is complementary to A5 and is about 2 to about 25 nucleotides, A4 is a single-stranded deoxyribonucleic acid comprising about 4 nucleotides to about 10 nucleotides that, when present, connects and forms a loop structure between A3 and A5, A5 is a single-stranded deoxyribonucleic acid that is complementary to A3 and is about 2 to about 25 nucleotides, A6 is a single-stranded deoxyribonucleic acid comprising about 1 to about 10 nucleotides that optionally comprises a nuclease recognition sequence, and A7 is a second near-infra red fluorophore; whereby, A1 and A7 are positioned relative to each other such that they quench each other's fluorescence when A3 associates with A5, and A1-A2-A3 and A5-A6-A7 are not cleaved; such that contacting the sample with the deoxyribonucleic acid probe allows for the probe to be cleaved by reactive oxygen species if present in the sample, causing the fluorophores on the deoxyribonucleic acid probe to dissociate; and (ii) performing a signal acquisition scan on the subject; and (iii) processing the data from the signal acquisition to generate data and form an image of the subject, wherein the data is a read-out of the fluorescence emitted by the fluorochromes of the cleaved nucleic acid probes in a subject. In exemplary embodiments, the subject is selected from the group consisting of a human, a rodent and a non-human primate.

EXAMPLES

The following examples illustrate various iterations of the invention.

Introduction

Chromosomal DNA is the largest molecule in the cell. Its disposal is achieved by enzymatic fragmentation. DNA fragmentation occurs immediately prior and, mostly, after cell death, and is considered a hallmark of irreversible cell death of any kind. It is provided by nine enzymes, which can be called cytotoxic endonucleases to distinguish them from DNA repair endonucleases. Cytotoxic endonucleases include eight DNases: DNase I and its three homologs, DNase II and its two homologs, and caspase-activated DNase (CAD), and one nuclease (DNase/RNase), endonuclease G (EndoG) [1-6]. All of the enzymes are coded by single-copy genes, and often synthesized as precursors with weak activity. Mature enzymes resulted from cleavage of signal peptides, share many physicochemical and enzymatic characteristics, and catalyze essentially the same reaction of DNA destruction by hydrolysis of phosphodiester bonds. To some degree, all endonucleases can be found in all cells/tissues, however the spectrum of the activity/expression of individual endonucleases vary widely between the cell types and tissues. In mammals, the most active endonuclease is DNase I [7-10]. It is highly expressed in kidneys, pancreas, salivary glands and intestine. It also seems to be the most active endonuclease in blood, urine, saliva and other body fluids [10]. DNase I and another DNase I-like enzyme, DNase γ, are secreted proteins [7].

The role of endonucleases in normal tissues seems to be limited to removal of DNA from dead cell remnants and body fluids [1, 2]. Despite this important role, with the exception of DNase II [11], an inactivation of a single endonuclease usually does not result in immediate loss of animal or cell viability. However, when the system is stressed by an injury, the difference in viability usually becomes evident [6]. Inactivation of endonuclease in mice protects against cell injury [12, 13] or organ injuries [10, 14] induced by toxic agents and radiation. DNase I deficiency causes lupus-like syndrome in female mice due to insufficient DNA disposal [15]. Deletions and mutation in loci coding endonucleases were described in association with lupus (DNase I) [16], metabolic syndromes (DNase X) [17, 18], cardiac hyperthrophy (EndoG) [19], and chemical- or radiation-induced carcinogenesis (CAD) [20, 21]. Cancer cells and tumors usually have decreased activity of endonucleases [12, 13]. Instead, protein inhibitor of CAD, ICAD, was shown to be overexpressed in various cancers [22-24].

When measured in vitro, endogenous endonuclease activity seems to be excessive and yet harmless under non-injuring conditions. For example, degradation of DNA in isolated cell nuclei, which contain only traces of endonuclease, results in a complete destruction of DNA to oligonucleotides in a matter of minutes [25]. Inappropriate storage of animal tissues results in profound DNA fragmentation detectable by TUNEL [26]. This, however, does not occur in live cells because their DNA is protected against the DNases. The first line of defense against DNases is compartmentalization of the enzymes. While chromosomal DNA is located in nucleus, endonucleases are compartmentalized in mitochondria (EndoG), lysosomes (DNase II), endoplasmic reticulum or cytoplasm (DNase I, DNase γ, CAD). Other defense mechanisms may include several levels of chromatin compactization, protein inhibitors, and suboptimal reaction conditions.

It is important to remember that all the knowledge about activities of endonucleases should be considered hypothetical because it is produced by in vitro studies of activities measured in synthetic solutions or biological fluids, tissue extracts or sections by using "optimal" (by pH, concentration of cofactors and stabilizers) but unnatural conditions. Therefore almost all the information is a subject to re-testing when in vivo methods to measure endonuclease activity become available. It may be expected that in vivo, endonucleases have no activity at all (for example, due to association with yet unknown inhibitors). Furthermore, there may be potentiating, additive and competitive inhibition between several types of endonucleases in vivo that could not be detected in in vitro setting which was optimized for one given endonuclease. Up to this moment, no such methods were available.

Recent developments of fluorescence resonance energy transfer (FRET) method based on infra-red fluorescent (NIRF) probes allowed designing of probes and methods for measurement of proteolytic activities in vivo [27]. In this method, the oligopeptide probe contains two molecule of fluorophores placed at the ends of the peptide in a close proximity that caused quenching of the fluorophores. Proteolytic degradation separates the fluorophore molecules, which results in the increase of the fluorescence. In this case, the use NIRF fluorophores, like Cy5.5, allows visualization of proteolytic activity in vivo and provides minimal background fluorescence.

The goal of the current study was to create a NIRF DNase activity probe and to test it in vitro, ex vivo and in vivo. Creation of such a probe would permit the first in vivo measurement of endonuclease activity. Same probe may be useful in a high throughput in vitro endonuclease assay.

Example 1. Characterization of Near Infra-Red Fluorescent (NIRF) Probes

Preliminary tests using linear single-stranded DNA oligonucleotide probes (6-20 nucleotides) with Cy5.5 fluorophore placed at 5' and 3' ends showed high background fluorescence (data not shown). It was impossible to determine if the background fluorescence was attributed to the probe or it originated from a partial degradation of the probe. Consequently, the NIRF probes were designed as hairpins to allow testing the integrity of DNA by its denaturing followed by reannealing. The use of hairpin also allows easy measurement of the maximum fluorescence of the probe. The distance between two fluorophores varied by changing of protruding DNA strand length from +0 (AB259.1 probe) to +5 (AB259.3 probe) or to +10 (AB259.5 probe) as shown in FIG. 1A. The baseline fluorescence of probe AB259.1 was 30% higher than negative control without a probe (FIG. 1B). AB259.3 and AB259.5 had much higher levels of the baseline fluorescence that correlated with the length of protruded DNA end (or distance between the two Cy5.5 labels).

To ensure the integrity of the DNA probes, it was tested whether a heat denaturing of the hairpins would cause an increase in fluorescence, and if a reannealing would reverse it. To compensate for thermal change of fluorophore's emission, the ROX fluorophore was added to tested probes as an internal reference. The data suggested that AB259.1 and AB259.3 had the best performance and gained fluorescence by 2.7 and 2.8 times, respectively, while AB259.5 probe gained only fluorescence 1.8 times above background (FIG. 1C). After cooling down to 40° C., the fluorescence of all three probes expectedly decreased, but stayed nearly 30% higher than original fluorescence at starting point that reflected perhaps partial change of Cy5.5 molecule or DNA damage that occurred during the thermal impact.

Lastly, the probes' integrity was tested by alkaline denaturing. The probes were treated with alkaline buffer and kinetic detection of the fluorescence was performed. The data suggested that in 5 min, all probes gained fluorescence and reached the plateau (FIG. 10). AB259.1, AB259.3 and AB259.5 gained 40%, 81%, and 85% of fluorescence, respectively. Therefore these data proved the concept that disruption of two fluorescently labeled strands of DNA lead to enhancement of fluorescence.

Example 2. Measurement of Endonuclease Activity with the DNA Probes In Vitro

Figure 2A:
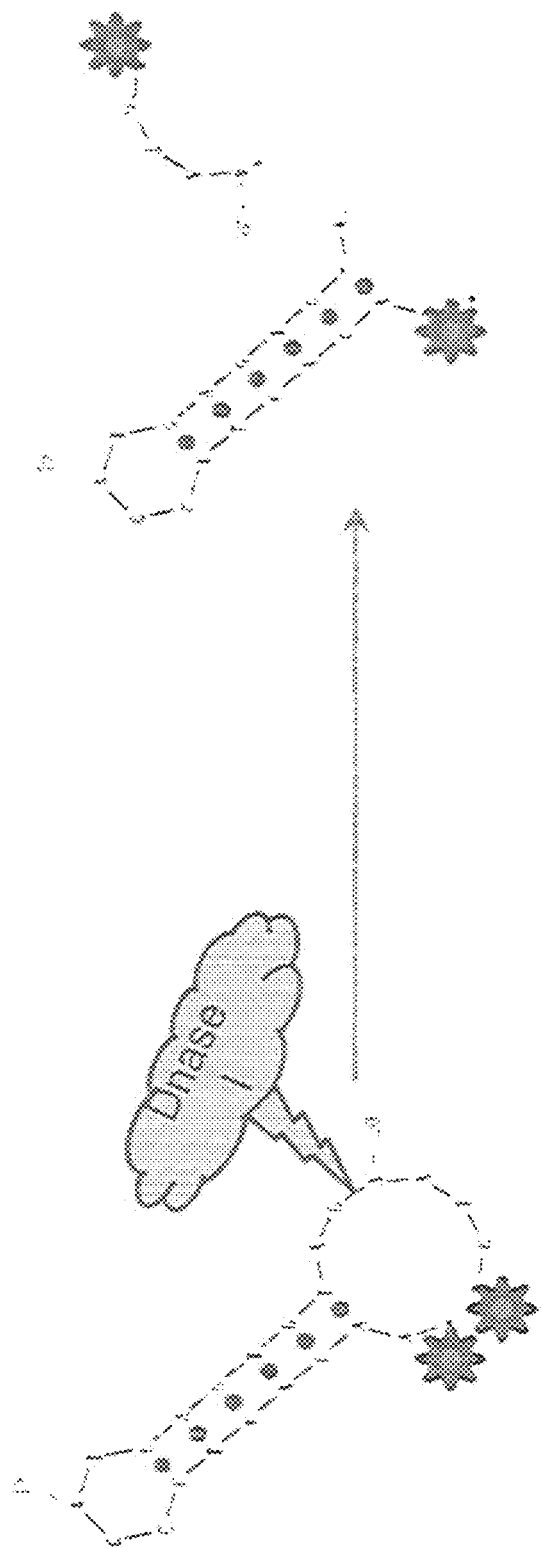
FIG. 2A shows a schematic illustrating the use of a DNA probe with NIRF fluorophores, like Cy5.5, to visualize endonuclease activity. Endonuclease/DNAse I degradation of the representative probe, AB259.3 (SEQ ID NO: 2), cleaves the probe into two pieces, Cy5.5-AACACTCCGATGAGTGTA (SEQ ID NO: 4) and GAATGT-Cy5.5, thereby separating the fluorophore molecules, which results in an increase in fluorescence that can be measured.
Figure 2B:
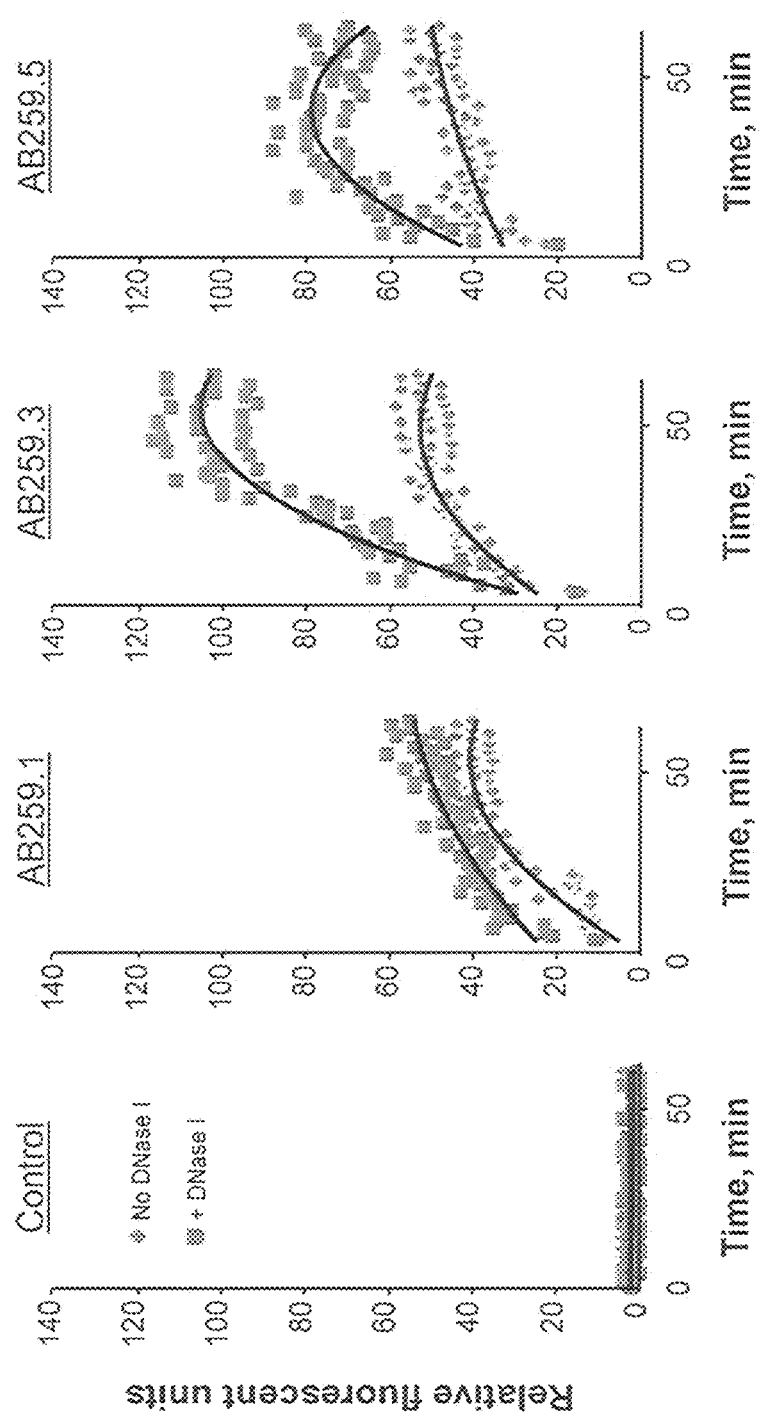
FIG. 2B depicts graphs comparing measurements of DNase I activity using AB259.1, AB259.3 and AB259.5 probes. Fluorescence was measured in the presence (red squares) or absence (blue diamonds) of DNase I. AB259.3 was selected for further characterization, as depicted in FIG. C-D. (C) Measurement of endonuclease activity of DNase I using AB259.3 probe (concentration-dependent response). (D) The AB259.3 assay is sensitive and specific to changes in DNase I endonuclease activity in the presence of DNase I inhibitors. Measurement of endonuclease activity of DNase I using AB259.3 probe in the presence of Ca/Mg ions (EAA buffer; +Ca/Mg), in the absence of Ca/Mg ions (deionized water; No Ca/Mg), in EAA buffer with an ion-chelator (EDTA; +Ca/Mg+EDTA), or Zn-containing inhibitors of endonuclease activity, zinc-diisopropyl salicylate (Zn-DIPS) and zinc chloride (+$ZnCl_2$). *P<0.05 compared to assay with Ca/Mg buffer.
Figure 2:
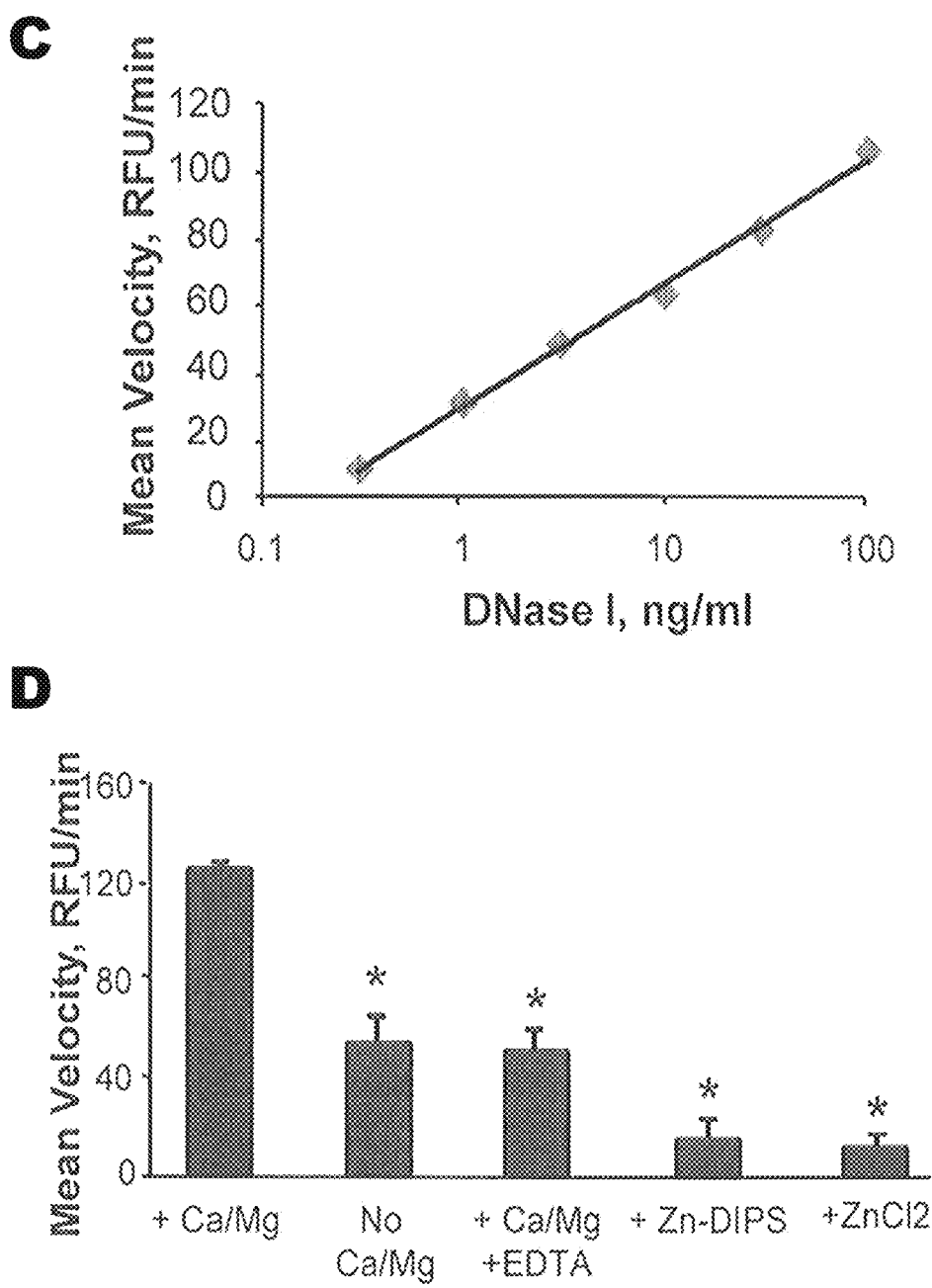

It was hypothesized that exposure of the probes to endonucleases would lead to DNA cleavage and dissociation of protruded strand from the hairpin (FIG. 2A). To assess which of the proposed probes is the best to measure endonuclease activity, the probes (0.5 µM) were exposed with recombinant human DNase I (1 µg/ml) and the kinetic fluorescence curves were recorded. Twenty min into the reaction, AB259.1, AB259.3 and AB259.5 gained 1.75-, 2.6- and 1.62-fold fluorescence, respectively, compared to the baseline (FIG. 2B). At 20-25 min, AB259.1 and AB259.3 reached the plateaus. Surprisingly, by that time, fluorescence of AB259.5 substrate became variable and did not yield reliable gain of fluorescence thereafter. Therefore, AB259.3 was chosen for further experiments.

To further characterize the assay, AB259.3 was treated with different concentrations of DNase I. This experiment demonstrated linear correlation between mean velocity ($V_m$) of the kinetic reaction and DNase I concentration (FIG. 2C). To detect specificity of the assay to DNase I that is a Ca/Mg-dependent endonuclease, AB259.3 probe was tested with 1 µg/ml DNase I in the presence of Ca++ and Mg++ (EAA buffer), in absence of the cations (deionized water), or in excess of EDTA (200 µM). The data showed that the assay measures Ca/Mg-dependent activity inhibited in the presence of EDTA (FIG. 2D). Finally, it was tested whether AB259.3 probe will detect inhibition of DNase I activity by DNase I inhibitors such as ZnCl2 and Zn-diisopropyl salicylate (Zn-DIPS) [8][30]. As expected, the inhibitors suppressed AB259.3 fluorescence increased induced by DNase I. Taken together these data suggest that AB259.3 is suitable for measuring endonuclease activity in vitro in a high throughput manner.

Example 3. Measurement of Endonuclease Activity in Serum and Urine

Figure 3:
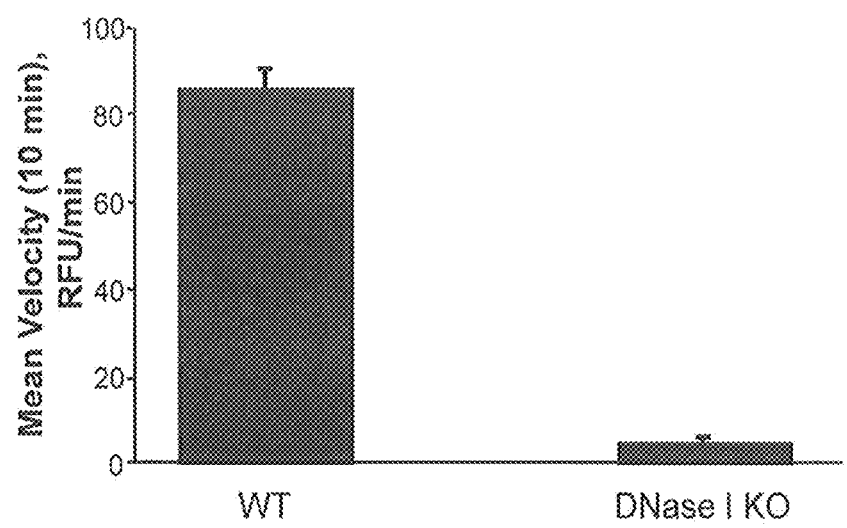
FIG. 3 depicts a graph showing the measurement of endonuclease activity in urine collected from DNase I knock-out (KO) mice and littermate wild-type (WT) controls using AB259.3.

Both serum and urine demonstrated high endonuclease activity that was measured in wild type mice (data are not shown). Because DNase I is the only endonuclease that is abundantly present in urine [10], urine samples from DNase I KO mice and their littermate WT controls were tested for endonuclease activity. The data suggest that 1:20 diluted urine from WT mice had high endonuclease activity as measured by $V_m$ in 10 min, while DNase I KO mice had no detectable endonuclease activity (FIG. 3).

Example 4. Intracellular Endonuclease Activity in Cultured Cells

Figure 4A:
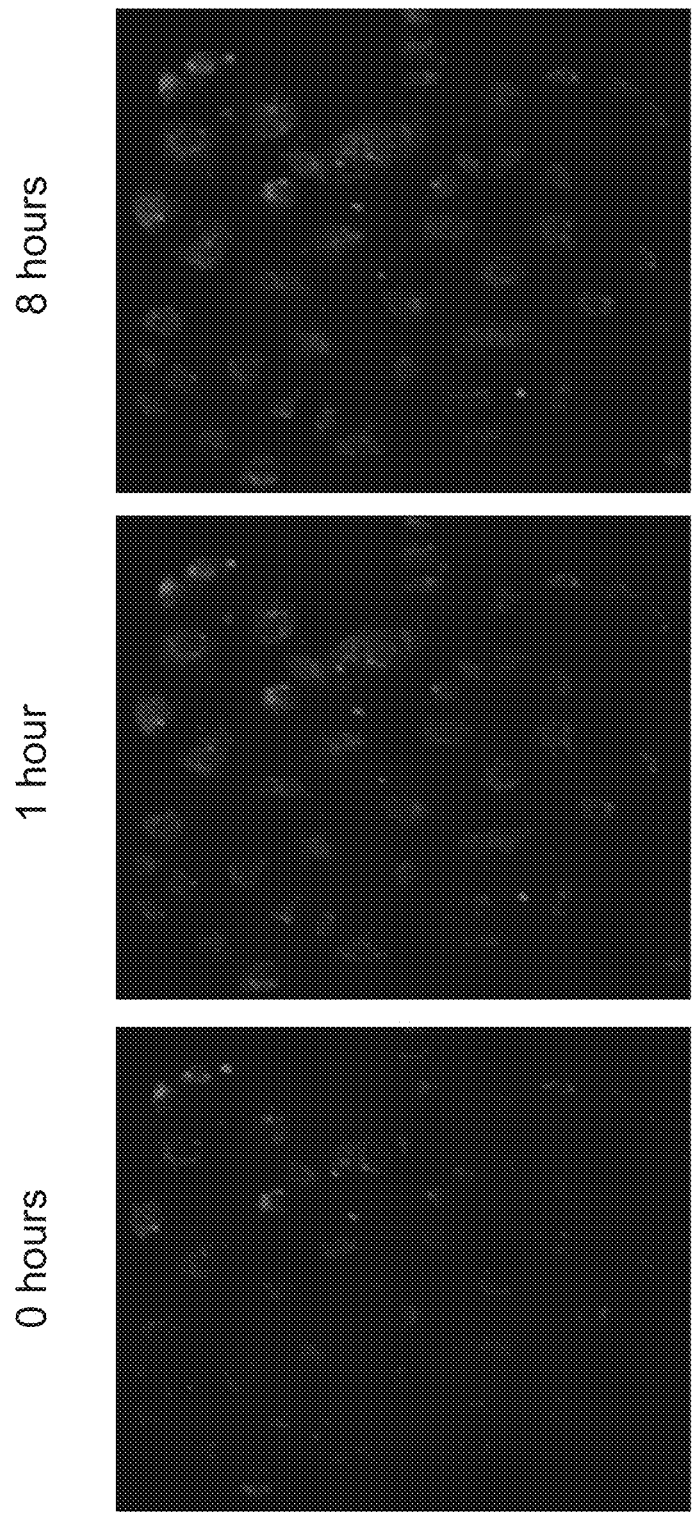
FIG. 4 presents images and graphs showing the measurement of endonuclease activity in cell cultures. (A) Application of the AB259.3 probe to cultured NRK-52E cells allows the kinetic measurement of endonuclease activity in the intact cells. Images were collected at 0, 1 and 8 hours after exposure to DNase I. (B-C) Fluorescent micrographs (B) of NRK-52E cells alone (No NIRF), with AB259.3 (control+NIRF), and with AB259.3 and cisplatin (Cisplatin+NIRF) or camptothecin (camptothecin+NIRF). The fluorescence was quantified and depicted graphically (C). (D) Fluorescent micrographs showing AB259.3 probe consumption by various types of cells 12 hours after transfection. Removal of the loop does not affect consumption of AB259.3 probe by cells. (E) A schematic illustrating representative structures of loop (e.g. AB259.3 SEQ ID NO; 2) and non-loop probes (AACACTC and SEQ ID NO: 5). (F) Mean intensities of NRK52E cells treated with naked non-loop or loop NIRF probe at various time points are depicted graphically. Non-loop probe (blue); loop-probe (red). (G) Fluorescent micrographs showing fluorescence of loop and non-loop probes in NRK-52E cells 10 hours after transfection. (H) Images of agarose gels showing confirmation of the AB259.3 probe DNA consumption by NRK-52E cells in vitro and by mouse kidney cells in vivo. Left panel, 2% agarose gel electrophoresis showing PCR products of NRK-52E cells & mouse kidney treated with loop probe. Right panel, 2% agarose gel electrophoresis showing PCR products of NRK-52E cells treated with non-loop non-loop. Specific probe-derived PCR products are shown by arrows.
Figure 4C:
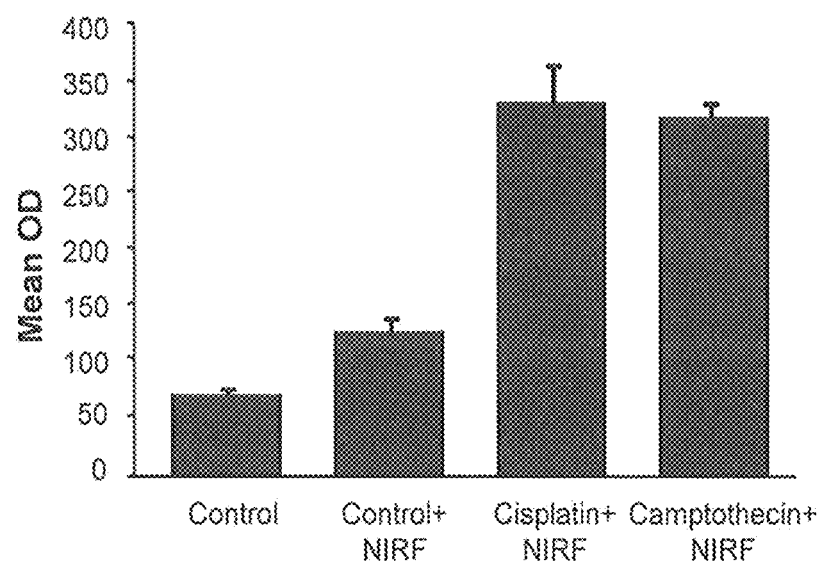
Figure 4D:
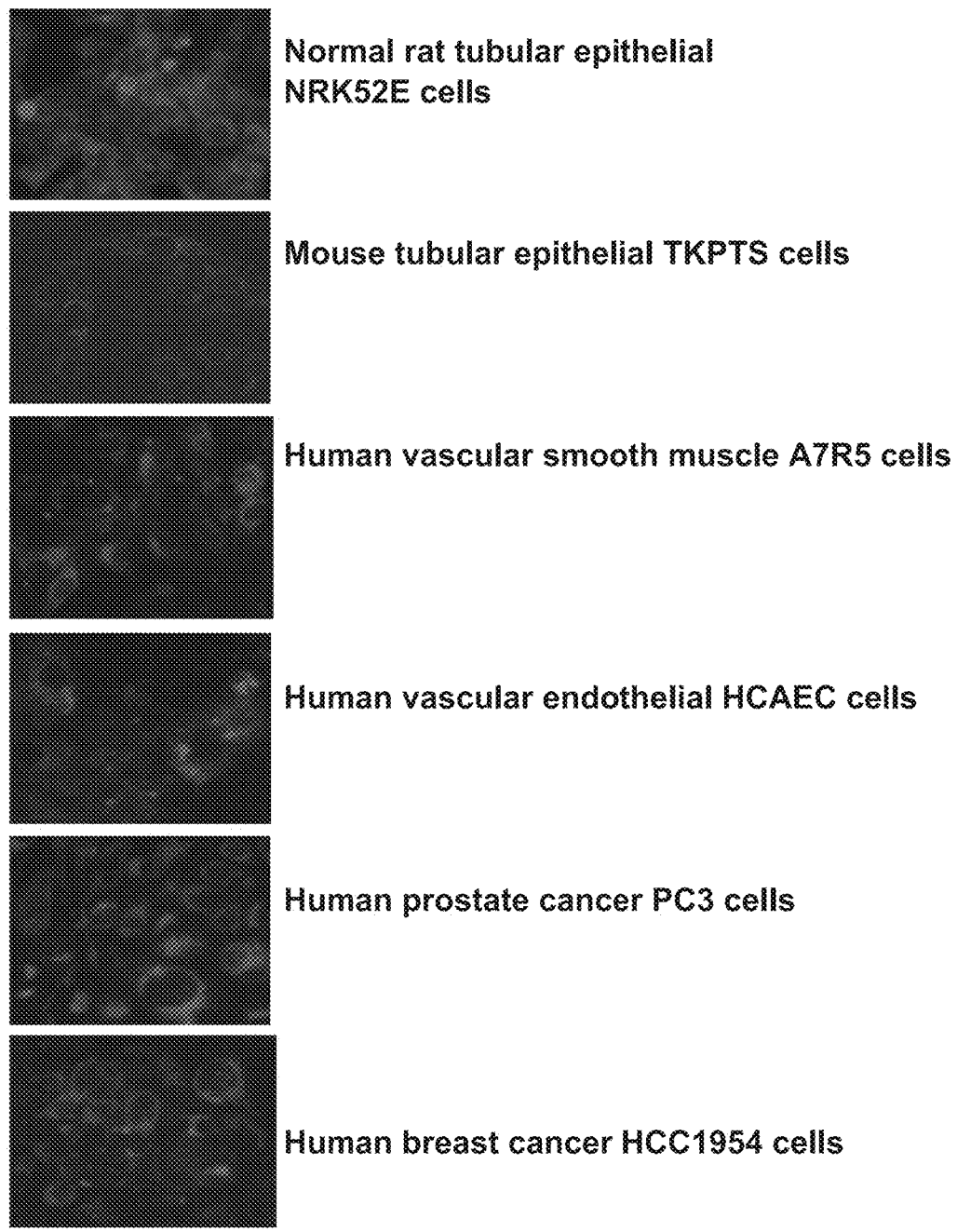
Figure 4E:
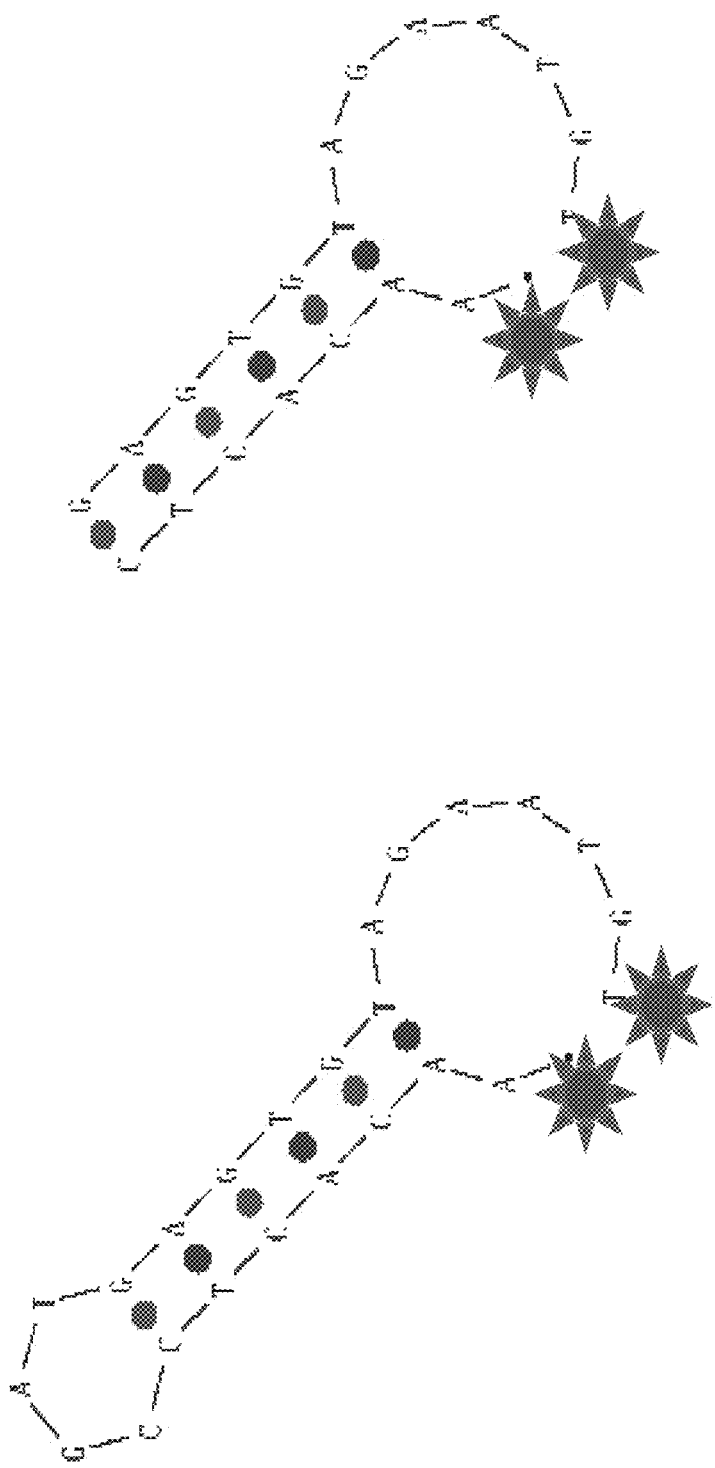
Figure 4F:
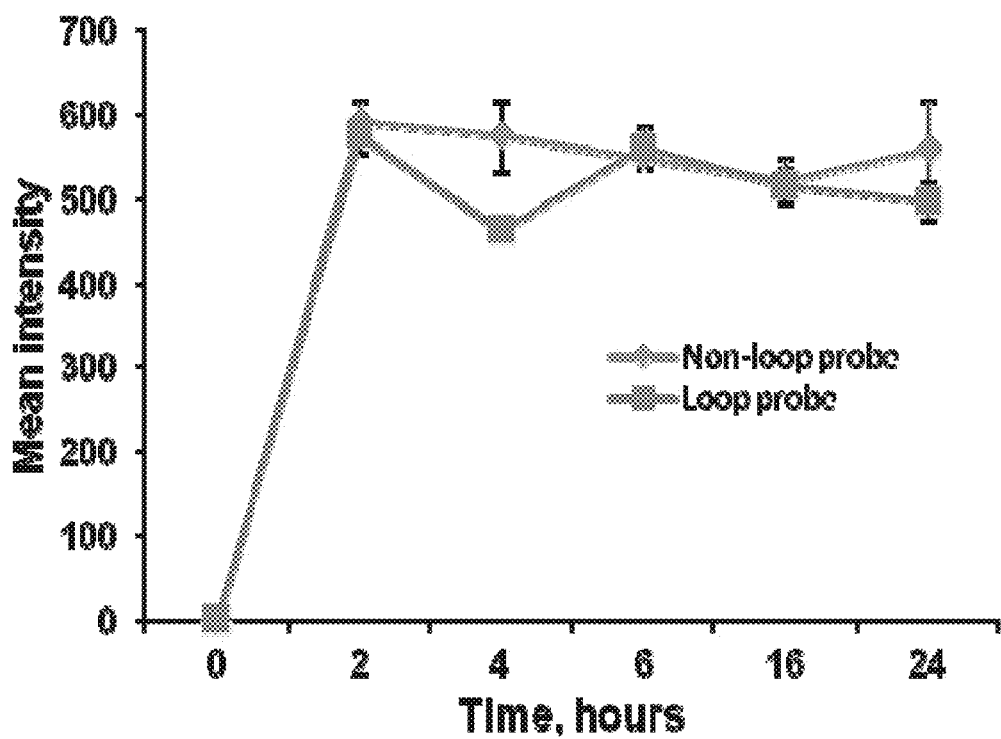
Figure 4G:
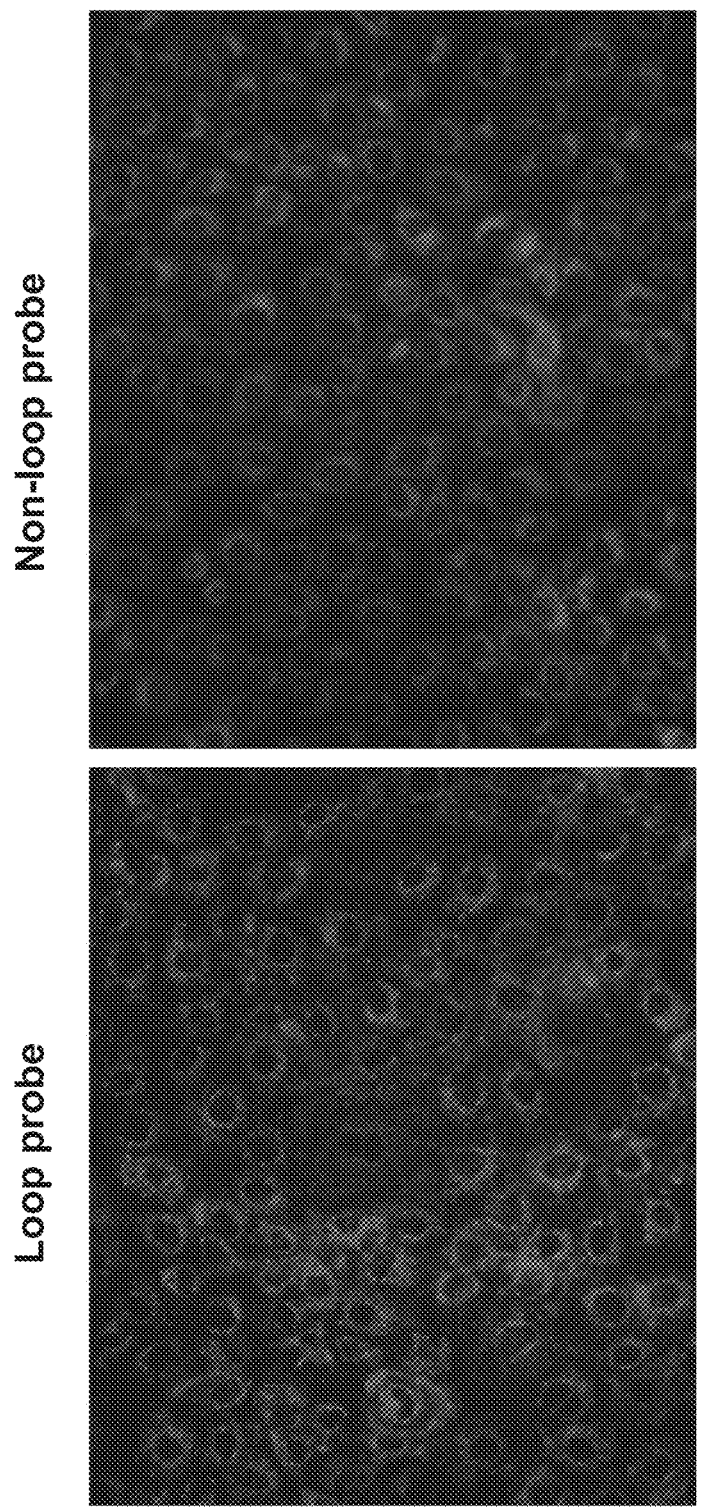
Figure 4H:
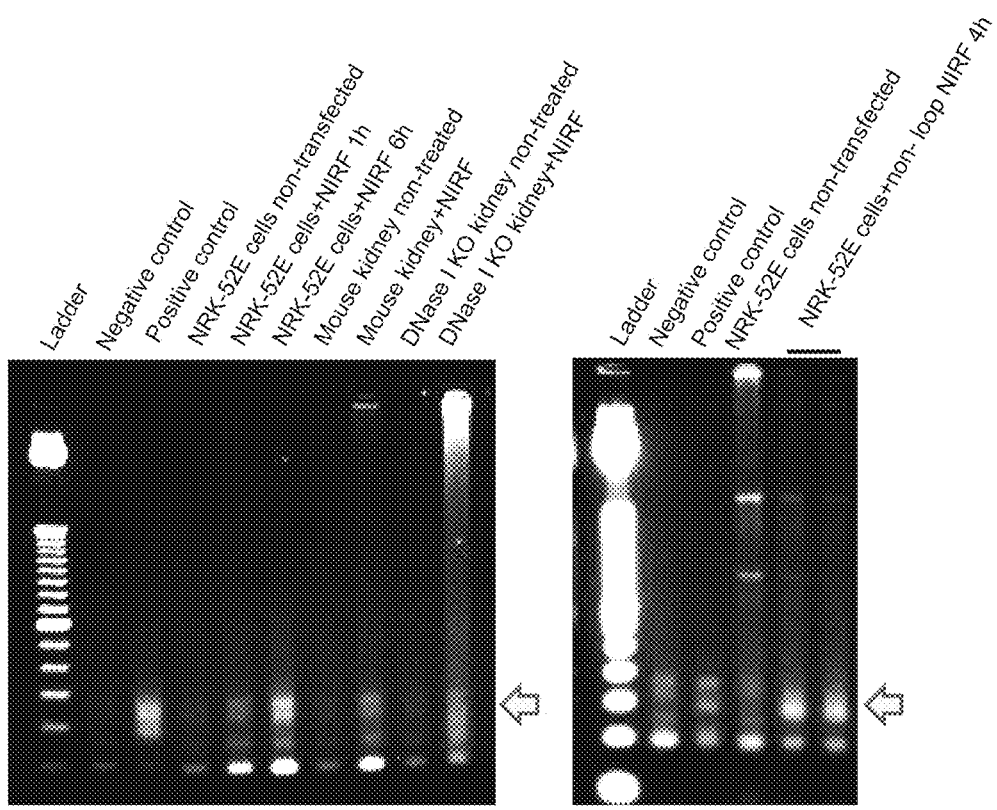

To test whether AB259.3 probe may be delivered intracellularly and thus be used as an indicator of endonuclease activity in live cells, NRK-52E cells were transfected with of AB259.3/Lipofectamine LTX complexes and imaged by time-lapse epifluorescence microscopy every 10 min for 8 hours. A 2.5-3 times increased fluorescence reached plateau in 1 hour after transfection and the cells retained fluorescent dye for the duration of experiment (FIG. 4A). To induce activity of endonucleases, cells were treated with cisplatin or camptothecin and imaged by time-lapse microscopy for Cy5.5 fluorescence. The data revealed significant increase of fluorescence in cells treated with both endonuclease inducers (FIGS. 4B and 4C). Therefore, it was concluded that AB259.3 can be delivered and used for intracellular monitoring of endonuclease activity in live cells. To further determine whether AB259.3 probe can be used in other cell lines, several of them were tested (FIG. 4D). This experiment showed that the probe is universally applicable to all tested cell lines. It was then determined whether the probe without the loop would be consumed by NRK-52E cells equally to the original loop probe. The experiments showed that the cell consumption is not affected by the presence of the loop (FIG. 4E-G). Finally, PCR was used to determine whether the DNA part (as opposed to the fluorophores) of the probes enters the cells in vivo and in vitro. These experiments suggested that DNA of the probes has been delivered into the cells (FIG. 4H).

Example 5. Measurement of Endonuclease Activity Ex Vivo

Figure 5A:
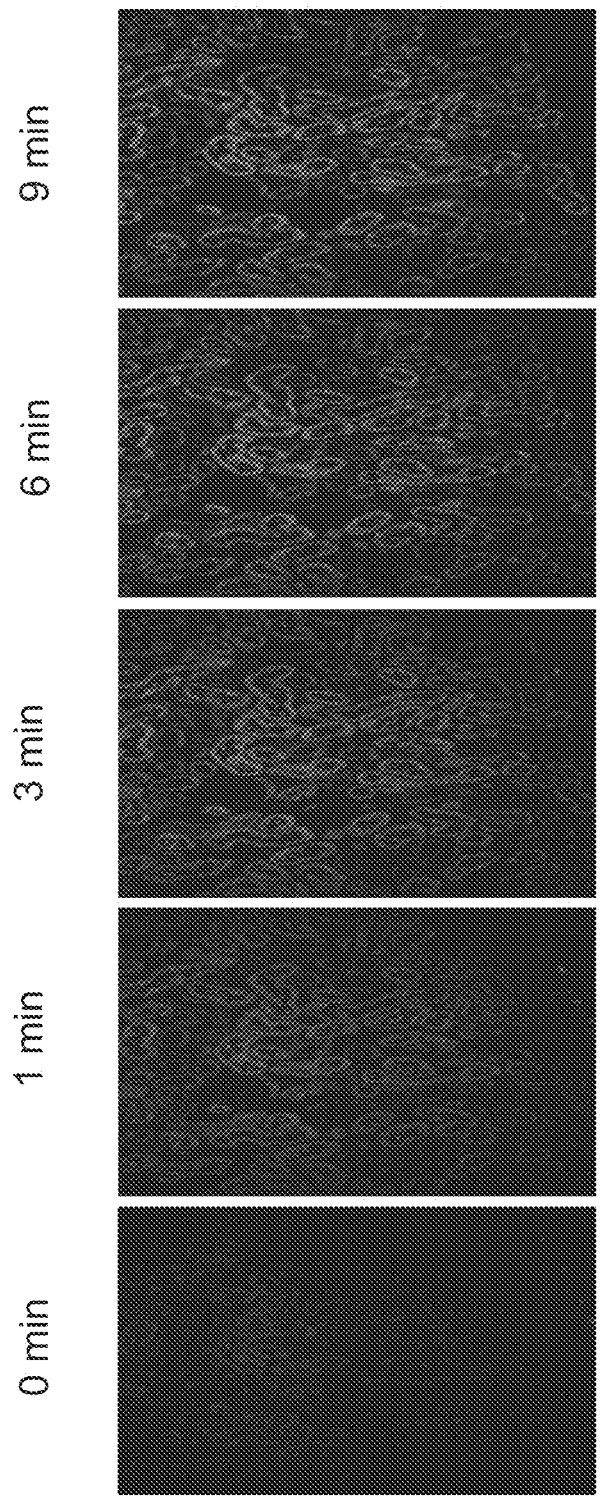
FIG. 5 presents images and graphs showing ex vivo measurement of endonuclease activity in mouse kidney cryosections. (A) shows fluorescent micrographs captured in 1-min intervals and (B) graphically depicts the amount of fluorescence over time. (C-D) Fluorescent micrographs showing the endonuclease activity is significantly suppressed by EDTA (C); and is almost undetectable in DNase I KO mice (D). (E) Fluorescent micrographs showing a comparison of endonuclease activity in cryosections of several organs using AB259.3 probe. (F-G) Endonuclease activity in cryosections of orthotopic PC3 prostate cancer xenografts, surrounding prostate and normal prostate tissues. The fluorescence shown in the micrographs (F) is quantified and depicted graphically (G).
Figure 5:
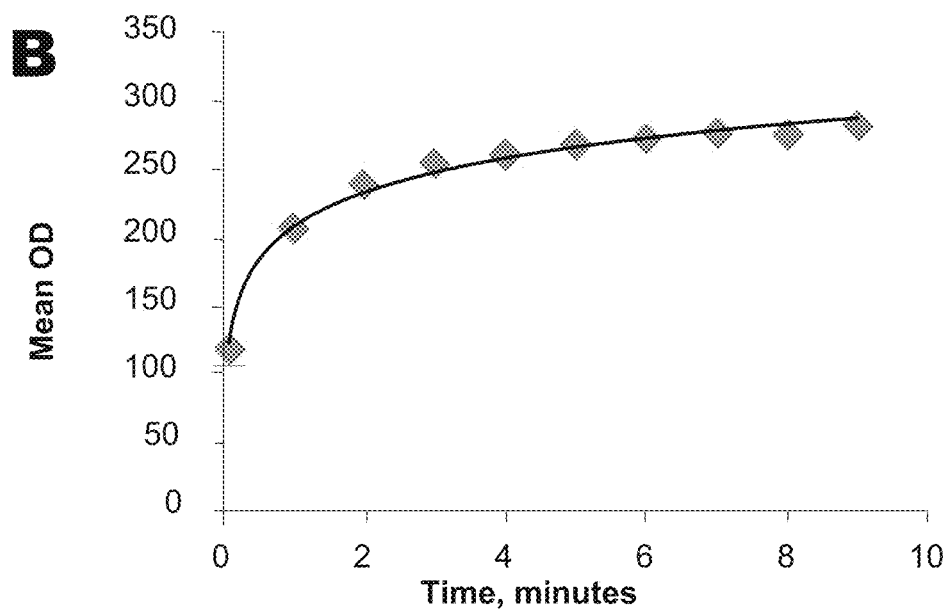
Figure 5:
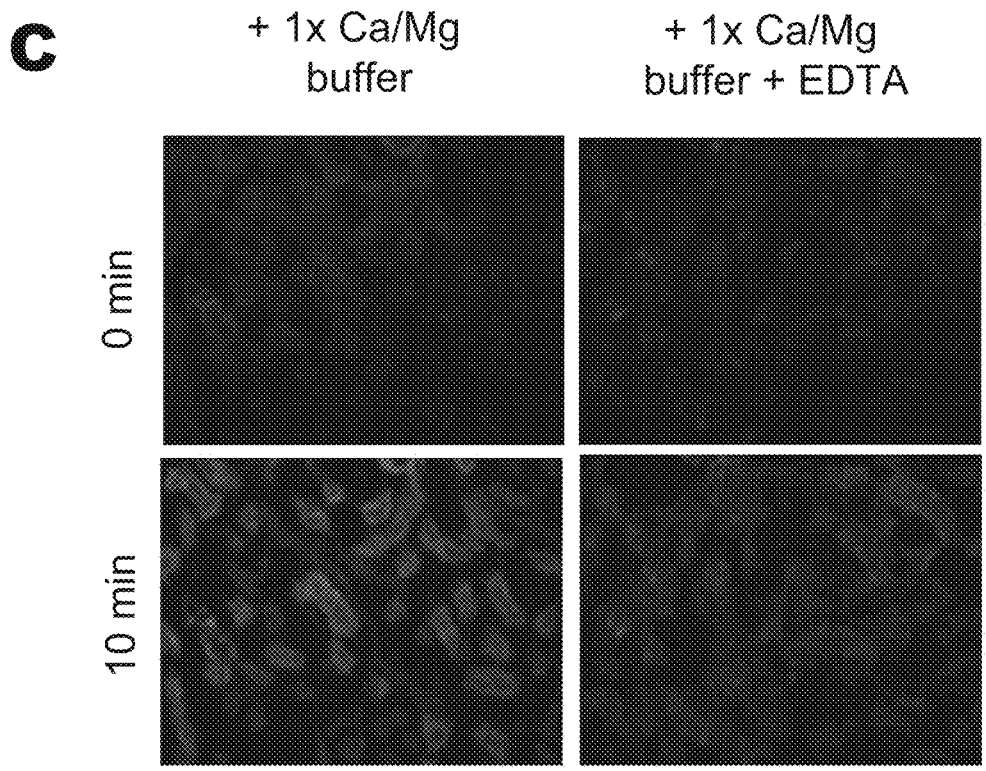
Figure 5D:
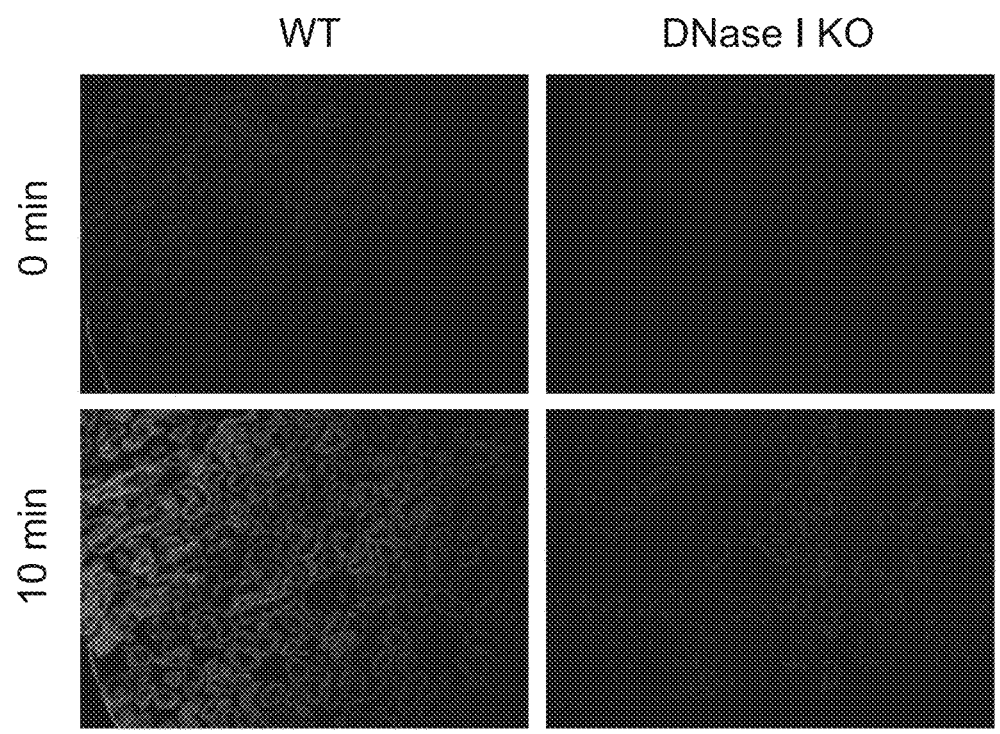

Next it was examined whether AB259.3 probe can be used for measurement of endonuclease activity in tissue sections. Kidneys were used because they are known for high activity of DNase I (Ca/Mg-dependent endonuclease) [28, 31]. Freshly prepared 10 μm thick cryosections of wild-type (WT) mouse kidney were exposed with 5 μM AB259.3 probe in presence of EAA buffer at 37° C. and time-lapse imaged for 10 min with 1-min intervals. The data suggested that Cy5.5 fluorescence was significantly increased 2.5 times compared to starting point (FIGS. 5A and 5B). The highest endonuclease activity was observed in both distal and proximal tubular epithelium and some in interstitial zones, while gloms had the lowest activity. The plateau of fluorescence was reached in 2-3 min. In the presence of EDTA, the increase of fluorescence was prevented, indicating that the endonuclease activity was cation-dependent (FIG. 5C). Compared to WT mice, DNase I KO mice had minimal increase of the fluorescence (FIG. 5D). Overall, these data indicate that the probe detects virtually only DNase I activity in the kidney parenchyma.

Figure 5E:
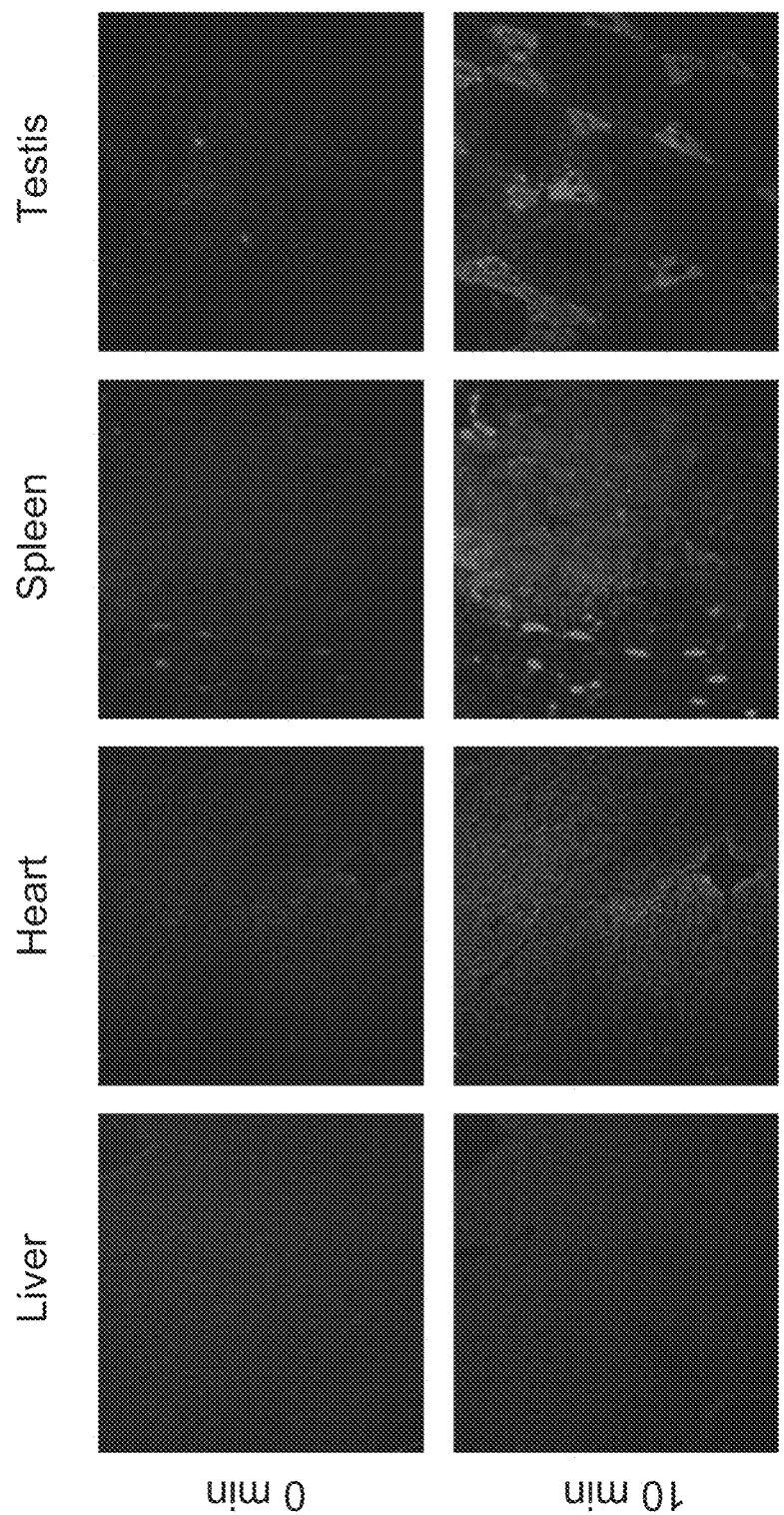

Next, AB259.3 was tested in some other mouse organs, such as liver, heart, spleen and testicles. The data showed that heart and liver had the lowest endonuclease activity as assessed by $V_m$ index (FIG. 5E). In testicles, interstitium had significantly higher activity compared to the other compartments. Similarly, the white pulp of spleen had significantly higher endonuclease activity compared to the red pulp or stromal compartment.

Figure 5F:
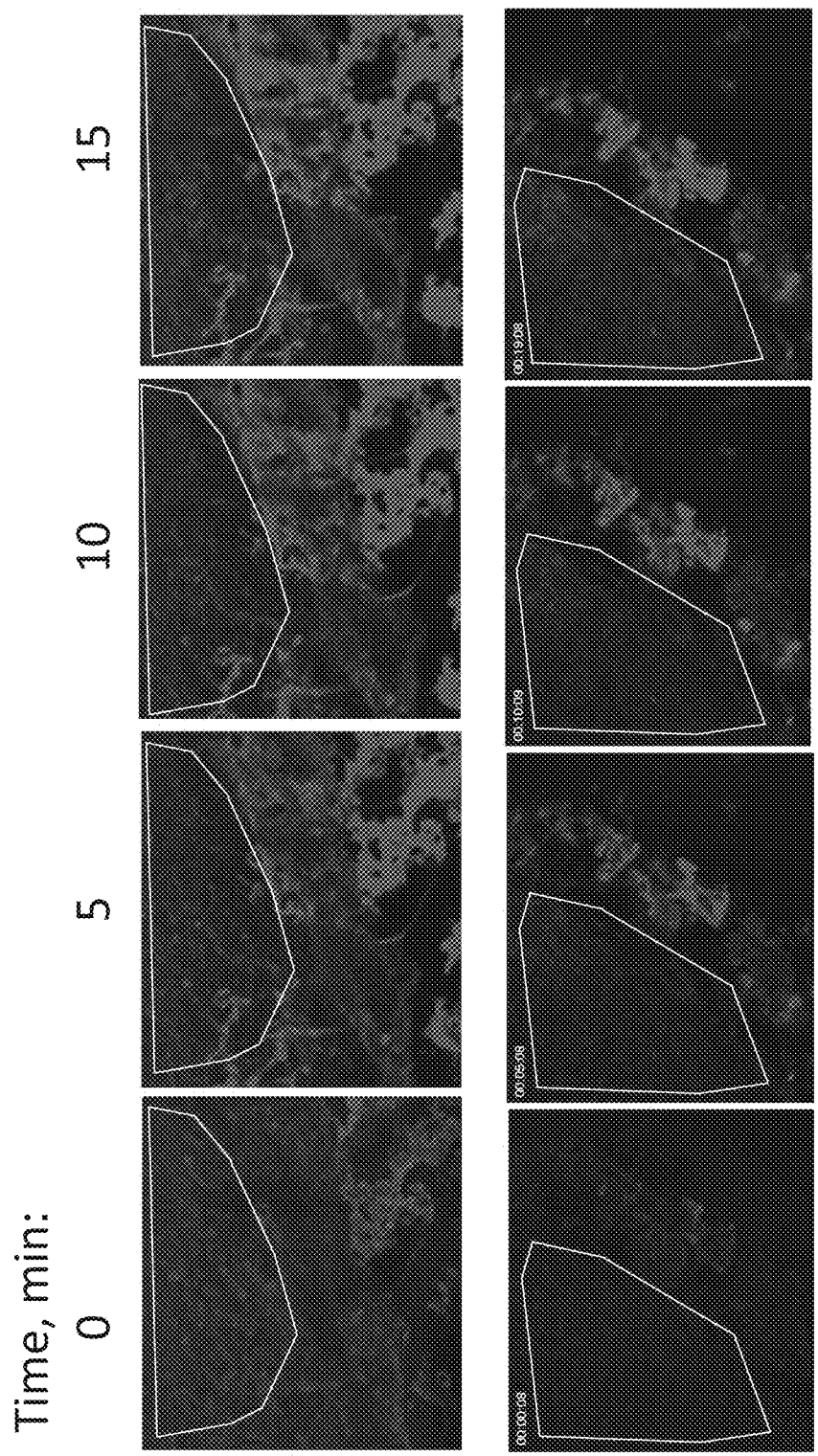
Figure 5G:
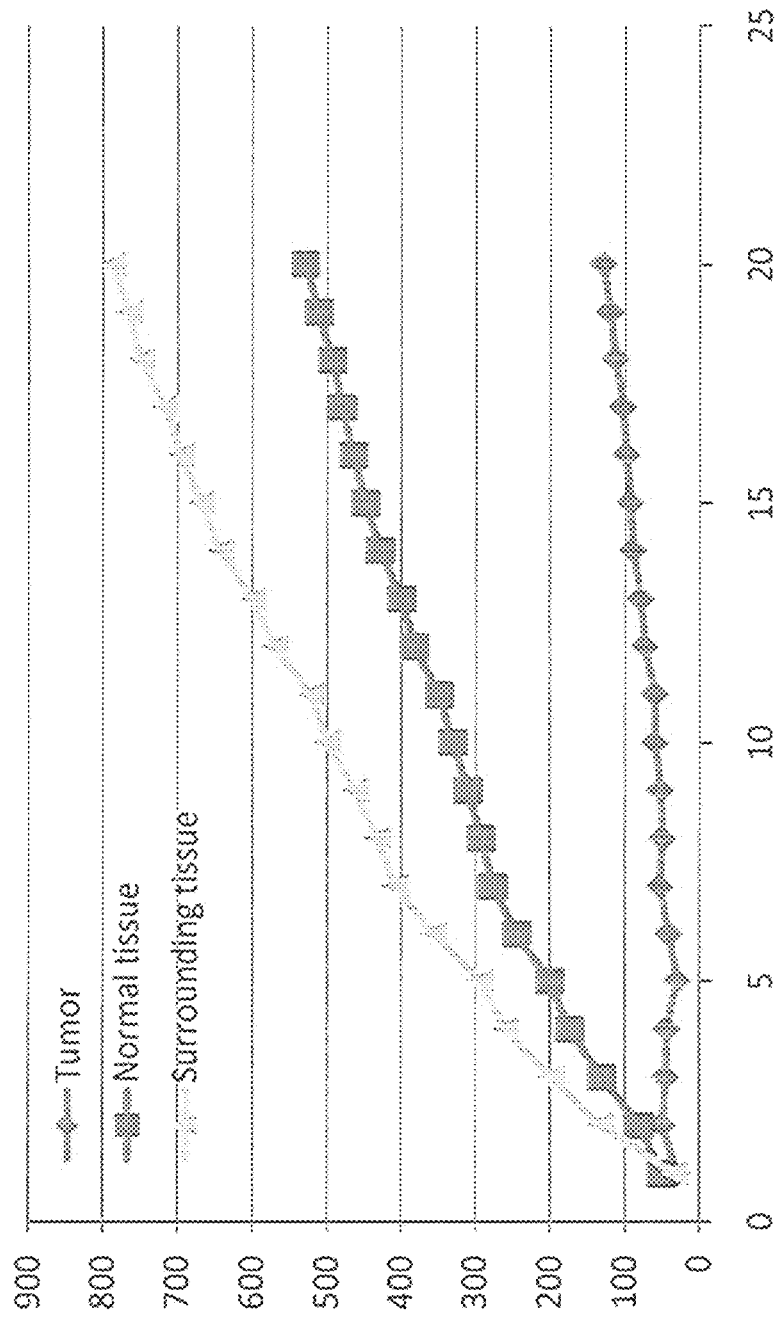

It was also tested if the probe is able to distinguish endonuclease activity between normal and tumor tissue. Prostate tumor xenografts were used, which are known to have low endonuclease activity [12] compared to normal prostate, which has high Ca/Mg-dependent DNase I activity [32]. The staining showed marked difference in the activity between the prostate PC3 tumor xenograft and the prostate (FIG. 5F). Interestingly, the surrounding tissue had higher endonuclease activity than the rest of the organ. Taken together the data suggest AB259.3 probe is a good tool for endonuclease activity measurements in fresh or frozen tissues and can distinguish the activity between tissue compartments and between normal and endonuclease-deficient tumor tissues.

Example 6. Visualization of Endonuclease Activity In Vivo

Figure 6A:
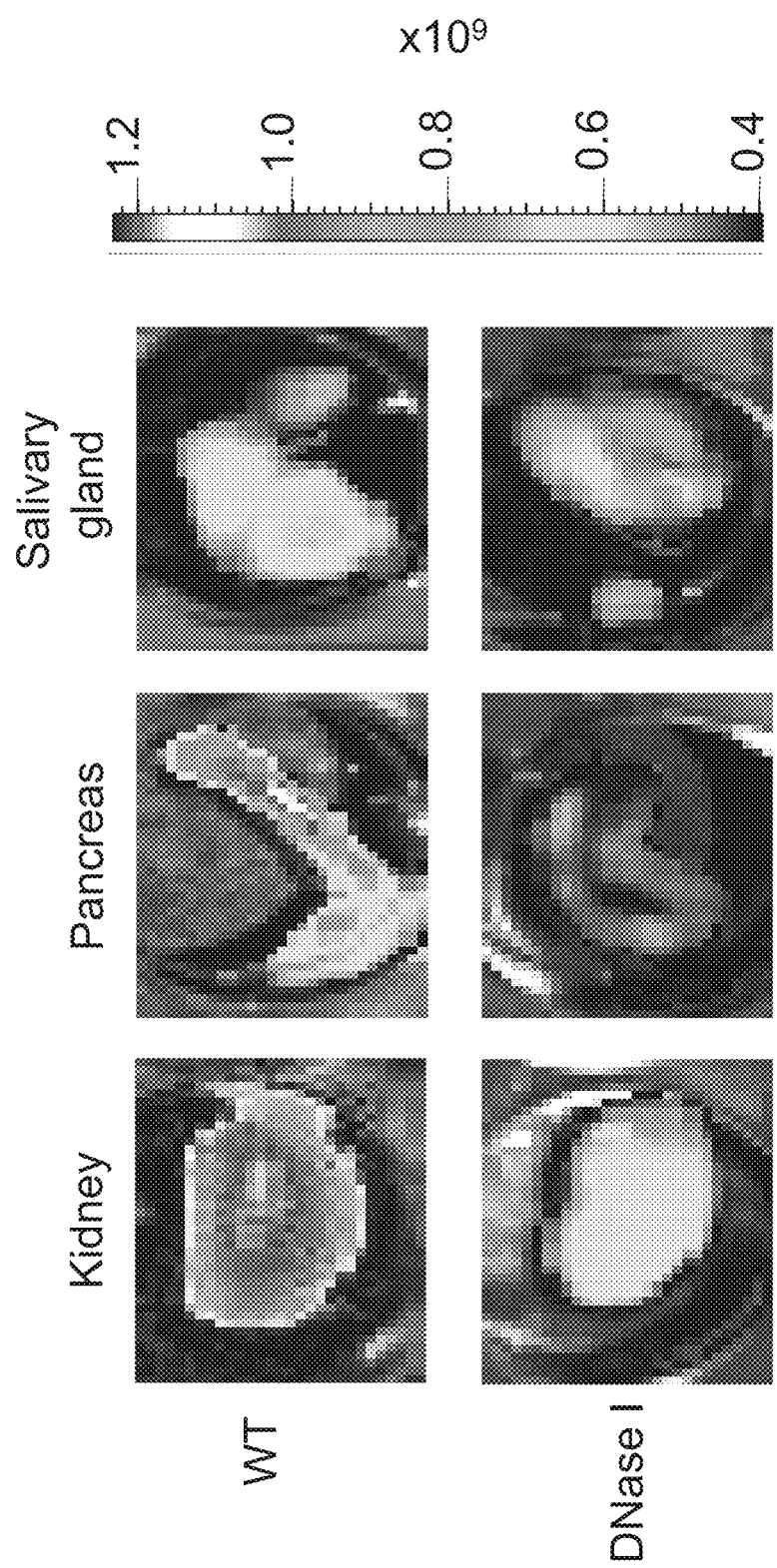
FIG. 6 shows images and graphs depicting endonuclease activity in mouse organs isolated after the AB259.3 probe injection. Representative images are shown in (A), and (B) depicts average radiant efficiency (fluorescence gained with no respect to autofluorescence background) and relative increase of fluorescence based on increase from "0" time point.
Figure 6B:
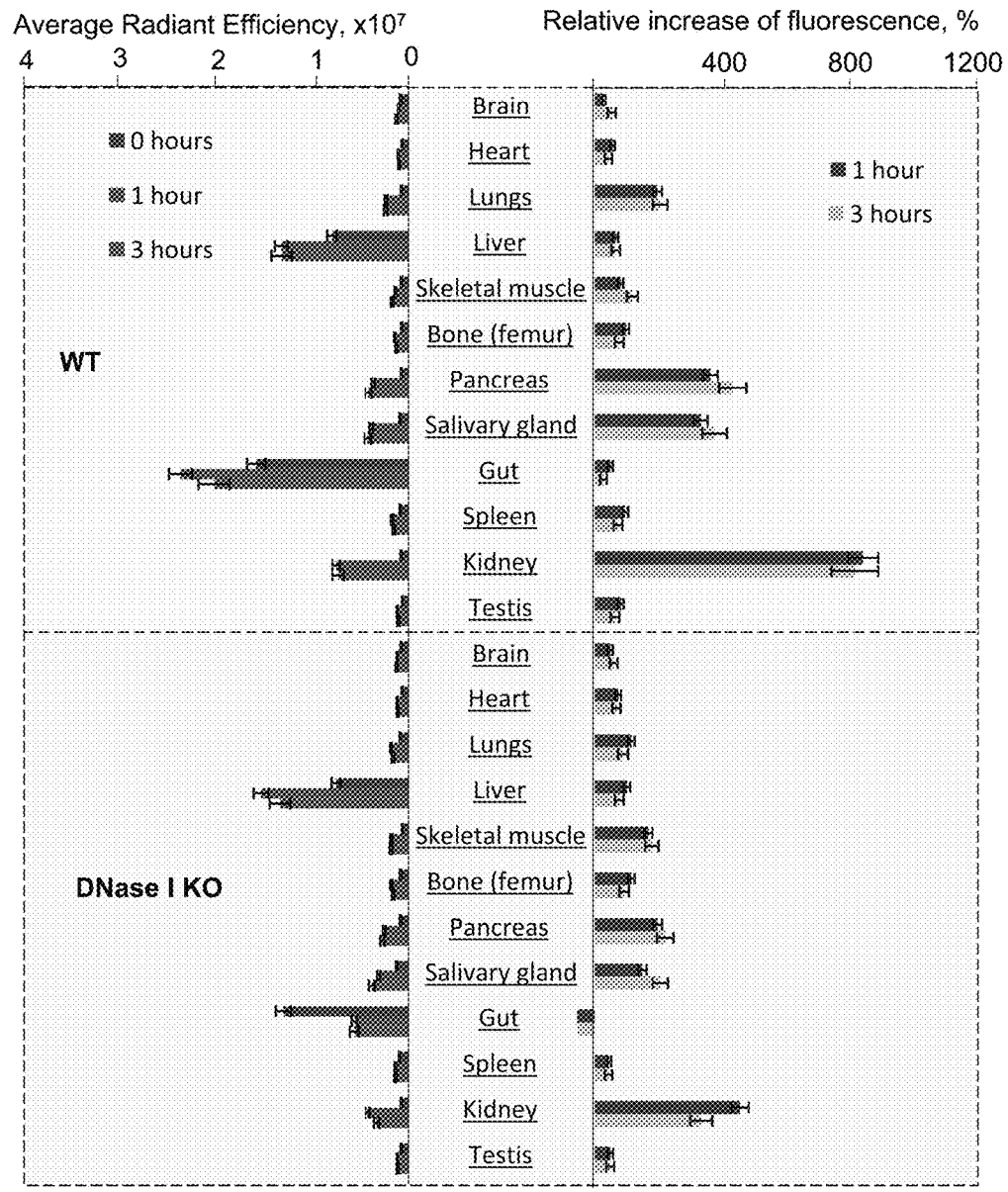

In the next set of experiments, it was tested whether AB259.3 probe is suitable for in vivo measurement of DNase I and endonuclease activity in internal organs. For this, WT and DNase I KO mice were subjected to intravenous administration of AB259.3 probe (50 nmol/kg). The organs including brain, heart, lung, muscle, bone (femur), liver, pancreas, salivary gland, jejunum, spleen, kidney and testicles were collected in 1 or 3 hours after injection and measured for Cy5.5 fluorescence using a Xenogen-IVIS instrument. As shown in FIG. 6, all studied organs from WT mice gained fluorescence in both 1 and 3 hours after injection. Kidneys, pancreas, salivary glands and lungs were among those that had the most prominent relative increase of Cy5.5 fluorescence in WT mice with markedly lower level of fluorescence in DNase I KO mice. Despite highest absolute fluorescence values in gut and liver, relative gain of fluorescence in these organs was quite modest due to the high background autofluorescence. It was concluded that there is a distinct difference in organs with high endonuclease activity and hence, it is expected that the probe can be used for intravital imaging. Based on absolute and relative gain of fluorescence, kidneys appeared to be the most visibly distinctive organ with the highest DNase I activity detected by the AB259.3 probe.

Example 7. Intravital Assessment of Endonuclease Activity in Kidneys

Figure 7A:
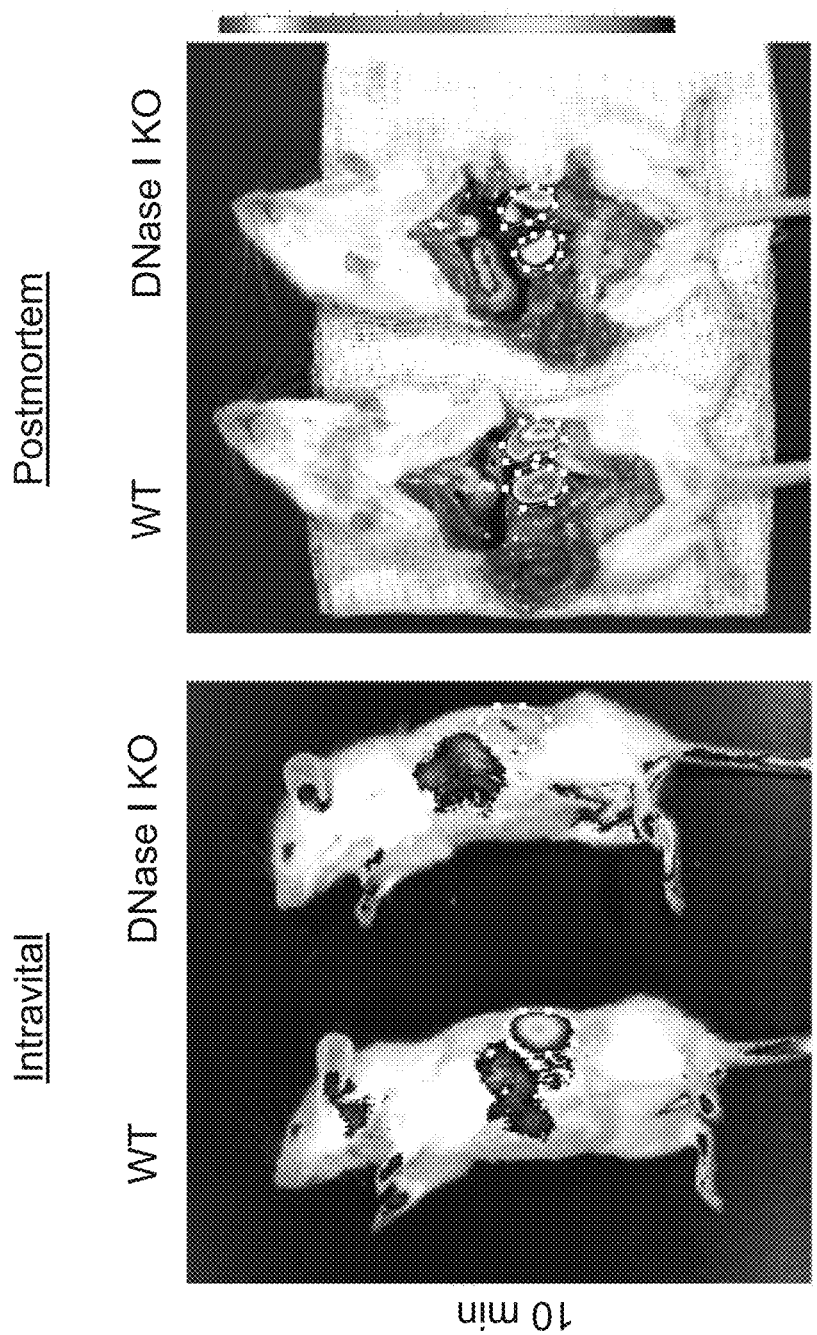
FIG. 7 shows images and graphs depicting in vivo assessment of endonuclease activity in normal kidneys. (A) Ten minutes after intravenous AB259.3 probe administration, WT mice have significantly higher endonuclease activity in their kidneys compared to DNase I KO mice as demonstrated by intravital imaging (upper panels) and confirmed in euthanized mice (lower panels). *P<0.05 compared to WT mice. (C) Five hours after intravenous AB259.3 probe administration AB259.3 remains in kidneys and WT mice still show higher fluorescence compared to DNase I KO animals. *P<0.05 compared to WT mice. (E) Kinetic assessment of Cy5.5 fluorescence in exposed kidneys of live animals: WT mice demonstrated significantly higher Cy5.5 fluorescence in 10 min after probe injection, compared to DNase I KO mice. (F) Injection of recombinant DNase I to DNase I KO mouse kidneys make the activity look equal to WT mice. Quantitative data for (A, C, F) are shown in (B, D, G). Quantitative data for presented as average radiant efficiency in kidneys (outlined areas), *p<0.05 compared to WT+saline; *P<0.05 compared to DNase I KO+saline.
Figure 7B:
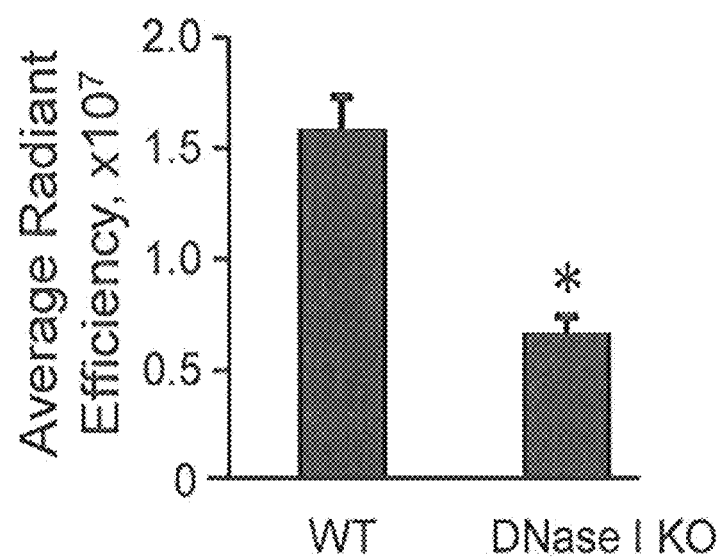
Figure 7C:
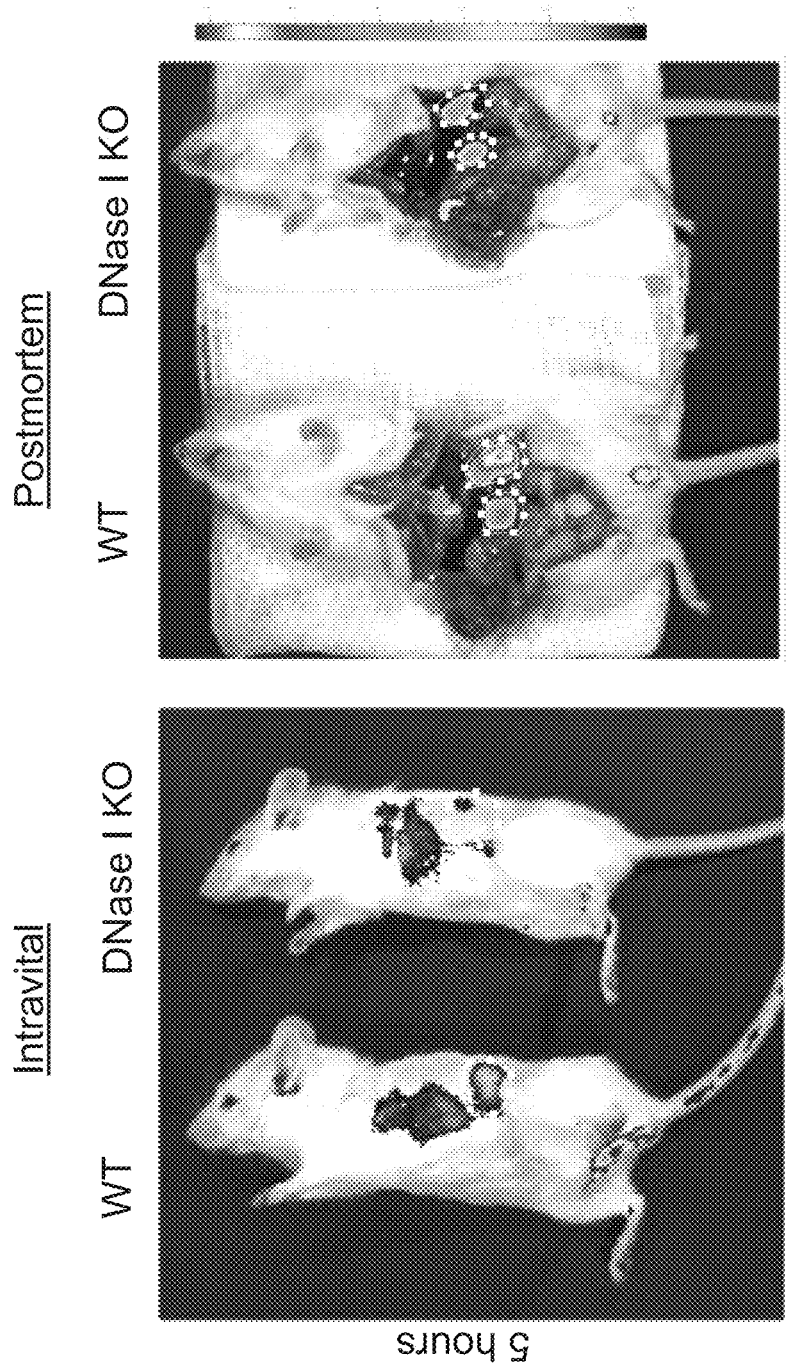
Figure 7D:
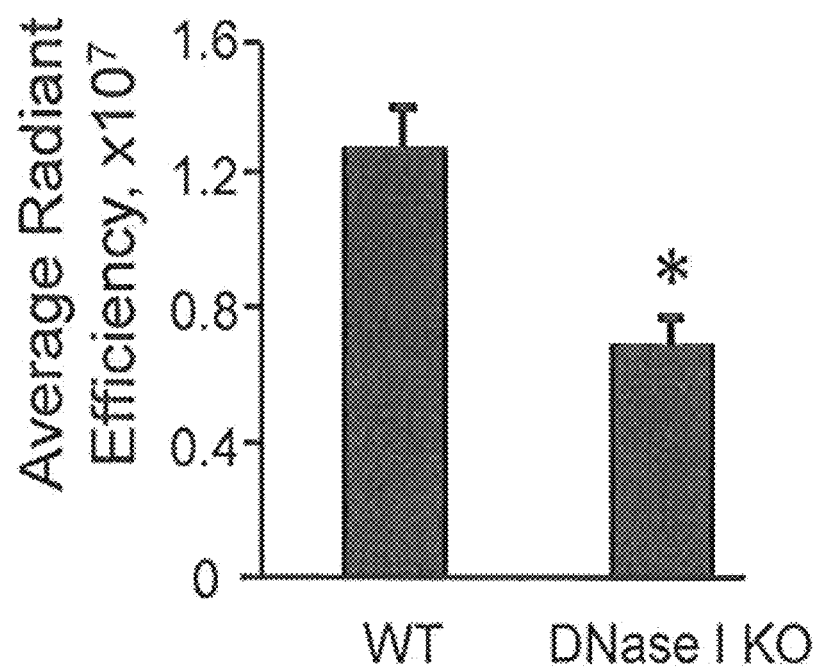

At the next step, WT and DNase I KO mice were anesthetized and intravenously administered with 50 nmol/kg of AB259.3 probe followed by intravital imaging using Xenogen-IVIS. The data suggested that after AB259.3 administration experimental mice have outstanding fluorescence in the areas of kidneys. Probe accumulated in kidneys instantly and gained fluorescence that reached plateau at 10 min (FIGS. 7A and 7B). Fluorescence seemed to be truly originated from kidneys (not blood) because it was not detected in major vessels and other highly vascularized organs and was retained by kidneys for at least 5 hours (FIGS. 7C and 7D). Cy5.5 fluorescence was higher in WT mice compared to DNase I KO mice and renal accumulation of AB259.3 was confirmed postmortem in mouse kidneys after euthanasia.

Figure 7E:
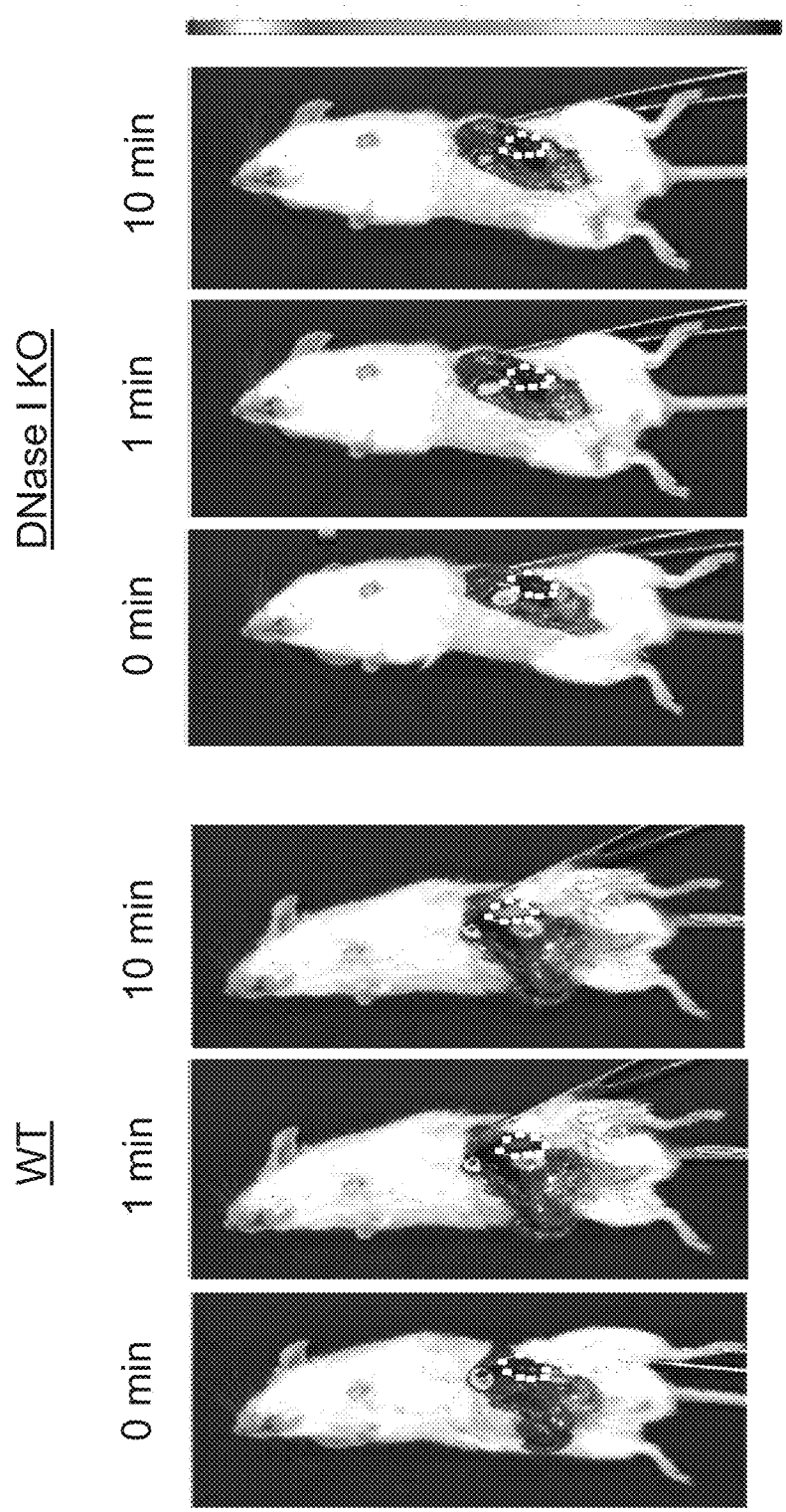
Figure 7F:
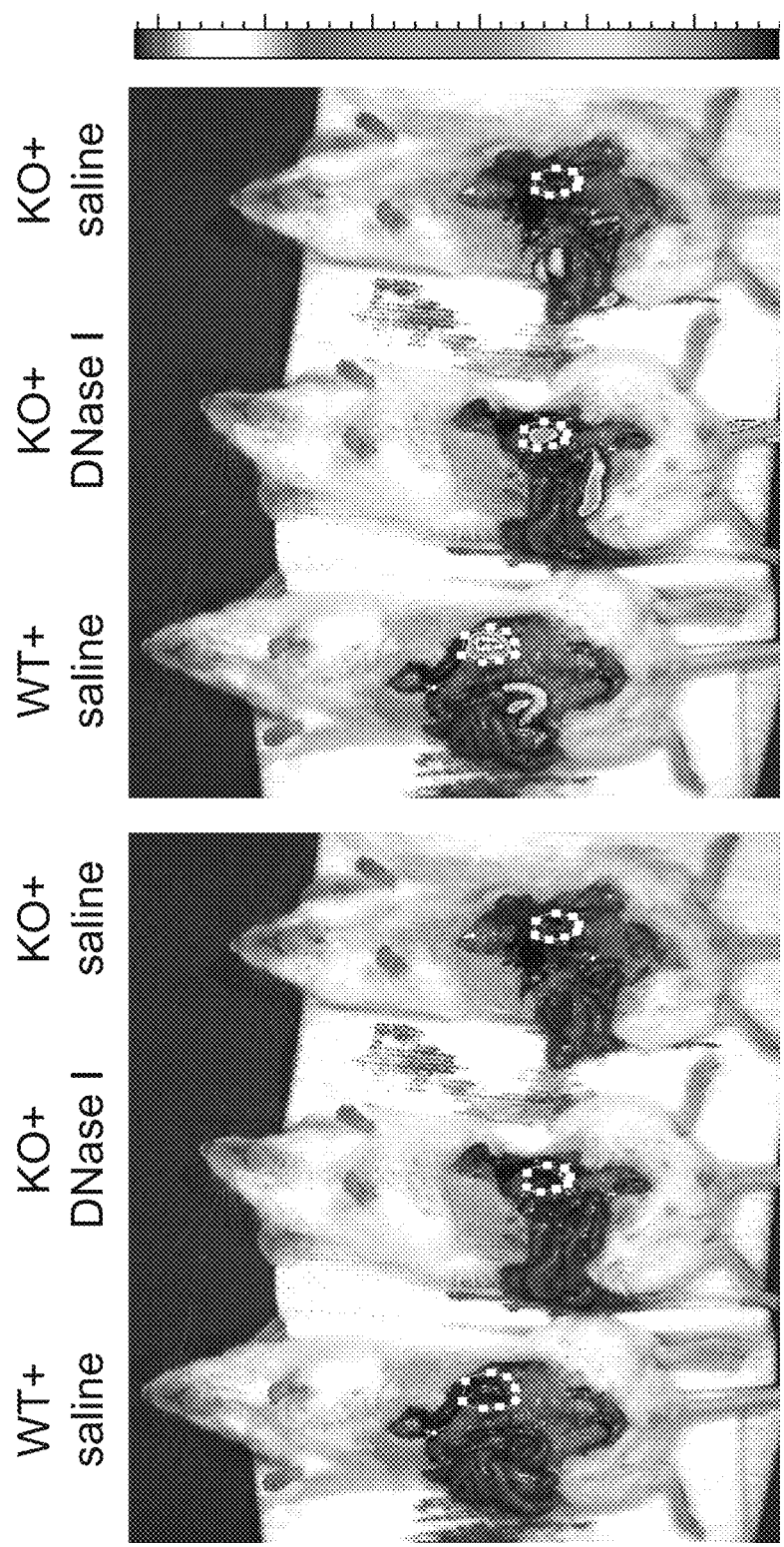
Figure 7G:
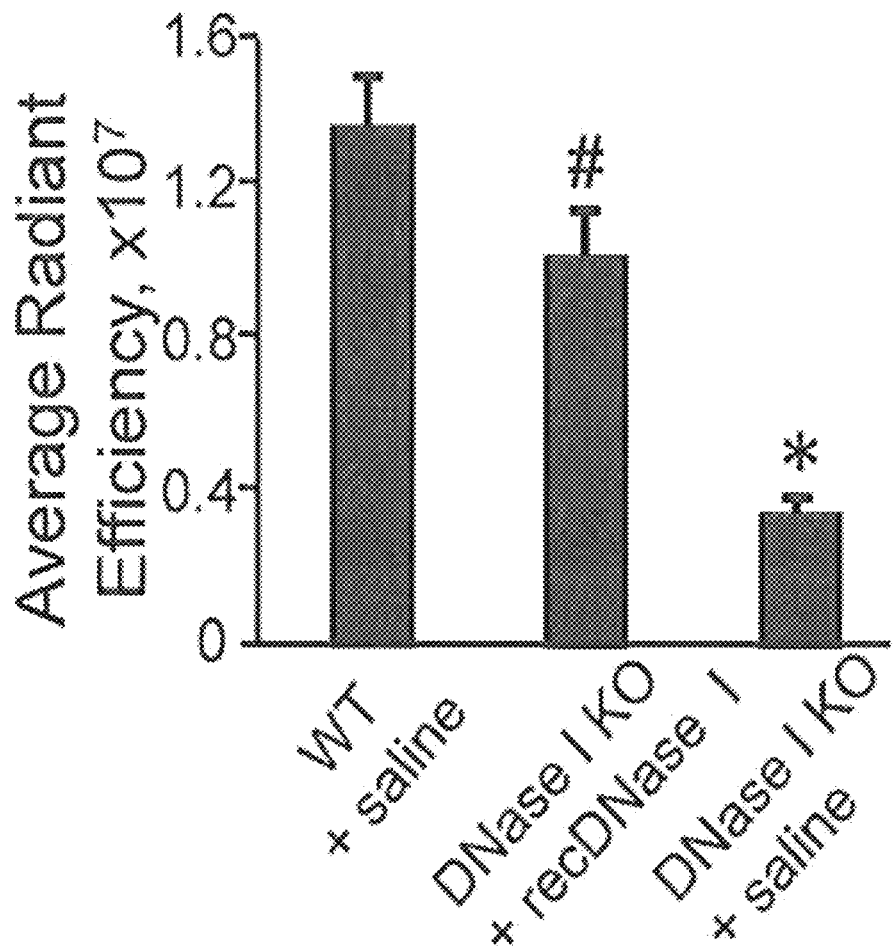

To additionally confirm preferential accumulation and processing of AB259.3 probe in kidneys, separate set of mice was deeply anesthetized and subjected to abdominal incision and real-time intravital visualization of left kidney while performing intravenous injection of AB259.3 probe. Kinetic assessment of endonuclease activity confirmed that probe specifically accumulated and gained fluorescence in the kidney (FIG. 7E). Cy5.5 fluorescence reached a plateau at 10 min and small fraction of fluorescent probe started to appear in bladder, however, kidneys retained significant part of fluorescence. Because of the obvious difference in fluorescence between WT and DNase I KO mice, it was than explored further by delivering of recombinant DNase I to the kidneys of DNase I KO mice. For this, DNase I KO animals were subjected to open surgery that was used to administer 5 µl DNase I (0.1 mg/ml) to subcapsular space of upper ventral zone of left kidney. To control effect of DNase I, additional WT and DNase I KO mice were injected with same volume of the vehicle. Immediately after injection, mice were injected with 50 nmol/kg of AB259.3 probe intravenously and then imaged in a Xenogen-IVIS. The results suggested that DNase I-injected DNase I KO mice had Cy5.5 fluorescence comparable to WT mice, while kidneys of DNase I KO mice injected with vehicle had low fluorescence (FIGS. 7F and 7G). Thus, the data clearly demonstrated that AB259.3 can be used for visualization and intravital measurement of endonuclease activity in kidneys.

Example 8. Histological Distribution of AB259.3 Probe in Kidneys

Figure 8:
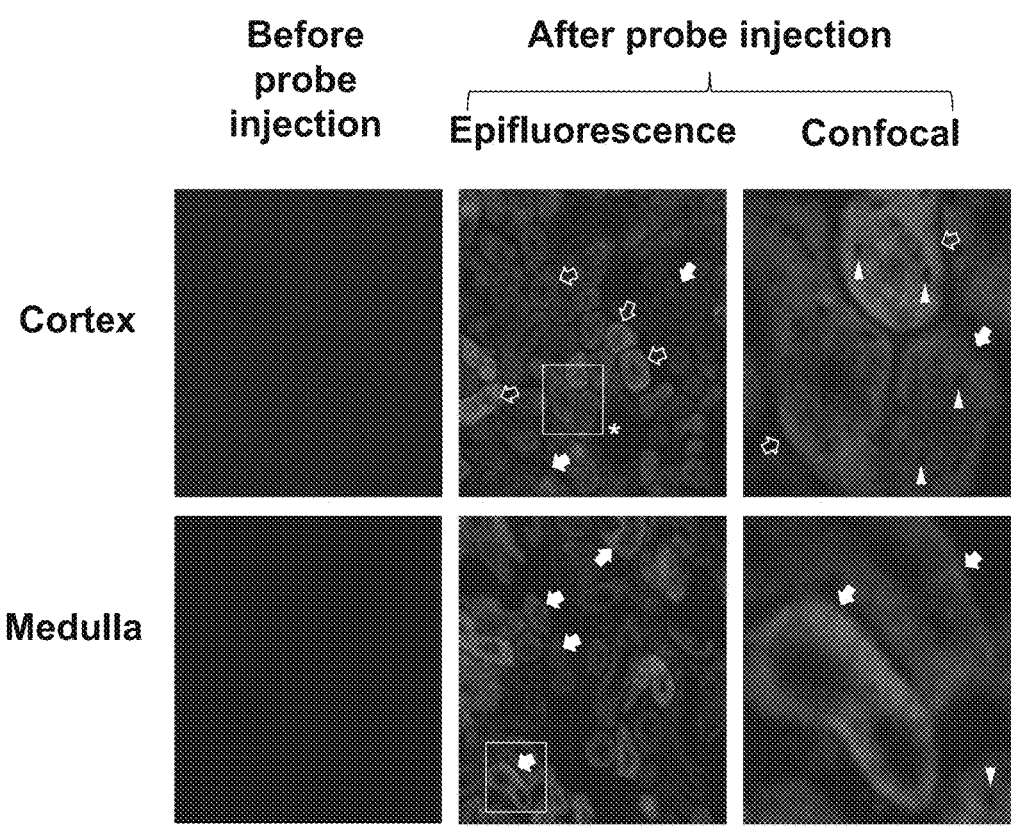
FIG. 8 shows fluorescent micrographs of mouse kidney cortex and medulla cryosections 3 hours after intravenous injection with the AB259.3 probe. Endonuclease activity is detected by epifluorescent (middle panels) or confocal microscopy (right panels) in the majority of proximal tubules (empty arrows), and some distal tubules (filled arrows). Glomes (asterisk) and cell nuclei (arrowhead) are negative for endonuclease activity.

It was assessed whether AB259.3 probe is specifically accumulated in any renal compartments or its accumulation in the kidney is simply due to the excretion with urine. For this, WT mice were administered intravenously with 50 nmol/kg of AB259.3 probe and kidneys were collected in 1 or 3 hours, frozen, cryosectioned and examined under fluorescent microscope in 628/40-692/40 spectrum. It was observed that by 1 hour, cortical compartment, and mainly proximal tubules already contained significant amount of activated AB259.3 probe. Morphologically, fluorescence was detected mainly in membranous parts of the epithelial cells, such as basolateral and, to lesser extent, at apical surface. Most of the epithelial cells demonstrated cytosolic redistribution of AB259.3 probe clearly indicating that the probe is consumed by the cells. Stromal compartments demonstrated rare (if any) fluorescence throughout the kidney section. In 3 hours, the activated probe started to appear in medullar compartment and distal tubules, however proximal tubules still retain significant amount of activated AB259.3 probe (FIG. 8). Glomerular compartment did not demonstrate any fluorescence during this experiment suggesting that the activation of the probe occurred in tubular epithelium, not in blood.

Figure 9A:
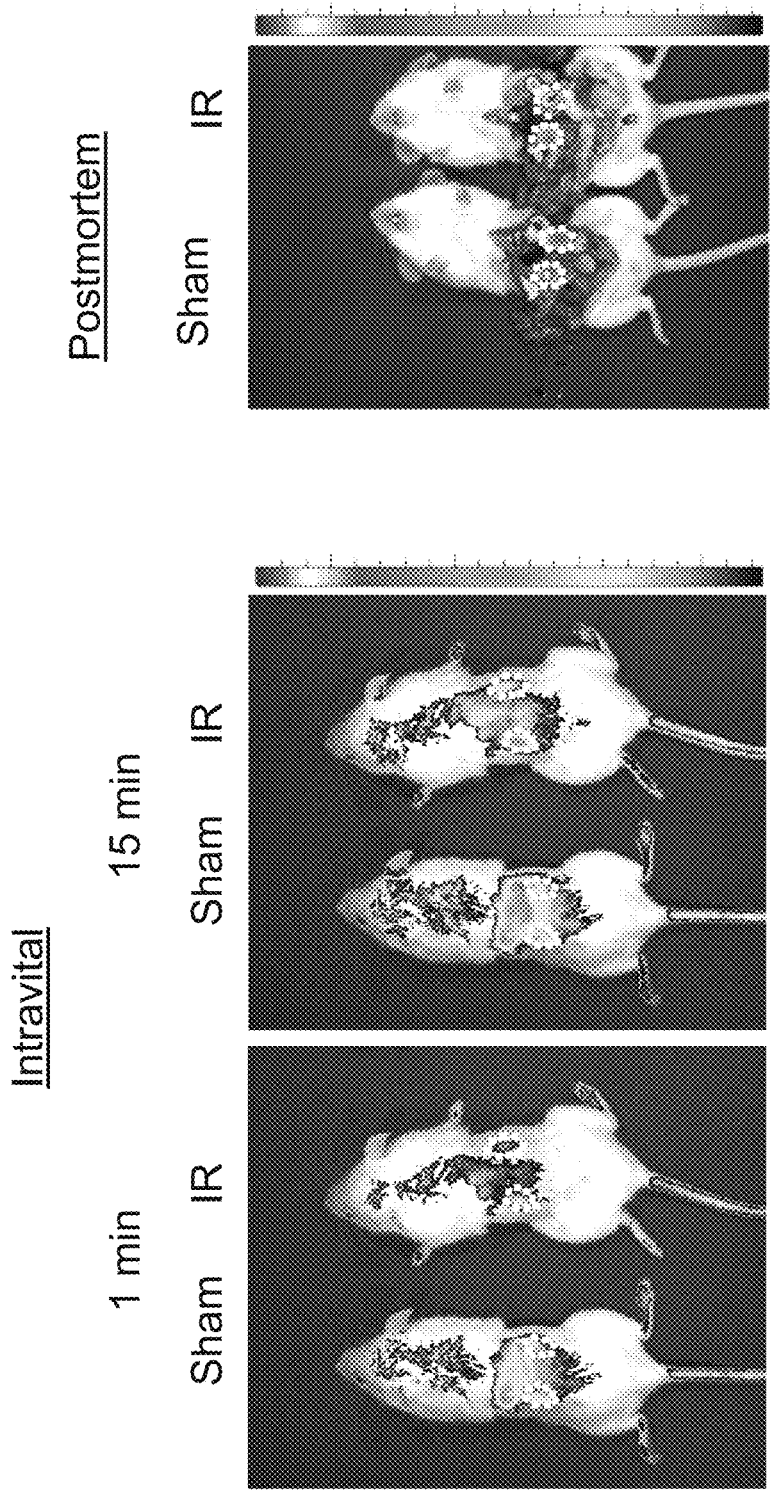
FIG. 9 depicts micrographs and graphs showing in vivo intravital and postmortem measurements of endonuclease activity in mouse kidneys after sham treatment (sham) or ischemia-reperfusion (IR) in (A). In (B), the fluorescence data from the postmortem experiment is presented as average radiant efficiency in kidneys (outlined area) and graphed, *P<0.05.
Figure 9B:
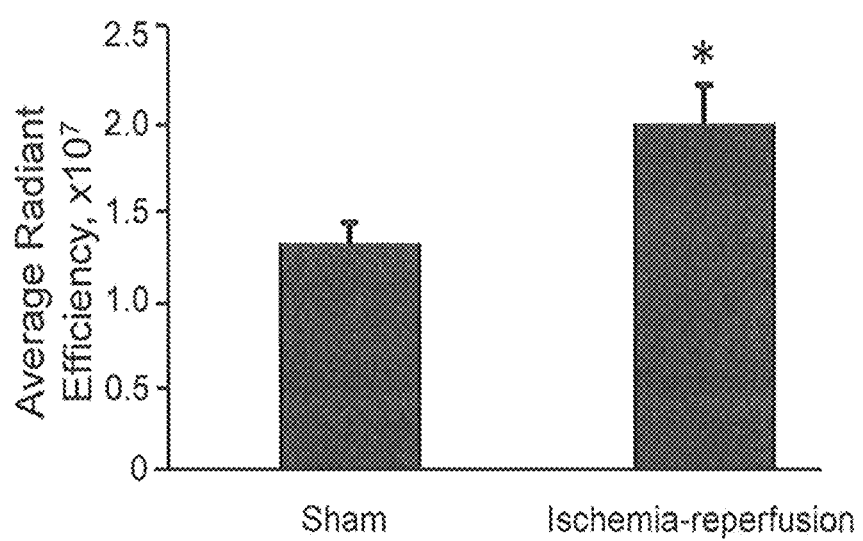

Example 9. Detection of Endonuclease Activity in Renal Ischemia-Reperfusion Model It was previously shown that DNase I activity is elevated after ischemia-reperfusion in kidneys [28]. To test if this can be confirmed using the AB259.3 probe, WT and DNase I KO mice were subjected to renal ischemia-reperfusion. After reperfusion, mice were injected with AB259.3 and Cy5.5 fluorescence was monitored for 15 minutes in live animals and then visualized in kidneys of sacrificed mice. The data demonstrated that while ischemia-reperfusion caused some increase of endonuclease activity in both strains of mice, fluorescence in WT mice was overwhelmingly higher than in DNase I KO mice, suggesting that endonuclease activity in WT kidneys is higher than in DNase I KO kidneys (FIG. 9).

Example 10. Intravital Assessment of Endonuclease Activity in Other Organs

Figure 10A:
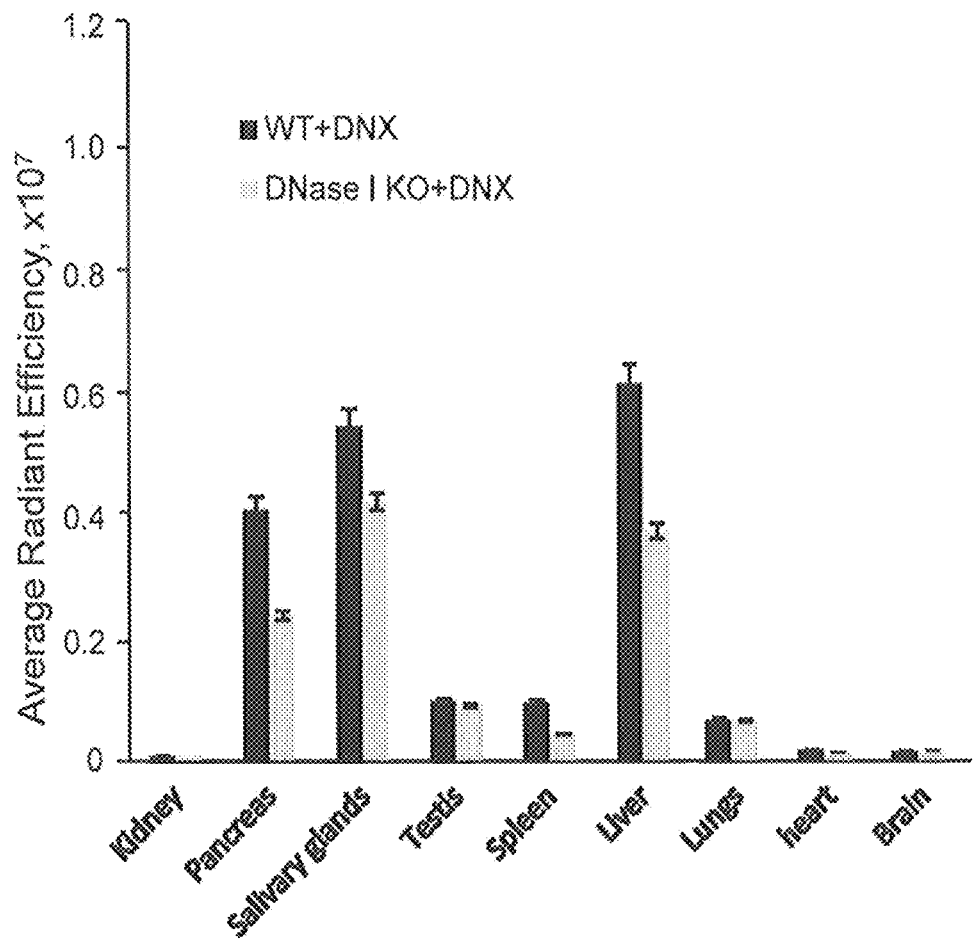
FIG. 10 depicts graphs and images showing endonuclease activity in WT and DNase KO mice with impaired renal circulation after bilateral kidney ligation followed by intravital administration of AB259.3. Fluorescence of individual organs was confirmed by direct IVIS imaging of isolated organs and presented as quantification of average radiant efficiency (A) and representative images of some organs/tissues (B). DNX=bilateral kidney ligation.
Figure 10B:
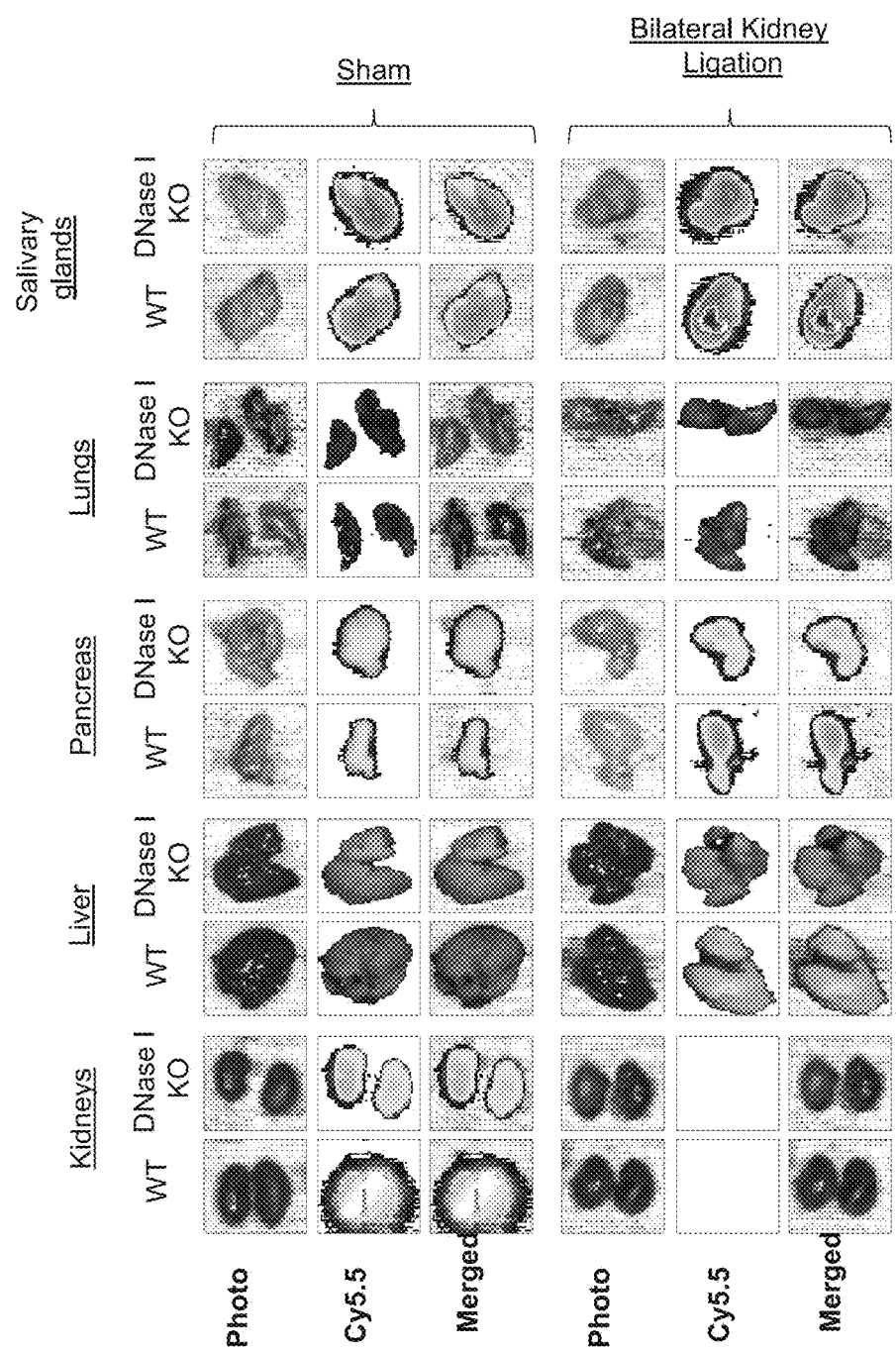
Figure 11A:
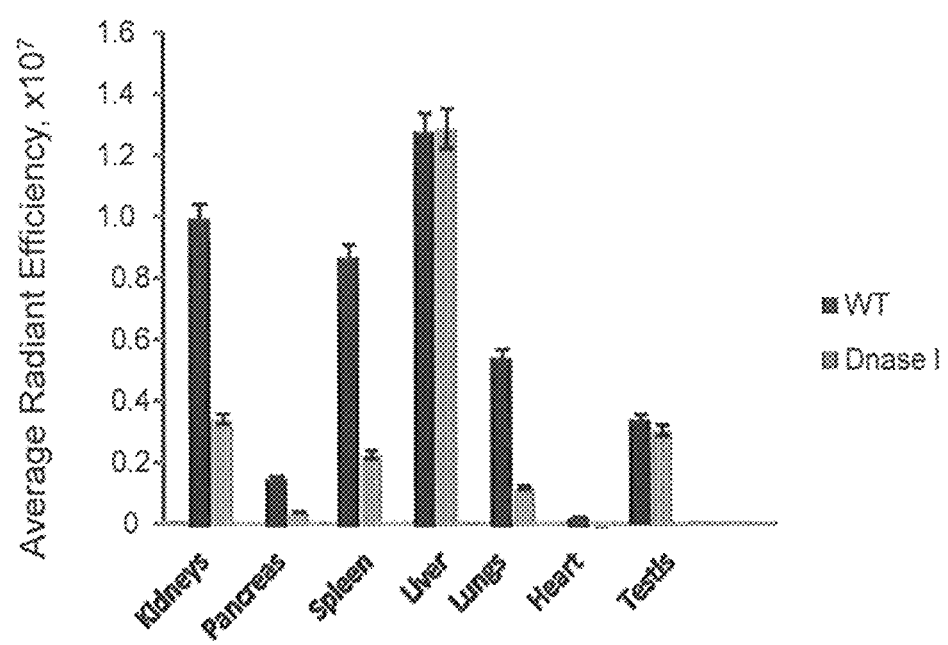
FIG. 11 depicts graphs and images showing endonuclease activity in WT and DNase KO mice with impaired renal circulation after bilateral kidney ligation followed by administration of AB259.3 probe packed in cationic liposomes. Fluorescence of individual organs was confirmed by direct IVIS imaging of isolated organs and presented as quantification of average radiant efficiency (A) and representative images of some organs/tissues (B).
Figure 11B:
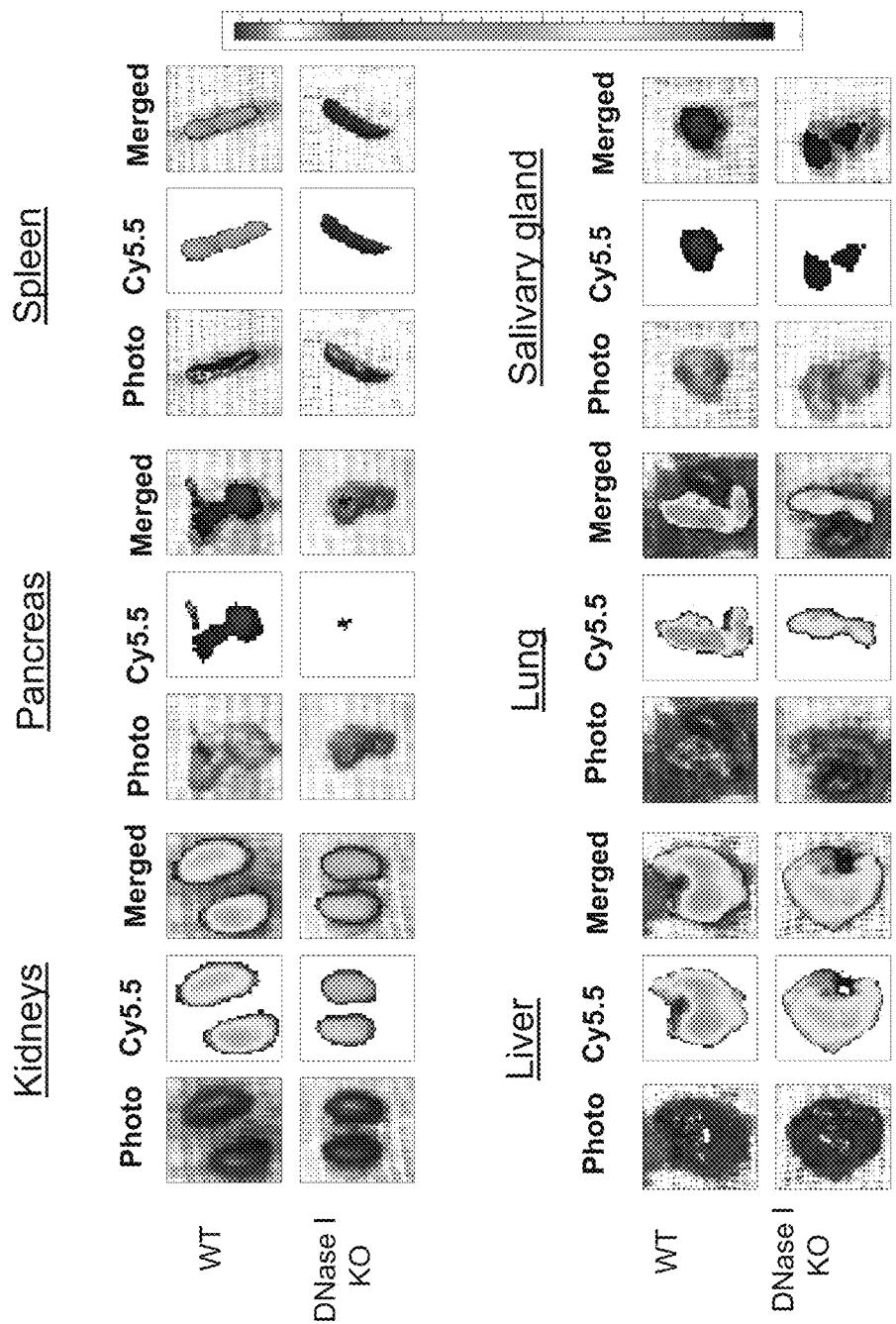

In all the previous in vivo experiments, relative and absolute gain of fluorescence in other organs was rather low due to selective accumulation of probe in kidneys. To check an ability of probe to measure endonuclease activity on other organs, the renal distribution of AB259.3 probe was challenged by two complementary approaches. First group of mice was subjected to bilateral kidney ligation followed by intravital administration of AB259.3 probe and imaging in 3 hours after injection. In this case, the AB259.3 probe accumulation in kidneys was completely abolished and the fluorescence was observed in the projectorial areas of salivary gland, liver, pancreas and lungs (FIGS. 10A and 10B). Relative increase of fluorescence was confirmed by direct postmortem visualization in pancreas, salivary glands, liver, gut, and partially, in lungs and spleen. Notably, pancreas, salivary glands, liver and spleen demonstrated more endonuclease activity in WT compared to DNase I KO mice indicating the presence of active DNase I in these organs. Another group of mice was injected with AB259.3 probe packed in cationic liposomes in attempt to make probe delivery bioavailable to all organs and tissues and less specific to kidneys. In this experiment, the probe was more accessible to kidneys, spleen, liver, intestines, pancreas, testis and salivary glands (FIG. 11). DNase I contributed significantly to endonuclease activity detected in kidneys, spleen, pancreas, salivary glands and lungs. This experiment, therefore, concludes that if renal probe delivery is impaired, AB259.3 probe is suitable for measurement of endonuclease activity in all DNase I-producing organs as well as organs that have other active endonucleases.

Discussion of Examples 1-10

Apoptotic endonucleases play key role in the majority of diseases that are associated with tissue injury. However, until now there was no way to assess endonuclease activity in vivo. This study described the new and highly sensitive technique based on unique fluorescently labeled DNA oligonucleotide that permits in vivo visualization and measurement of endonuclease activity. The probe used for in vivo method can be used to measure endonuclease activity in vitro and biological fluids, in live cells and frozen tissue sections. The in vivo application is especially exciting because it may eventually be applied as intravital diagnostics by monitoring of endonuclease activity injured tissues. The data suggested that AB259.3 probe is selectively accumulated in kidneys and is a very efficient way to measure endonuclease activity in this organ. However, experiment with deprivation of the kidneys or use of cationic liposomes as a mean of delivery revealed that the probe is also useful for visualization of endonuclease activity in other organs.

During elaboration we tested several probes with linear and non-linear structure and came up with the DNA oligo probe that was designed as hairpin, in which one strand is 5 nucleotides longer than the other. This provided the minimal distance that is necessary for self-bleaching of Cy5.5 fluorophores and protruded DNA strand served as favorable target for endonucleases as was shown before [29]. Finally, the hairpin structure also allowed controlling stability of the probe and therefore reduce/standardize the background that should not change unless the probe is getting spontaneously degraded. However, the probe without the hairpin loop was equally effective for measuring DNase activity in live cells.

Due to apparent high affinity of AB259.3 probe to renal parenchyma, this study was largely focused on kidneys: in both kidneys and urine a significant level of DNase I activity was found. In vitro injury of renal epithelial cells by chemotherapeutic agents and in vivo ischemia-reperfusion injury led to even further enhancement of endonuclease activity. These data are in good correspondence with the number of reports suggesting that DNase I is the most active and abundant renal endonuclease, which is induced by injuries and serves as major cell death molecule that mediates tissue injury in kidneys [10, 28, 33]. These data confirmed previous observations that DNase I is responsible for most of endonuclease activity in salivary glands and pancreas, and that is not present in liver, heart and brain [8]. It was confirmed that endonuclease in urine mainly constituted of DNase I [10]. It was also confirmed that activity in pancreas, despite being the major digestive organ, has much lower DNase I activity than salivary gland as previously observed by Lacks [8]. Unexpected observation was high level of DNase I in lung and spleen. The latter is known being a source of DNase gamma and DNase II [34, 35]. Activity in gut and blood could not be visualized and measured apparently because of high level of autofluorescence.

Particular advantage of this technique is the ability to visualize and measure endonuclease activity in specific tissue compartment. For instance, these data suggest that kidneys have endonuclease activity in epithelial rather than stromal compartments, and in tubules rather than glomeruli, and in cytoplasm rather than in nuclei, which are in agreement with previous data suggesting tubular epithelial cells, particularly their cytoplasm, as major source of DNase I [29]. In spleen, the endonuclease activity was provided by DNase I specifically in zones of white pulp that is also in good accordance with our previous observation [30]. Tissues surrounding tumors had more activity that remote normal tissue, also in good correspondence with previous observations [36].

The probe and the method are the first attempt to measure and visualize the endonuclease activity in fluids, cells, tissues and organs. So, there are no previous reports on this subject to allow direct comparison. Although several techniques based on use of DNA as substrate exist [37], they are less sensitive and their use is limited to measurement of endonuclease activity in biological fluids or cell extracts.

Our invention increases the research potential to the next level by providing strong background for functional microscopy and visualization of tissues and organs with the respect of their endonuclease activity and susceptibility for the tissue injury. In future, this technique can be used as valuable scientific tool and potential prototype for new intravital non-invasive modalities in diagnostics of injuries to selective organs underlying various diseases. Examples of such diseases may be stroke, myocardial infarction, and acute organ failures. It can also be applied to cancer diagnostics and monitoring of therapy. Modification of the probe may allow measuring specific endonuclease expressed in different tissues. Making the probe more cell-permeable and using more powerful fluorophores would increase the sensitivity and diagnostic power of the probe.

Methods of Examples 1-10

(a) DNA-NIRF Probes, Reagents and Chemicals

All reagents and chemicals were purchased from Sigma (St. Louis, Mo.) unless specified otherwise. DNA probes: AB259.1 (SEQ ID NO: 1): [Cy5.5]AACACTCCGATGAGTGTA[Cy5.5], AB259.3 (SEQ ID NO: 2): [Cy5.5] AACACTCCGATGAGTGTAGAATGT[Cy5.5], and AB259.5 (SEQ ID NO: 3) [Cy5.5]AACACTCCGATGAGTGTAGAATGTACGAGT[Cy5.5] substrates were synthesized and HPLC purified by GeneLink (Hawthorne, N.Y.).

(b) Kinetic and End-Point Fluorescence Measurement In Vitro

All cell-free experiments were performed using the BioTek Synergy 5 fluorescent plate reader. Before experiments, optimal excitation and emission wavelengths were determined. For this, excitation and emission were scanned in the ranges of 600-680 nm and 690-705 nm, respectively. The optimal excitation/emission was determined to be 665/703 nm. All kinetic and endpoint measurements were done in a total volume of 100 µl at 37° C. Unless stated otherwise, DNA substrate was used in final concentration 0.5 µM reconstituted in endonuclease activity assay (EAA) buffer (2 mM $CaCl_2$, 5 mM $MgCl_2$, 10 mM Tris-HCl, pH 7.4) in a 96-well plate. After measurement of starting fluorescence, DNase I or tested material (diluted 1:20 urine or 1:100 serum) were added to the reconstituted probe, rapidly mixed and fluorescence was monitored for up to 60 min with 30-sec intervals. In some instances, EDTA (final concentration 200 µM) or NaOH (50 mM) was added to terminate the reaction. For the experiments that involved assessment of fluorescence after DNA denaturing, probes were tested in Cepheid real-time PCR system using Cy5 setting (Sunnyvale, Calif.).

(c) Measurement of Endonuclease Activity in Cell Cultures

Rat proximal tubular epithelial NRK-52E cells were used to test the ability of AB259.3 probe to measure endonuclease activity. The cells were seeded in a 24-well plate at 50,000 cells per well in complete DMEM medium supplemented with 10% fetal bovine serum. Cells were transfected with the AB259.3 probe using Lipofectamin LTX and then subjected to spinning disk confocal fluorescent time-lapse microscopy in 628/40-692/40 spectrum every 10 min for 8 hours using Olympus IX-81 image system equipped with Hamamatsu ORCA-ER camera and LiveCell microenvironmental control chamber (Pathology Devices Inc., Westminster, Md.). In separate experiment, cells were treated with either 25 µM cisplatin or 50 µM camptothecin for 8 hours, followed by 1-hour transfection with AB259.3 probe and 8-hour time-lapse imaging session with 10-min intervals using the same microscopy system.

(d) Measurement of Endonuclease Activity in Tissue Cryosections

Specimens of kidney, liver, spleen and testis tissues were removed from euthanized mice, immersed in OCT medium, rapidly frozen by Fisher Freeze-it and kept on dry ice for no longer than 1 hour prior slicing. Tissue cryosections (8-μm thick) were prepared using the Microm HM 505E cryotome, placed to the Fisher Plus slides and immediately exposed with 0.5 μM AB259.3 probe diluted in EAA buffer. In control samples, applied probe contained EAA buffer supplemented with 200 μM EDTA. Images were taken in 628/40-692/40 spectrum every 30 sec for 10 min in 10 random XY coordinates. Three sections from each specimen were analyzed separately. Maximal velocity of increasing fluorescence was averaged for each section.

(e) Animal Experiments

All animal experiments were approved by the Animal Care and Use Committee of the Central Arkansas Veterans Healthcare System. DNase I knockout (KO) mice (CD-1 background) were obtained from Dr. Tariq Moroy of the University of Essen, Germany and previously reported by Napirei et al. [15]. Mice were bred as heterozygotes and genotyped by PCR as described before [10]. Male DNase I KO mice and their WT counterparts at the age 8-10 weeks were used for all experiments. All procedures with mice were performed under general anesthesia with 50 mg/kg ketamine. For subcutaneous administration, mice were injected with 10 μl of 0.1 μM AB259.3 in the dorsal subcutaneous site. For systemic visualization, AB259.3 was injected intravenously at 50 nmol/kg in tail vein. Kidney ischemia-reperfusion was performed as previously reported [28]. Because prolonged ischemia and reperfusion impaired the normal microcirculation and bioavailability of the probe, the time of ischemia and reperfusion was shortened to 15 min and 4 hours respectively. Bilateral kidney ligation was performed on anesthetized DNase I KO or WT mice. Renal pedicles were surgically ligated using 4.0 silk sutures. Immediately after closure of surgical wound, mice were intravenously injected with AB259.3 probe. Prostate cancer xenografts model was developed in 8-week-old male SCID mice (Jackson Labs). Human prostate cancer PC3 cells ($2\times10^7$) were injected into prostate of mice under isofluorane anesthesia (2%, 02 to effect) and allowed 5 weeks to grow, after which the tumors were excited from the animals and rapidly frozen in OCT medium for further analyses. In some experiments, mice were injected with AB259.3 that was coupled with cationic liposomes. The liposomes were prepared as described previously [29]. Briefly, dimethyldioctadecyl ammonium and cholesterol were mixed in 1:1 molar ratio, desiccated, rehydrated with 5% dextrose, and sonicated for 15-20 min. The liposomes were then incubated with AB259.3 probe at 1:60 molar ratio, respectively, and injected intravenously in mice at 50 nmol/kg.

(f) Intravital and Postmortem Imaging

Imaging of live and euthanized mice or their isolated organs were performed using Xenogen IVIS Image System 200 (Caliper Life Sciences, Hopkinton, Mass.) equipped with Living Image® Software. Live animals (4-6 per session) were imaged kinetically with 1-min intervals for 10-15 min. Euthanized animals and isolated organs were imaged in a static regimen. Other parameters were as follows: exposure: 0.5 sec; sensitivity: low; distance from surface: 2 cm for animals, 1 cm for isolated organs; binning: 1×1. Quantification of the manually designated areas was performed based on average radiant efficiency with the fixed min-max dynamic range.

(g) Statistics

Statistical analysis was performed using ANOVA or Student's t-test. Results were expressed as mean □ SEM. $P<0.05$ was considered significant.

REFERENCES OF EXAMPLES 1-7

Literature Cited

1. Hengartner M O: Apoptosis. DNA destroyers. Nature 412(6842), 27, 29, 2001
2. Baranovskii A G, Buneva V N, Nevinsky G A: Human deoxyribonucleases. Biochemistry (Mosc) 69(6), 587-601, 2004
3. Yang W: Nucleases: diversity of structure, function and mechanism. Q Rev Biophys 44(1), 1-93, 2011
4. Widlak P, Garrard W T: Roles of the major apoptotic nuclease-DNA fragmentation factor-in biology and disease. Cell Mol Life Sci 66(2), 263-274, 2009
5. Evans C J, Aguilera R J: DNase II: genes, enzymes and function. Gene 322(1-15, 2003
6. Apostolov E O, Wang X, Shah S V, Basnakian A G: Role of EndoG in development and cell injury. Cell Death Differ 14(11), 1971-1974, 2007
7. Shiokawa D, Tanuma S: Characterization of human DNase I family endonucleases and activation of DNase gamma during apoptosis. Biochemistry 40(1), 143-152, 2001
8. Lacks S A: Deoxyribonuclease I in mammalian tissues. Specificity of inhibition by actin. J Biol Chem 256(6), 2644-2648, 1981
9. Polzar B, Peitsch M C, Loos R, Tschopp J, Mannherz H G: Overexpression of deoxyribonuclease I (DNase I) transfected into COS-cells: its distribution during apoptotic cell death. Eur J Cell Biol 62(2), 397-405, 1993
10. Basnakian A G, Apostolov E O, Yin X, Napirei M, Mannherz H G, Shah S V: Cisplatin nephrotoxicity is mediated by deoxyribonuclease I. J Am Soc Nephrol 16(3), 697-702, 2005
11. Kitahara Y, Kawane K, Nagata S: Interferon-induced TRAIL-independent cell death in DNase II−/− embryos. Eur J Immunol 40(9), 2590-2598, 2010
12. Wang X, Tryndyak V, Apostolov E O, Yin X, Shah S V, Pogribny I P, Basnakian A G: Sensitivity of human prostate cancer cells to chemotherapeutic drugs depends on EndoG expression regulated by promoter methylation. Cancer Lett 270(1), 132-143, 2008
13. Basnakian A G, Apostolov E O, Yin X, Abiri S O, Stewart A G, Singh A B, Shah S V: Endonuclease G promotes cell death of non-invasive human breast cancer cells. Exp Cell Res 312(20), 4139-4149, 2006
14. Napirei M, Basnakian A G, Apostolov E O, Mannherz H G: Deoxyribonuclease 1 aggravates acetaminophen-induced liver necrosis in male CD-1 mice. Hepatology 43(2), 297-305, 2006
15. Napirei M, Karsunky H, Zevnik B, Stephan H, Mannherz H G, Moroy T: Features of systemic lupus erythematosus in Dnase1-deficient mice. Nat Genet 25(2), 177-181, 2000
16. Martinez-Valle F, Balada E, Ordi-Ros J, Bujan-Rivas S, Sellas-Fernandez A, Vilardell-Tarres M: DNase 1 activity in patients with systemic lupus erythematosus: relationship with epidemiological, clinical, immunological and therapeutical features. Lupus 18(5), 418-423, 2009
17. Lichtenbelt K D, Sinke R J, Ausems M G, Kroos M A, Reuser A J, Wokke J J: Frequency of the deletion polymorphism of DNASE1 L1 in 137 patients with acid maltase deficiency (Pompe disease). Exp Mol Pathol 80(3), 308-309; author reply 310, 2006

18. Gilchrist K W, Gilbert E F, Goldfarb S, Goll U, Spranger J W, Opitz J M: Studies of malformation syndromes of man XIB: the cerebro-hepato-renal syndrome of Zellweger: comparative pathology. Eur J Pediatr 121(2), 99-118, 1976

19. McDermott-Roe C, Ye J, Ahmed R, Sun X M, Serafin A, Ware J, Bottolo L, Muckett P, Canas X, Zhang J, Rowe G C, Buchan R, Lu H, Braithwaite A, Mancini M, Hauton D, Marti R, Garcia-Arumi E, Hubner N, Jacob H, Serikawa T, Zidek V, Papousek F, Kolar F, Cardona M, Ruiz-Meana M, Garcia-Dorado D, Comella J X, Felkin L E, Barton P J, Arany Z, Pravenec M, Petretto E, Sanchis D, Cook S A: Endonuclease G is a novel determinant of cardiac hypertrophy and mitochondrial function. Nature 478(7367), 114-118, 2011

20. Yan B, Wang H, Peng Y, Hu Y, Wang H, Zhang X, Chen Q, Bedford J S, Dewhirst M W, Li C Y: A unique role of the DNA fragmentation factor in maintaining genomic stability. Proc Natl Acad Sci USA 103(5), 1504-1509, 2006

21. Yan B, Wang H, Xie D, Wakamatsu N, Anscher M S, Dewhirst M W, Mitchel R E, Chen B J, Li C Y: Increased skin carcinogenesis in caspase-activated DNase knockout mice. Carcinogenesis 30(10), 1776-1780, 2009

22. Abel F, Sjoberg R M, Ejeskar K, Krona C, Martinsson T: Analyses of apoptotic regulators CASP9 and DFFA at 1P36.2, reveal rare allele variants in human neuroblastoma tumours. Br J Cancer 86(4), 596-604, 2002

23. Hara S, Miyake H, Arakawa S, Kamidono S, Hara I: Over expression of inhibitor of caspase 3 activated deoxyribonuclease in human renal cell carcinoma cells enhances their resistance to cytotoxic chemotherapy in vivo. J Urol 166(6), 2491-2494, 2001

24. Rajandram R, Pat B K, Li J, Johnson D W, Gobe G C: Expression of apoptotic tumour necrosis factor receptor-associated factor, caspase recruitment domain and cell death-inducing DFF-45 effector genes in therapy-treated renal cell carcinoma. Nephrology (Carlton) 14(2), 205-212, 2009

25. Nishimura K, Tanuma S: Presence of DNase gamma-like endonuclease in nuclei of neuronal differentiated PC12 cells. Apoptosis 3(2), 97-103, 1998

26. Komuro A, Hodge D O, Gores G J, Bourne W M: Cell death during corneal storage at 4 degrees C. Invest Ophthalmol Vis Sci 40(12), 2827-2832, 1999

27. Weissleder R, Tung C H, Mahmood U, Bogdanov A, Jr.: In vivo imaging of tumors with protease-activated near-infrared fluorescent probes. Nat Biotechnol 17(4), 375-378, 1999

28. Basnakian A G, Ueda N, Kaushal G P, Mikhailova M V, Shah S V: DNase I-like endonuclease in rat kidney cortex that is activated during ischemia/reperfusion injury. J Am Soc Nephrol 13(4), 1000-1007, 2002

29. Wang Q F, Tilly K I, Tilly J L, Preffer F, Schneyer A L, Crowley W F, Jr., Sluss P M: Activin inhibits basal and androgen-stimulated proliferation and induces apoptosis in the human prostatic cancer cell line, LNCaP. Endocrinology 137(12), 5476-5483, 1996

30. Apostolov E O, Soultanova I, Savenka A, Bagandov O O, Yin X, Stewart A G, Walker R B, Basnakian A G: Deoxyribonuclease I is essential for DNA fragmentation induced by gamma radiation in mice. Radiat Res 172(4), 481-492, 2009

31. Basnakian A G, Singh A B, Shah S V: Identification and expression of deoxyribonuclease (DNase) I alternative transcripts in the rat. Gene 289(1-2), 87-96, 2002

32. Kyprianou N, English H F, Isaacs J T: Activation of a Ca2+-Mg2+-dependent endonuclease as an early event in castration-induced prostatic cell death. Prostate 13(2), 103-117, 1988

33. Kishi K, Yasuda T, Takeshita H: DNase I: structure, function, and use in medicine and forensic science. Leg Med (Tokyo) 3(2), 69-83, 2001

34. Wang C C, Lu S C, Chen H L, Liao T H: Porcine spleen deoxyribonuclease II. Covalent structure, cDNA sequence, molecular cloning, and gene expression. J Biol Chem 273(27), 17192-17198, 1998

35. Shiokawa D, Iwamatsu A, Tanuma S: Purification, characterization, and amino acid sequencing of DNase gamma from rat spleen. Arch Biochem Biophys 346(1), 15-20, 1997

36. Basnakian A G, Boubnov N V, Kirsanova I D, Votrin, I I: Nuclear topoisomerase I and DNase activities in rat diethylnitrosamine-induced hepatoma, in regenerating and fetal liver. Biochem Int 24(3), 429-437, 1991

37. Basnakian A G, James S J: Quantification of 3'OH DNA breaks by random oligonucleotide-primed synthesis (ROPS) assay. DNA Cell Biol 15(3), 255-262, 1996

What is claimed is:

1. A method for detecting nucleic acid cleavage in a sample or in a subject, the method comprising:
   (i) providing a nucleic acid probe selected from the group consisting of Cy5.5-AACACTCCGATGAGTGTA-Cy5.5 (SEQ ID NO: 1), Cy5.5-AACACTCCGATGAGTGTAGAATGT-Cy5.5 (SEQ ID NO: 2), and Cy5.5-AACACTCCGATGAGTGTAGAATGTACGAGT-Cy5.5 (SEQ ID NO: 3);
   (ii) contacting the sample or the subject with the nucleic acid probe and detecting fluorescence in the sample or the subject, whereby fluorescence in the sample or the subject indicates nucleic acid cleavage of at least one component of the nucleic acid probe; and
   (iii) optionally, quantifying the fluorescence in the sample.

2. The method of claim 1, wherein nucleic acid cleavage is enzymatic and the enzyme is a deoxyribonuclease (DNAse) and the nucleic acid probe is a deoxyribonucleic acid (DNA) probe.

3. The method of claim 2, wherein the DNase is further selected from the group consisting of DNase I, DNase X, DNase gamma, DNAse 2alpha, DNase 2beta, L-DNase-2, EndoG, CAD, DNAse IV, UvrABC endonuclease, RecBCD, and restriction enzyme.

4. The method of claim 1, wherein the fluorescence is measured in vitro, in vivo, ex vivo, or in situ.

5. The method of claim 1, wherein the sample is selected from the group consisting of a cell, a cell lysate, a protein sample, a tissue sample, a homogenized tissue sample, an organ, a homogenized organ, a biopsy sample, and bodily fluid.

6. The method of claim 1, wherein the nucleic acid cleavage, if present, is enzymatic and the enzyme is DNase I, and the fluorophores are near-infrared fluorophores.

7. A composition comprising a nucleic acid probe, the nucleic acid probe comprising two components: A1-A2-A3 and A5-A6-A7, and optionally a third component, A4, wherein:
   (a) A1 and A7 are fluorophores,
   (b) A2 is adenine and A6 is a nucleic acid sequence selected from the group consisting of A, AGAATGT, and AGAATGTACGAGT (SEQ ID NO: 6),
   (c) A3 is the nucleic acid sequence ACACTC and A5 is the nucleic acid sequence GAGTGT, such that A3 and A5 associate when A1-A2-A3 and A5-A6-A7 are not cleaved and disassociate when at least one of A1-A2-A3 or A5-A6-A7 is cleaved, and
   (d) A4 is the nucleic acid sequence CGAT,
   whereby the fluorescence of A1 and A7 is quenched when A3 and A5 associate and is detectable when A3 and A5 disassociate.

8. The composition of claim 7, wherein the fluorophores are near-infrared fluorophores.

9. The composition of claim 7 wherein the nucleic acid probe is selected from the group consisting of Cy5.5-AACACTCCGATGAGTGTA-Cy5.5 (SEQ ID NO: 1), Cy5.5-AACACTCCGATGAGTGTAGAATGT-Cy5.5 (SEQ ID NO: 2), and Cy5.5-AACACTCCGATGAGTGTAGAAT-GTACGAGT-Cy5.5 (SEQ ID NO: 3).

* * * * *

SEQUENCE LISTING

```
<160> NUMBER OF SEQ ID NOS: 9

<210> SEQ ID NO 1
<211> LENGTH: 18
<212> TYPE: DNA
<213> ORGANISM: Artificial Sequence
<220> FEATURE:
<223> OTHER INFORMATION: SYNETHESIZED
<220> FEATURE:
<221> NAME/KEY: misc_feature
<222> LOCATION: (3)..(3)
<223> OTHER INFORMATION: Cy5.5
<220> FEATURE:
<221> NAME/KEY: misc_feature
<222> LOCATION: (5)..(5)
<223> OTHER INFORMATION: Cy5.5

<400> SEQUENCE: 1
aacactccga tgagtgta                                                   18
```

```
<210> SEQ ID NO 2
<211> LENGTH: 24
<212> TYPE: DNA
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (3)..(3)
<223> OTHER INFORMATION: CY5.5
<220> FEATURE:
<221> NAME/KEY: MISC_FEATURE
<222> LOCATION: (5)..(5)
<223> OTHER INFORMATION: CY5.5

<400> SEQUENCE: 2
aacactccga tgagtgtaga atgt                                              24

<210> SEQ ID NO 3
<211> LENGTH: 30
<212> TYPE: DNA
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (3)..(3)
<223> OTHER INFORMATION: Cy5.5
<220> FEATURE:
<221> NAME/KEY: MISC_FEATURE
<222> LOCATION: (5)..(5)
<223> OTHER INFORMATION: Cy5.5

<400> SEQUENCE: 3
aacactccga tgagtgtaga atgtacgagt                                        30

<210> SEQ ID NO 4
<211> LENGTH: 18
<212> TYPE: DNA
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (5)..(5)
<223> OTHER INFORMATION: cy5.5

<400> SEQUENCE: 4
aacactccga tgagtgta                                                     18

<210> SEQ ID NO 5
<211> LENGTH: 13
<212> TYPE: DNA
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (3)..(3)
<223> OTHER INFORMATION: fluorophore

<400> SEQUENCE: 5
gagtgtagaa tgt                                                          13

<210> SEQ ID NO 6
<211> LENGTH: 13
<212> TYPE: DNA
<213> ORGANISM: Artificial Sequence
<220> FEATURE:
<223> OTHER INFORMATION: SYNTHESIZED
```

```
<400> SEQUENCE: 6
agaatgtacg agt                                                               13

<210> SEQ ID NO 7
<211> LENGTH: 18
<212> TYPE: DNA
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (3)..(3)
<223> OTHER INFORMATION: fluorophore
<220> FEATURE:
<221> NAME/KEY: MISC_FEATURE
<222> LOCATION: (5)..(5)
<223> OTHER INFORMATION: fluorophore

<400> SEQUENCE: 7
aacactccga tgagtgta                                                          18

<210> SEQ ID NO 8
<211> LENGTH: 24
<212> TYPE: DNA
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (3)..(3)
<223> OTHER INFORMATION: fluorophore
<220> FEATURE:
<221> NAME/KEY: MISC_FEATURE
<222> LOCATION: (5)..(5)
<223> OTHER INFORMATION: fluorophore

<400> SEQUENCE: 8
aacactccga tgagtgtaga atgt                                                   24

<210> SEQ ID NO 9
<211> LENGTH: 30
<212> TYPE: DNA
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (3)..(3)
<223> OTHER INFORMATION: fluorophore
<220> FEATURE:
<221> NAME/KEY: MISC_FEATURE
<222> LOCATION: (5)..(5)
<223> OTHER INFORMATION: fluorophore

<400> SEQUENCE: 9
aacactccga tgagtgtaga atgtacgagt                                             30
```